US007989602B2

(12) United States Patent
Singh-Gill et al.

(10) Patent No.: US 7,989,602 B2

(45) Date of Patent: Aug. 2, 2011

(54) SYNTHETIC MOLECULES HAVING IMMUNE ACTIVITY

(75) Inventors: Gurmit Singh-Gill, Dunedin (NZ); David Samuel Larsen, Duedin (NZ); Jeremy David Jones, Dunedin (NZ); Wayne Bruce Severn, Upper Hutt (NZ); Jacquie Lucille Harper, Lower Hutt (NZ); Gavin Painter, Lower Hutt (NZ)

(73) Assignees: The Malaghan Institute of Medical Research, Wellington (NZ); University of Otago, Dunedin (NZ); Agresearch Limited, Hamilton (NZ)

( * ) Notice: Subject to any disclaimer, the term of this patent is extended or adjusted under 35 U.S.C. 154(b) by 573 days.

(21) Appl. No.: 10/580,147

(22) PCT Filed: Nov. 18, 2004

(86) PCT No.: PCT/NZ2004/000293

§ 371 (c)(1),
(2), (4) Date: Mar. 30, 2007

(87) PCT Pub. No.: WO2005/049631

PCT Pub. Date: Jun. 2, 2005

(65) Prior Publication Data

US 2008/0249037 A1 Oct. 9, 2008

(30) Foreign Application Priority Data

Nov. 18, 2003 (NZ) ........................................ 529603
May 31, 2004 (NZ) ........................................ 533245

(51) Int. Cl.
*C07H 23/00* (2006.01)
*A01N 43/04* (2006.01)
*A61K 31/70* (2006.01)

(52) U.S. Cl. ........................................ 536/17.1; 514/25

(58) Field of Classification Search ........................ None
See application file for complete search history.

(56) References Cited

FOREIGN PATENT DOCUMENTS

| | | | |
|---|---|---|---|
| JP | 06271579 A2 * | 6/1994 |
| JP | 06271597 A2 | 9/1994 |
| WO | WO 94/21656 | 9/1994 |
| WO | WO 0202140 A1 * | 1/2002 |

OTHER PUBLICATIONS

Sanderson et al. The Journal of Biological Chemistry, vol. 237, No. 12, Dec. 1982, pp. 3603-3613.*

Bennett, C.F. et al. 1997 "An ICAM-1 antisense oligonucleotide prevents and reverses dextran sulfate sodium-induced colitis in mice" *J Pharmacol Exper Ther* 280:988-1000.

Crossman, A. et al. 1997 "Parasite glycoconjugates. Part 7. Synthesis of further substrate analogues of early intermediates in the biosynthetic pathway of glycosylphosphatidylinositol membrane anchors" *J Chem Soc, Perkin Trans* 1:2769-2774.

Dreef C.E. et al. 1991 "Synthesis of 5-phosphonate analogues of myo-inositol 1,4,5-trisphosphate: possible intracellular calcium antagonists" *Tetrahedron Letters* 32:6021-6024.

Erb K.J. et al .1998 "Infection of mice with *Mycobacterium bovis*-Bacillus Calmete-Guérin (BCG) suppresses allergen-induced airway eosinophilia" *J Exp Med* 187:561-569.

Gigg, J. et al. 1985 "Synthesis of propyl 4-O-(3,6-Di-O-methyl-β-D-glucopyranosyl)-2,3-di-O-methyl-α-D-rhamnopyranoside" *Carbohydrate Res* 141:91-97.

Gilleron, M. et al. 2001 "Acylation state of the phosphatidylinositol manosides from *Mycobacterium bovis* Bacillus Calmette Guérin and ability to induce granuloma and recruit natural killer T cells" *J Biol Chem* 276:34896-34904.

Gilleron, M et al. 2003 "Acylation state of the phosphatidylinositol hexamannosides from *Mycobacterium bovis* Bacillus Calmette Guérin and *Mycobacterium tuberculosis* H37Rv and its implication in Toll-like receptor response" *J Biol Chem* 278:29880-29889.

Green, M.M. et al. 1987 "Broken worm and wormlike models for polyisocyanates" *Macromolecules* 20:2636-2638.

Gross, D. M. et al. 1998 "Identification of LFA-1 as a candidate autoantigen in treatment-resistant lyme arthritis" *Science* 281:703-706.

Halloran, M.M. et al. 1996 "Cellular adhesion molecules in rat adjuvant arthritis" *Arthritis and Rheumatism* 39:810-819.

Hasegawa, Y. et al. 1994 "Prevention of autoimmune insulin-dependent diabetes in non-obese diabetic mice by anti-LFA-1 and anti-ICAM-1 mAB" *Int Immunol* 6: 831-838.

Herold, K.C. et al. 1994 "Prevention of autoimmune diabetes by treatment with anti-LFA-1 and anti-ICAM-1 monoclonal antibodies" *Cellular Immunol* 157:489-500.

Herz U et al. 1998 "BCG infection suppresses allergic sensitization and development of increased airway reactivity in an animal model" *J Allergy Clin Immunol* 102:867-874.

Hirooka M. et al. 2003 "Glycosylation using hemiacetal sugar derivatives: synthesis of O-α-D-rhamnosyl-(1→3)-O-α-D-rhamnosyl-(1→2)-D-rhamnose and )-α-D-Tyvelosyl-(1→3)-O-α-D-mannosyl-(1→4)-L-rhamnose" Bull Chem Soc Jpn 76:1409-1421.

Hirth G et al. 1982 "Synthesis of glyceryletherphosphatides. Part 1. Preparation of 1-O-octadecyl-2-O-acetyl-sn-glyceryl-3-phosphorylcholine ('platelet activating factor'), its enantiomers and some analogous compounds" Helvetica Chemica Acta 65:1059-1084.

Hirth G et al. 1983 "Synthesis of glyceryletherphosphatides. Part 2. Preparation of 2-O-acetyl-1-O-[(Z)-9-octadecenyl]-sn-glyceryl-3-phosphorylcholine (Oleyl-PAF'), of its enantiomer and some analogous, unsaturated compounds" *Helvetica Chimica Acta* 66: 1210-1240. Iranpoor, N. et al .1996 "FeCI3-6H20 supported on SiO2 catalyzed ring-opening of epoxides with alchols, acetic acid, water, chloride, bromide, and nitrate ions" *Synthesis*: 1473-1476.

Itano K. et al .1980 "Stereospecific preparation of monoglucosides of optically active *trans*-1,2-cyclohexanediiols by enzymic trans-D-glucosylation and $^{13}$C-N.M.R. spectroscopy of the resulting mono-D-glucopyranosides" *Carbohydrate Res* 87:27-34.

Kakimoto, K. et al. 1992 "The effect of anti-adhesion molecule antibody on the development of collagen-induced arthritis" *Cellular Immunol* 142:326-337.

Knoerzer, D.B. et al. 1997 "Clinical and histological assessment of collagen-induced arthritis progression in the diabetes-resistant BB/Wor Rat" *Toxicol Pathol* 25:13-19.

Koizumi, K. et al. 1991 "Characterization of five isomers of branched cyclomaltoheptaose (βCD) having degree of phoymerization (d.p.) = 9: Reinvestigation of three positional isomers of diglucosyl-βCD" *Carbohydrate Res* 215:127-136.

(Continued)

*Primary Examiner* — Layla Bland

(74) *Attorney, Agent, or Firm* — Knobbe Martens Olson & Bear LLP

(57) ABSTRACT

The present invention is directed to synthetic molecules having biological activity similar to PIM (acyl glycerol phosphatidylinositol manno-oligosaccharide) activity, for use in the treatment and prevention of inflammatory or immune cell mediated diseases or disorders.

9 Claims, 11 Drawing Sheets

OTHER PUBLICATIONS

Koto, S. et al. 1976 "Preparation of 2,3,4,6-tetra-O-benzyl-D-mannose" *Bull Chem Soc of Jpn* 49:2639-2640.

Koto, S. et al. 1992 "Dehydrative glycosylation using heptabenzyl derivatives of glucobioses and lactose" *Bull Chem Soc Jpn* 65:3257-3274.

Lindberg, J. et al. 2002 "Efficient synthesis of phospholipids from glycidyl phosphates" *J Org Chem* 67:194-199.

Lindhorst, T.K. et al. 2000 "Cluster mannosides as inhibitors of type 1 fimbriae-mediated adhesion of *Escherichia coli*: pentaerythritol derivatives as scaffolds" Eur J Org Chem 2027-2034.

Mulligan, M.S. et al. 1995 "Comparmentalized roles for leukocytic adhesion molecules in lung inflammatory injury" *J Immunol* 154:1350-1363.

Oppenheimer-Marks, N. et al. 1998 "Interleukin 15 is produced by endothelial cells and increases the transendothelial migration of T-cells in vitro and in the SCID mouse-human rheumatoid arthritis model in vivo" *J Clin Invest* 101:1261-1272.

Rajanbabu, T.V. et al. 1989 "Stereochemical control in hex-5-enyl radical cyclizations: from carbohydrates to carbocycles" *J Am Chem Soc* 111:1759-1769.

Randolph D.A. et al. 1999 "Cooperation between Th1 and Th2 cells in a murine model of eosinophilic airway inflammation" *J Clin Invest* 104:1021-1029.

Schimmer, R.C. et al. 1998 "Streptococcal cell wall-induced arthritis: requirements for IL-4, IL-10, IFN-γ, and monocytes chemoattractant protein-1" *J Immunol* 160:1466-1471.

Severn, W.B. et al. 1997 "Improved procedure for the isolation and purification of lipoarabinomannan from *Mycobacterium bovis* strain AN5" *J Microbiol Meth* 28:123-130.

Van Boeckel C.A.A. et al. 1979 "Synthesis of glucosyl phosphatidylglycerol via a phosphotriester intermediate" *Tetrahedron Letters* 37:3561-3564.

Van Boeckel C.A.A. et al. 1981 "Phosphotriester approach to the synthesis of β-glucosylated mono and diphosphatidyl glycerols: bacterial cell wall components" Tetrahedron 37:3751-3761.

Watanabe Y. et al. 1993 "Glycosylation based on phosphite chemistry" *Synlett*, 115-116.

Watanabe Y. et al. 1994 "Glycosylation using glycosyl phosphite as a glycosyl donor" *Tetrahedron* 50:6523-6536.

Zalipsky S. et al .1999 "New chemoenzymatic approach to glycol-lipopolymers: practical preparation of functionally active galactose-poly(ethylene glycol)-distearoylphosphatidic acid (Gal-PEG-DSPA) conjugate" *Chem Commun* 7:653-654.

Zalipsky S et al. 2002 "Phospholipase D mediated synthesis of PEG-lipids for liposomal drug delivery" *Polymer Preprints* 43:710.

* cited by examiner 1 2 3 4 6 7

2

8

9

10

11

α to β= 4:1

12

+ 13 (β anomer)

14

15

8

16

17

20

26

25

28 (structure of the bis-stearate, n=17, depicted)

27 (structure of the bis-stearate, n=17, depicted)

2

29

25

31 (structure of the bis-stearate, n=17, depicted)

30 (structure of the bis-stearate, n=17, depicted)

37 38 39

41 42

43

(structure of the bis-stearate, n=17, depicted)

44

(structure of the bis-stearate, n=17, depicted)

12

45

46

47

48

49

26

50

51

SYNTHETIC MOLECULES HAVING IMMUNE ACTIVITY

RELATED APPLICATIONS

This application is U.S. National Phase of International Application PCT/NZ2004/000293, filed Nov. 18, 2004 designating the U.S., and published in English as WO 2005/049631 on Jun. 2, 2005, which claims priority to New Zealand Patent Application No. 529603, filed Nov. 18, 2003 and New Zealand Patent Application No. 533245, filed May 31, 2004, all of which are hereby expressly incorporated by reference in their entireties.

FIELD OF INVENTION

The present invention relates to synthetic molecules having biological activity, in particular immune activity including PIM or PIM-like activity, specifically, although by no means exclusively, for use as an immune system modifier.

BACKGROUND

PIM (acyl glyceryl phosphatidylinositol manno-oligosaccharide) is an immunogenic component of mycobacterial cell walls which is capable of treating or preventing inflammatory or immune cell-mediated diseases and disorders such as asthma, allergic rhinitis, dermatitis, psoriasis, inflammatory bowel disease including Crohn's disease and ulcerative colitis, rheumatoid arthritis, multiple sclerosis, diabetes, systemic lupus erythematosis and atherosclerosis.

WO 02/02140 discloses an immunogenic composition comprising PIM which is effective in the treatment and prevention of Th2 mediated disease, particularly asthma. In particular, the PIM vaccine appears to act by suppressing the allergic response which would normally cause a recruitment and activation of eosinphils to the lung causing chronic swelling and inflammation of the airways that affects the breathing of sufferers. Experiments using a mouse model of airway eosinophilia illustrated that administration of the PIM composition resulted in a dose dependent decrease in the number of eosinophils in the lungs of such mice.

Currently a heterogeneous mixture of PIM species is produced by isolating the PIM fraction from dead mycobacterial organisms using a series of chemical purification steps as disclosed in WO 02/02140 and in Severn et al, 1997. This purification process is laborious and not suitable for large scale manufacture of PIM.

In particular, the PIM fraction can be contaminated by lipopolysaccharides such as endotoxins which are also known to induce an immunological response and therefore may mask or interfere with the biological activity of such a PIM extract.

PIM exists in nature in many different forms. For example the number of mannose and acyl residues may vary. Different acyl forms have been purified using sophisticated analytical tools such as MALDI-MS and two-dimensional NMR. (Gilleron et al 2001; Gilleron et al 2003). In particular native $PIM_2$ and $PIM_6$ have been purified, characterised and their biological activity demonstrated in that these compounds stimulate macrophages to produce cytokines.

In addition, a number of glycophospholipid compounds have been synthesised and either polymerised to form synthetic cell membranes, bilayers, films, liposomes for use in drug delivery systems (U.S. Pat. No. 6,071,532; U.S. Pat. No. 6,171,614; JP 06-271597) or used in therapeutic compositions for treating inflammatory disorders (US 2002/0028823; U.S. Pat. No. 6,024,940; US 2002/0032195; US 2003/0008848; US 2003/0022913).

It is an object of the present invention to provide novel synthetic molecules having biological activity, including PIM or PIM-like activity, which may be synthesised using highly efficient and economical chemical processes suitable for manufacture on a large scale and free of endotoxin and/or to provide the public with a useful choice.

SUMMARY OF INVENTION

According to the present invention there is provided a synthetic molecule of formula I:

A-B-E-D (I)

wherein A represents R, or a glyceride group having the formula Ia or Ib:

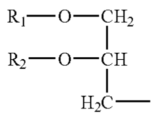

(Ia)

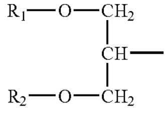

(Ib)

wherein R is H or a linear or branched alkyl of up to 40 carbon atoms, preferably 6-22, more preferably 10-20, and most preferably 16-20 carbon atoms; $R_1$ and $R_2$ are independently H, alkyl or acyl and wherein the alkyl or acyl groups are linear or branched having up to 40 carbon atoms, preferably 6-22, more preferably 10-20, and most preferably 16-20 carbon atoms;

B is selected from the group comprising phosphate, phosphonate, sulfonate, carbamate, and phosphothionate;

E comprises a spacer or linker group providing a linkage between groups B and ID and may be selected from -cyclohexyl-; and $—CHR_3—CHR_4—$ wherein $R_3$ and $R_4$ are independently 11, $CH_2OH$, $CH_2—$, $(CH(OH))_m—CH_2OH$ or $CH((CHOH)_mCH_2OH)—$, and wherein m=1 to 6;

D comprises at least one sugar moiety selected from the group comprising D-mannose, D-galactose, D-glucose, D-glucosamine, N-acetylglucosamine, and 6-deoxy-L-mannose, wherein when D is more than one sugar moiety, the sugar moiety may comprise a single chain of the same or different sugar moieties, or may comprise two or more separate sugar moieties or chains of sugar moieties attached to Eat different sites;

with the proviso that when A is a diacyl or monacyl glyceride, $R_3$ and $R_4$ cannot both be H; and with the proviso that when $R_3$ is H, $R_4$ cannot be $CH_2OH$.

Preferably, D comprises a monosaccharide or oligosaccharide chain of 2 to 12, more preferably 2 to 6, α-1,2 and/or α-1,6 linked sugar moieties which are O-linked to carbon atoms on spacer group E. More preferably, D comprises one or more monosaccharide or oligosaccharide chains of 2 to 6 sugar moieties. One or more of the sugar moieties D may be acylated.

Typically, $R_1$ and $R_2$ are fatty acids independently selected from the group comprising myristate, palmitate, heptadecanoate, stearate, tuberculostearate or linolenate; B is phosphate; E is $—CHR_3CHR_4—$, wherein $R_3$ is $CH_2—$ and $R_4$ is H; and D is at least one sugar moiety comprising D-mannose or oligosaccharide chain of α-1,2 and/or α-1,6-linked mannose residues.

In another embodiment the present invention provides a pharmaceutical composition comprising at least one compound of formula (I) or a pharmaceutically acceptable salt thereof and a pharmaceutically acceptable carrier.

In a further embodiment the present invention provides a use of a compound of formula (I) or a pharmaceutically acceptable salt thereof in the manufacture of a medicament for treating or preventing an inflammatory or immune cell-mediated diseases or disorders, such as asthma, allergic rhinitis, dermatitis, psoriasis, inflammatory bowel disease including Crohn's disease and ulcerative colitis, rheumatoid arthritis, multiple sclerosis, diabetes, systemic lupus erythmatosis and atherosclerosis.

The present invention further provides a use of a compound of formula (I) or a pharmaceutically acceptable salt thereof in the manufacture of an adjuvant for use in enhancing the immune response to an antigen. In addition, the invention provides an adjuvant composition comprising an effective adjuvanting amount of a compound of formula (I) or a pharmaceutically acceptable salt thereof.

In a further embodiment the present invention provides a method of treating or preventing an inflammatory or immune cell-mediated disease or disorder comprising administering an effective amount of a compound of formula (I) or a pharmaceutically acceptable salt thereof to a patient in need thereof. Typically, the patient is a human patient. Typically, the inflammatory or immune cell-mediated disease or disorder is asthma, allergic rhinitis, dermatitis, psoriasis, inflammatory bowel disease including Crohn's disease and ulcerative colitis, rheumatoid arthritis, multiple sclerosis, diabetes, systemic lupus erythmatosis and atherosclerosis.

In a further embodiment the present invention provides a process for preparing synthetic molecules of formula I.

DESCRIPTION OF THE FIGURES

The invention will now be described by reference to the figures of the accompanying drawings in which.

DETAILED DESCRIPTION OF THE INVENTION

Figure 1:
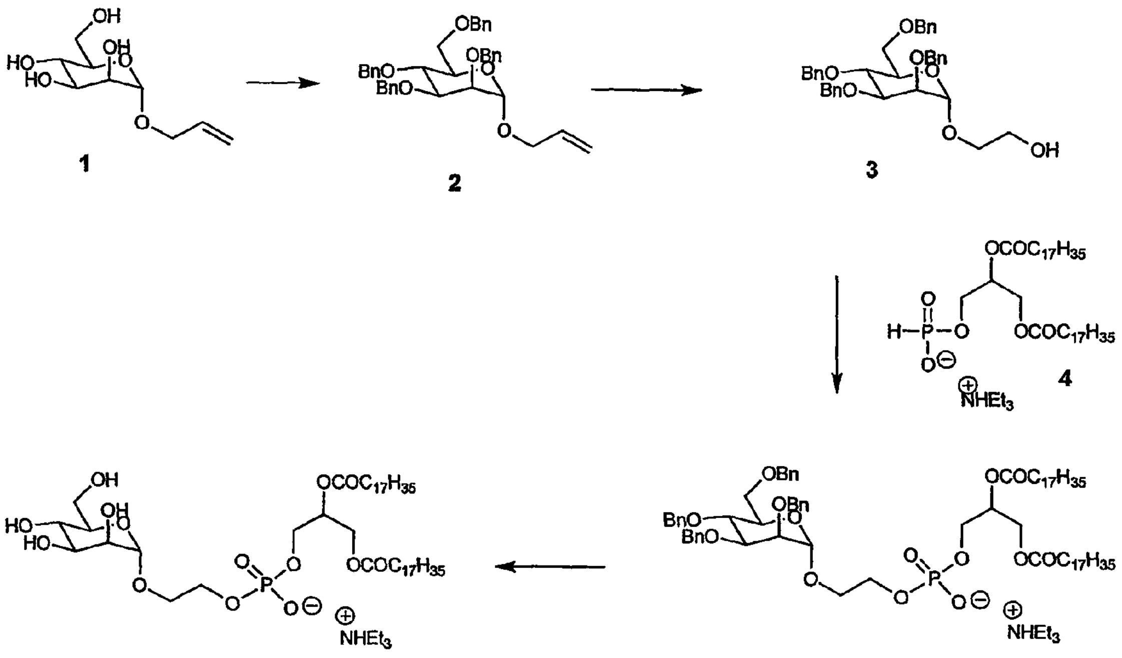
FIG. 1 shows a schematic representation of the synthesis of a compound of the invention named Compound 7.

As broadly outlined above, the present invention is directed to novel synthetic molecules having biological activity, including PIM or PIM-like activity, which are useful in treating an inflammatory or immune cell-mediated disease or disorder in a patient, and in particular in the treatment of asthma in an asthmatic and/or for reducing the risk of developing airway eosinophilia and thus asthma in a non-asthmatic in much the same way as natural PIM has been reported (WO 02/02140). In addition, it is expected that the synthetic molecules of the present invention will be useful in treating allergic, rhinitis, dermatitis, psoriasis, inflammatory bowel disease including Crohn's disease and ulcerative colitis, rheumatoid arthritis, multiple sclerosis, diabetes, systemic lupus erythmatosis and atherosclerosis.

The structure of the natural PIM molecule, isolated, for example, from a mycobacterium is made up of a diacylglycerol unit, a phosphate group, C-2 and C-6 mannopyranose units and an inositol unit as follows:

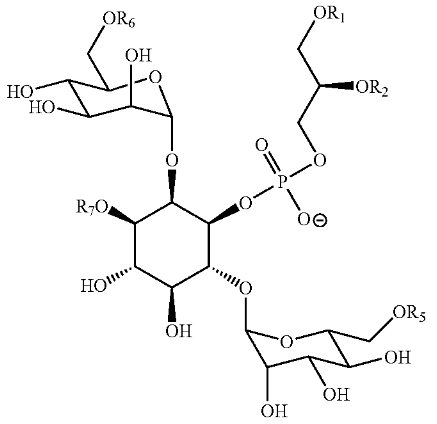

where $R_1$, $R_2$, $R_6$ and $R_7$ are independently either hydrogen or an acyl group selected from palmitate, stearate and tuberculostearate; and $R_5$ is either hydrogen or a monooligosaccharide.

It is not known which part of the natural PIM molecule is responsible for its immunomodulating effects, although a deacylated natural PIM has been shown to be incapable of eliciting an immune response (WO 02/02140).

The present invention provides synthetic molecules which have similar or enhanced immunomodulating activity compared to natural PIM.

The molecules of the present invention may be synthesised using known methods as described in the Examples below. Specifically, the synthetic molecules of the present invention comprise a compound of the formula I:

$$A\text{-}B\text{-}E\text{-}D \qquad (I)$$

wherein A represents R or a glyceride group having the formula Ia or Ib:

(Ia)

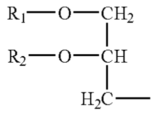

-continued (Ib)

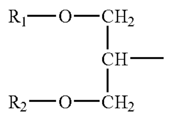

wherein R is H or a linear or branched alkyl of up to 40 carbon atoms preferably 6-22, more preferably 10-20, and most preferably 16-20 carbon atoms; $R_1$ and $R_2$ are independently H, alkyl or acyl and wherein the alkyl or acyl groups are linear or branched having up to 40 carbon atoms, preferably 6-22, more preferably 10-20, and most preferably 16-20 carbon atoms;

B is selected from the group comprising phosphate, phosphonate, sulfonate, carbamate, and phosphothionate;

E comprises a spacer or linker group providing a linkage between groups B and D and may be selected from -cyclohexyl-; and —$CHR_3$—$CHR_4$— wherein $R_3$ and $R_4$ are independently H, $CH_2OH$, $CH_2$— or $(CH(OH))_m$—$CH_2OH$ or $CH((CHOH)_mCH_2OH)$—; wherein n=1 to 40 and m=1 to 6.

D comprises at least one sugar moiety selected from the group comprising D-mannose, D-galactose, D-glucose, D-glucosamine, N-acerylglucosamine and 6-deoxy-L-mannose, wherein when D is more than one sugar moiety, the sugar moiety may comprise a single chain of the same or different sugar moieties, or may comprise two or more separate sugar moieties or chains of sugar moieties attached to E at different sites;

with the proviso that when A is a diacyl or monacyl glyceride, $R_3$ and $R_4$ cannot both be H; and with the proviso that when $R_3$ is H, $R_4$ cannot be $CH_2OH$.

Preferably, D comprises a monosaccharide or an oligosaccharide chain of 2 to 12, more preferably 2 to 6, α-1,2 and/or α-1,6 linked sugar moieties which are O-linked to carbon atoms on spacer group E. More preferably, D comprises one or more monosaccharides or oligosaccharide chains of 2 to 6 sugar moieties. One or more of the sugar moieties of D may be acylated.

Typically, $R_1$ and $R_2$ are fatty acids independently selected from the group comprising myristate, palmitate, heptadecanoate, stearate, tuberculostearate or linolenate; B is phosphate; E is —$CHR_2CHR_4$— where $R_3$ is $CH_2$— and $R_4$ is H; and D is at least one sugar moiety comprising D-mannose or oligosaccharide chain of α-1,2- and/or α-1,6-linked mannose residues.

Compounds where R, $R_1$ and/or $R_2$ comprise long chain acyl or alkyl of up to 60 carbon atoms are contemplated and may be synthesised, although synthesis may be expensive and/or difficult as would be appreciated by a skilled worker. Such long acyl/alkyl chains are known to be immunoreactive (Joyce & Van Kaer, 2003), and would therefore be expected to add to the immunoreactivity of the compounds of general formula I of the present invention.

Definitions

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups.

"Acyl" means an H—CO— or alkyl-CO— group wherein the alkyl group is as herein described.

Spacer or linker group E links together groups B and D of formula I of the present invention. By "spacer or linker group" is meant a group which covalently links a sugar moiety of group D to either a phosphate, phosphonate, carbamate, phosphothionate or sulfonate of group B. The linking group comprises alkyl chains which may be alicyclic, branched and/or further substituted with hydroxyl groups. The spacer/linker may have functionality which allows the attachment of one or more sugar chains. The spacer/linker may have a role of positioning the sugar moeities with respect to the group B phosphate, phosphonate, carbamate, phosphothionate, or sulfonate and the diacyl/dialkyl- or alkyl-acyl-glyceryl unit of group A.

Synthesis of Compounds of the Present Invention

The Synthesis of Compound 7 (Example 1a, FIG. 1)

Compound 7: A=diacylglyceryl unit where the acyl groups are $C_{17}H_{35}CO$— (stearoyl), B=phosphate (as the triethylammonium salt), E=—$(CH_2)_2$—, D=α-D-mannopyranosyloxy (D-mannose)

Allyl α-D-mannopyranoside 1 was benzylated using benzyl bromide and sodium hydride in DMF (Lindhorst et al., 2000) to give the mannoside 2 in 67% yield after purification by silica gel column chromatography. Ozonolysis of 2 and reductive workup with sodium borohydride gave, after purification by silica gel column chromatography, the alcohol 3 in 92% yield. Treatment of 3 with H-phosphonate salt 4, prepared as described by Crossman (Crossman et al., 1997), and subsequent purification gave the triethylammonium salt 6 in a 57% yield. Hydrogenolytic debenzylation of 6 over 10% palladium on carbon in a solvent mixture comprising ethyl acetate, tetrahydrofuran, ethanol and water gave after purification over silica and lyophilization the target, compound 7 in 84% yield.

Figure 2:
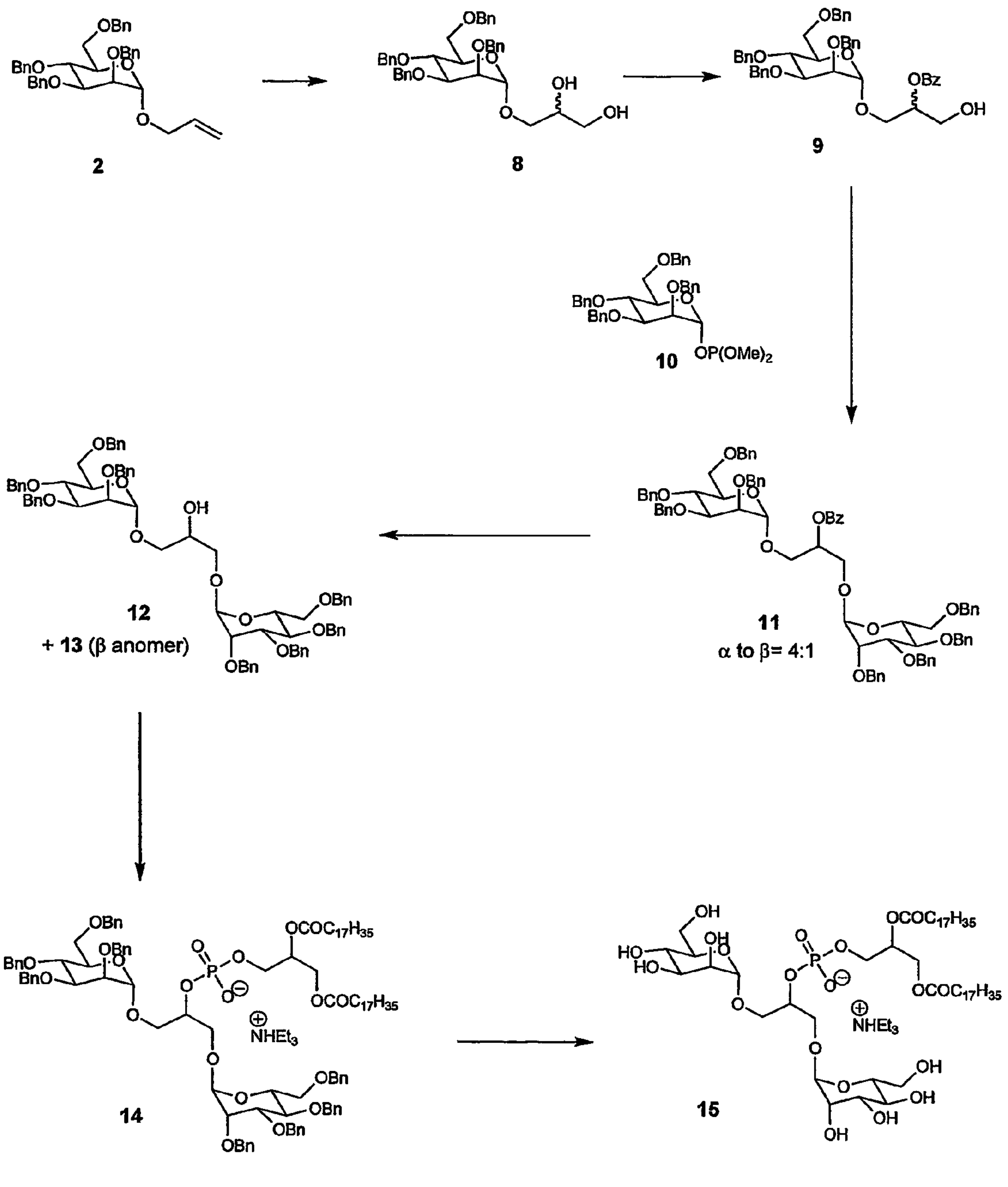
FIG. 2 shows a schematic representation of the synthesis of a compound of the invention named Compound 15.

The Synthesis of Compound 15 (Example 1b, FIG. 2)

Compound 15: A=diacylglyceryl unit where the acyl groups are $C_{17}H_{35}CO$— (stearoyl); B=phosphate (as the triethylammonium salt); E=—$(CH)(CH_2$—$)CH$—; D=2×α-D-mannopyranosyloxy (2×D-mannose residues).

Benzylated allyl mannoside 2 was treated with a catalytic quantity of osmium tetraoxide and the re-oxidant, N-methyl morpholine-1-oxide to give the diol 8 as a 1 to 1 mixture of stereoisomers about the newly formed chiral centre (88% yield). Tritylation of the primary hydroxyl group of 8, subsequent benzoylation (benzoyl chloride and pyridine) and acid promoted detritylation gave benzoate 9 as a mixture of stereoisomers in 77% yield. Mannosylation of the primary hydroxyl group was achieved using phosphite 10 (Watanabe et al., 1993; Watanabe et al., 1994) promoted by N-iodosucinimide and trifluoromethane sulfonic acid in diethyl ether. The dimannoside 11 as a 4:1 mixture of alpha and beta anomers at the new glycosidic linkage was obtained in 71% yield. Debenzoylation using sodium methoxide in methanol allowed isolation of the alpha-dimannoside 12 in 64% yield along with the alpha/beta dimannoside 13 (5%) and a mixture of 12 and 13 (12%). Treatment of 12 with the H-phosphonate salt 4 gave the triethylammonium salt 14 in 76% yield. Removal of the benzyl groups of 14 by catalytic hydrogenation over 10% palladium on carbon in a 2:1:1:1 mixture of ethyl acetate, THF, ethanol and water gave the title compound 15 (69%) as a white solid after lyophilization.

Figure 3:
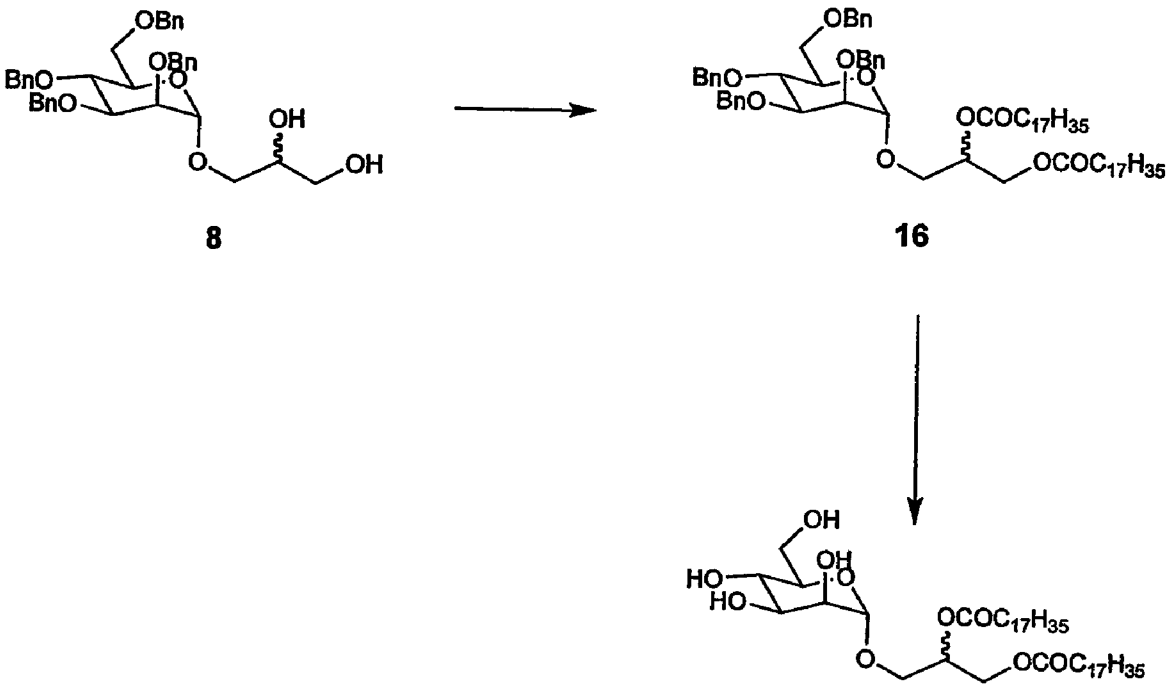
FIG. 3 shows a schematic representation of the synthesis of a comparative compound named Compound 17.

The Synthesis of Compound 17 (Example 1c, FIG. 3)

Compound 17: A=diacylglyceryl unit where the acyl groups are $C_{17}H_{35}CO$— (stearoyl); B has been removed; E has been removed-; D=α-D-mannopyranosyloxy (D-mannose residue). Treatment of glyerol 8 with stearoyl chloride gave the bis-stearate 16 in 84% yield. Hydrogenolysis of 16 gave bis-stearate 17 as a 1:1 mixture of C-2 epimers in 58% yield.

Figure 4:
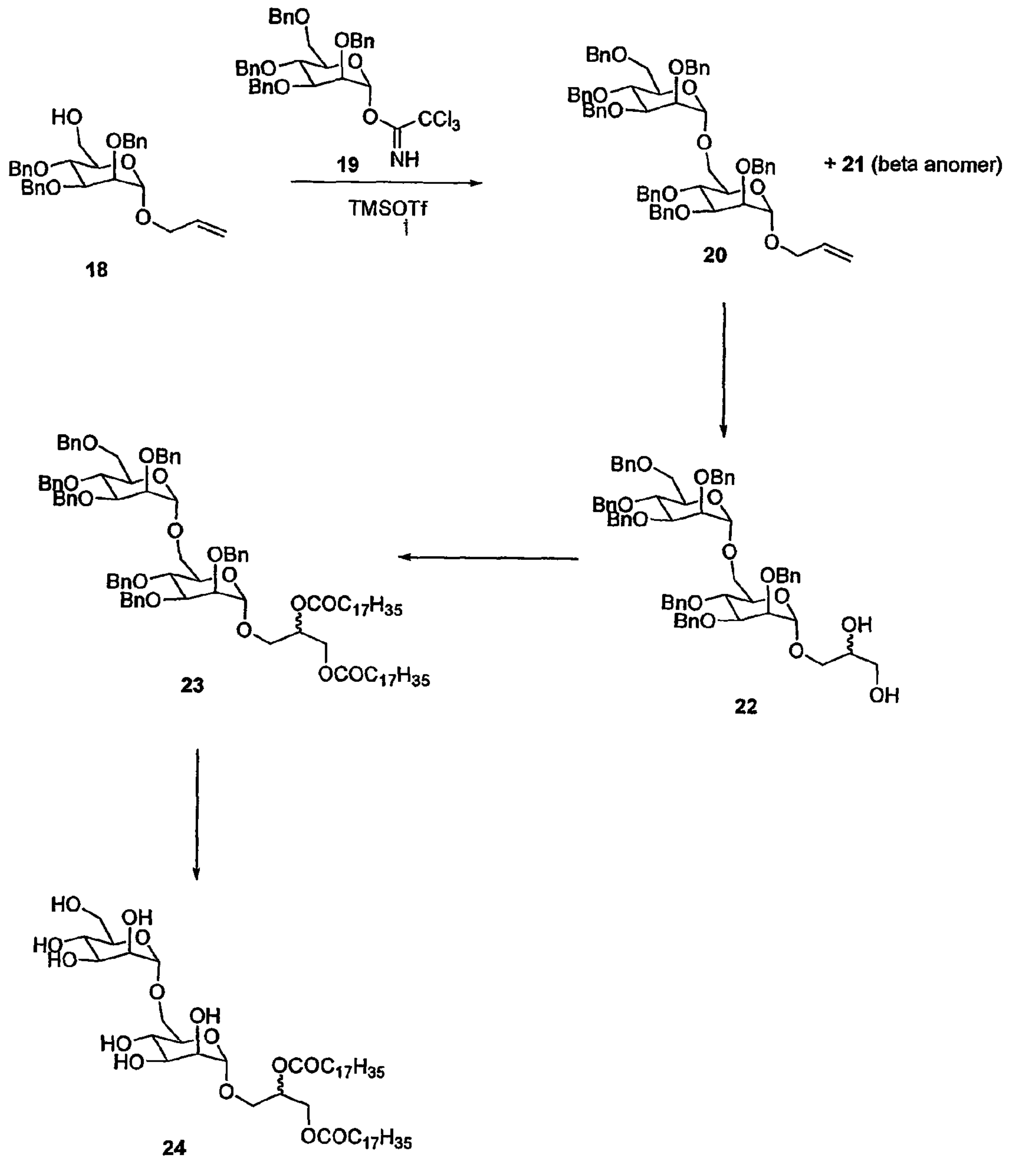
FIG. 4 shows a schematic representation of the synthesis of a comparative compound named Compound 24.

The Synthesis of Compound 24 (Example 1d, FIG. 4)

Compound 24: A=diacylglyceryl unit where the acyl groups are $C_{17}H_{35}CO$— (stearoyl); B has been removed; E has been removed-; D=(1→6)-α-D-mannopyranosyl-α-D-mannopyranosyloxy (1→6 linked-dimannoside).

Mannosylation of the C-6 hydroxyl group of allyl mannoside 18 (Ogawa et al., 1985) was achieved by reaction with 2,3,4,6-tetra-O-benzyl-α-D-mannopyranosyl trichloroimidate 19 promoted by trifluoromethanesulfonic acid to give the α-disaccharide 20 (31%) and the β-disaccharide 21 (10%). Dihydroxylation of the allyl group of 20 was effected by treatment with a catylical quantity of osmium tetraoxide and N-methyl morpholine oxide as the re-oxidant to give glycerol 22 (67%) as a 1:1 mixture of C-2 epimers. Reaction of 22 with stearoyl chloride under standard conditions gave the bis-stearate 23 (84%) which was debenzylated via catalytic hydrogenolysis to give the title compound 24 in a 92% yield.

Figure 5:
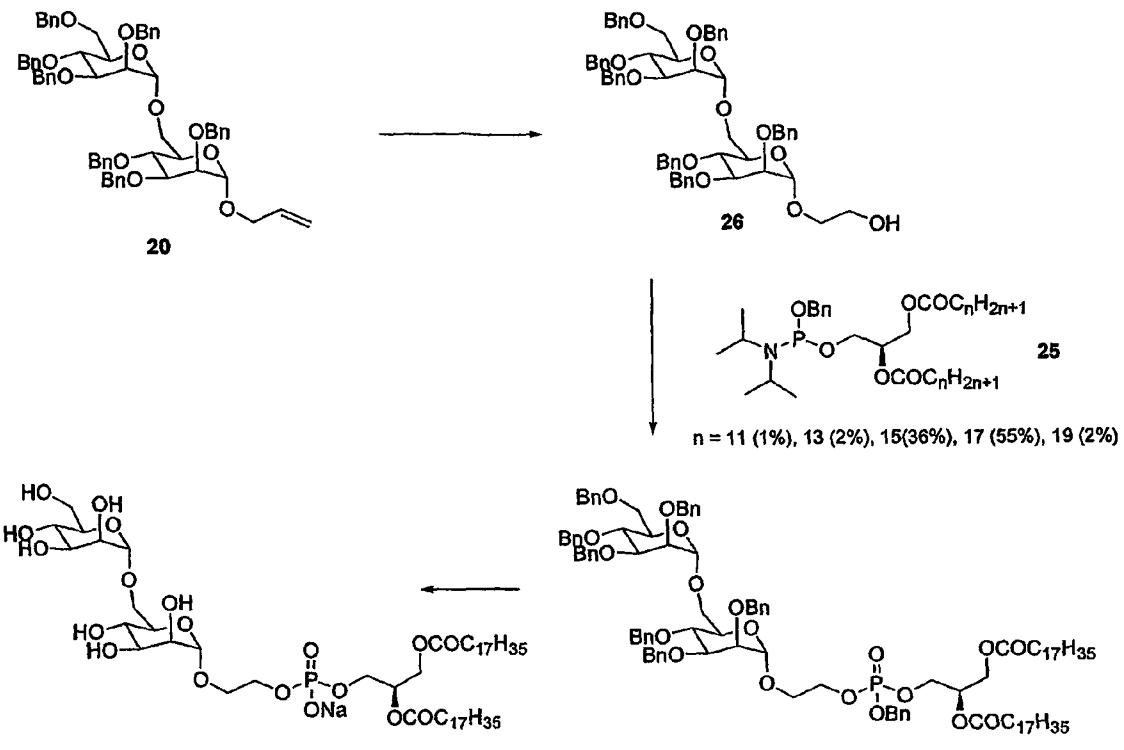
FIG. 5 shows a schematic representation of the synthesis of a compound of the invention named Compound 28.

The Synthesis of Compound 28 (Example 1e, FIG. 5)

Compound 28: A=diacylglyceryl unit where the acyl groups are 55% $C_{17}H_{35}CO$—, 36% $C_{15}H_{31}CO$—, 2% $C_{11}H_{23}CO$—, 1% $C_{20}H_{41}CO$—; B=phosphate (as the sodium salt); E=—$(CH_2)_2$—; D=(1→6)-α-D-mannopyranosyl-α-D-mannopyranosyloxy (1→6 linked-dimannoside).

Allyl mannoside 20 was converted into the substituted glycol 26 in 58% yield by oxidative cleavage of the allyl group with a catalytic amount of osmium tetraoxide and excess sodium periodate, and subsequent reduction of the intermediary aldehyde with sodium borohydride. Phosphorylation of 26 with a mixture of phosphoramidites 25 was achieved using the method of Dreef (Dreef et al, 1991) to give phosphate 27 (61%) as a mixture where the acyl chains are 55% stearoyl ($C_{17}H_{35}CO$), 36% palmitoyl ($C_{15}H_{31}CO$), 2% lauroyl ($C_{11}H_{23}CO$) and 1% decadecanoyl ($C_{20}H_{41}CO$). Removal of the benzyl groups was achieved by hydrogenolysis at 300 psi over palladium on carbon in a mixture of tert-butanol, water and sodium hydrogen carbonate to give, after lyophilization, the title compound 28 (69%) as a white solid.

Figure 6:
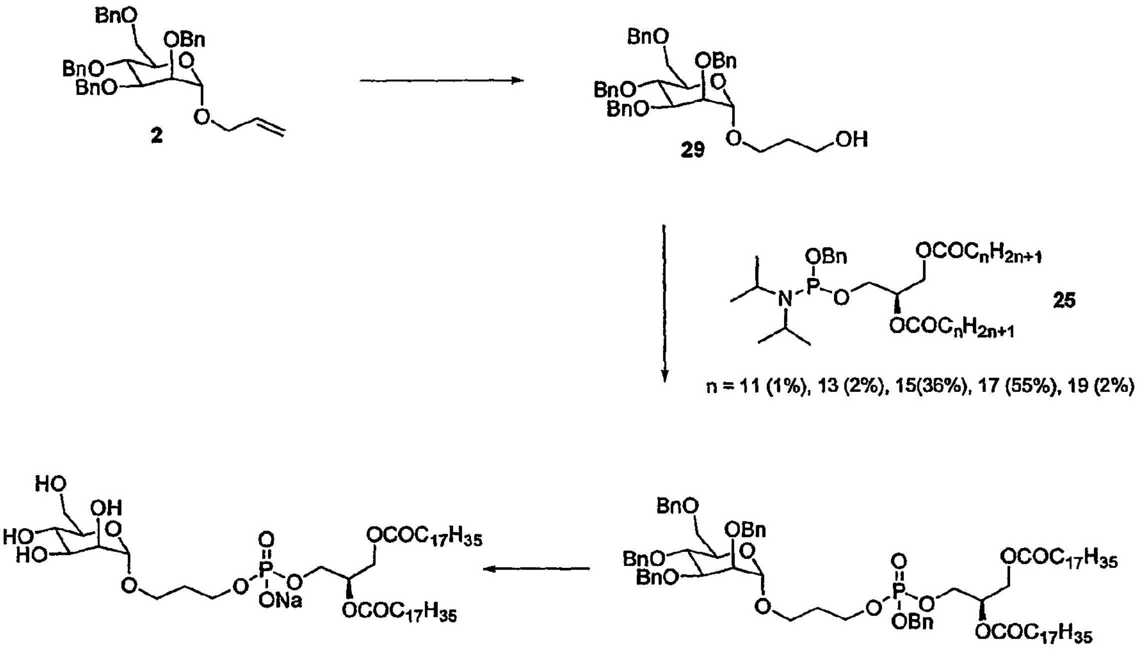
FIG. 6 shows a schematic representation of the synthesis of a compound of the invention named Compound 31.

The Synthesis of Compound 31 (Example 1f, FIG. 6)

Compound 31: A=diacylglyceryl unit where the acyl groups are 55% $C_{17}H_{35}CO$—, 36% $C_{15}H_{31}CO$—, 2% $C_{11}H_{23}CO$—, 1% $C_{20}H_{41}CO$—; B phosphate (as the sodium salt); E=—$(CH_2)_3$—; D=α-D-mannopyranosyloxy (D-mannoside).

Hydroxypropyl mannoside 29 was prepared from allyl mannoside 2 using the procedure of Lindhorst (Lindhorst et al., 2000). Phosphorylation as described for the preparation of 28 gave the phosphate esters 30 (71%, as a mixture where the acyl chains are 55% stearoyl ($C_{17}H_{35}CO$), 36% palmitoyl ($C_{15}H_{31}CO$), 2% lauroyl ($C_{11}H_{23}CO$) and 1% decadecanoyl ($C_{20}H_{41}CO$). Hydrogenolysis of the benzyl groups as described for the preparation of 28 gave the lipid 31 (71%) as a white solid after lyophilization. The product exists as a mixture where the acyl chains are 55% stearoyl ($C_{17}H_{35}CO$), 36% palmitoyl ($C_{15}H_{31}CO$), 2% lauroyl ($C_{11}H_{23}CO$) and 1% decadecanoyl ($C_{20}H_{41}CO$).

Figure 7:
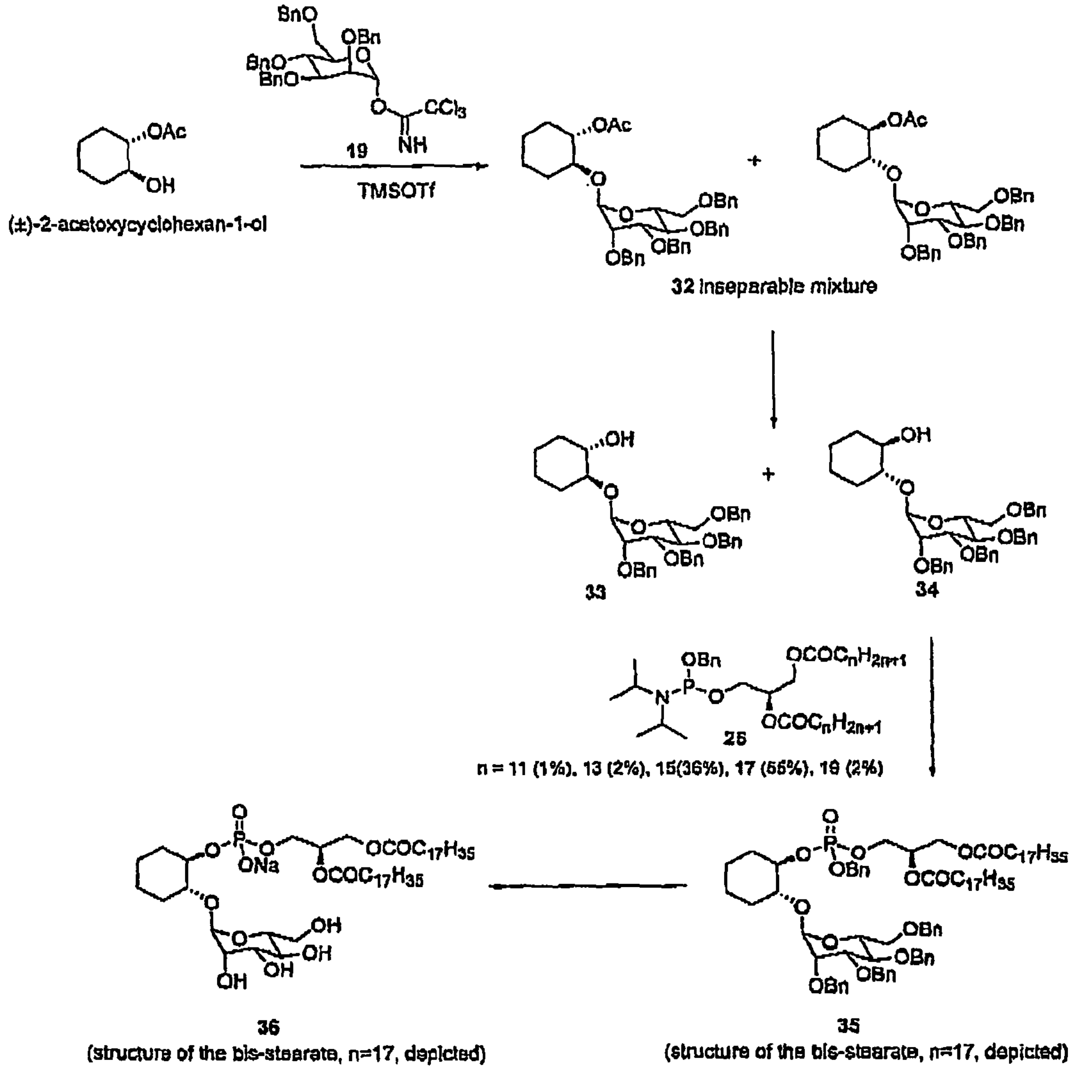
FIG. 7 shows a schematic representation of the synthesis of a compound of the invention named Compound 36.

The Synthesis of Compound 36 (Example 1g, FIG. 7)

Compound 36: A=diacylglyceryl unit where the acyl groups are 55% $C_{17}H_{35}CO$—, 36% $C_{15}H_{31}CO$—, 2% $C_{11}H_{23}CO$—, 1% $C_{20}H_{41}CO$—; B=phosphate (as the sodium salt); E=cyclohexyl; D=α-D-mannopyranosyloxy (D-mannoside).

Mannosylation of (±)-trans-2-acetoxycyclohexan-1-ol (Iranpoor et al., 1996) was effected by treatment with trichloroimidate 19 promoted by trimethylsilyl trifluoromethanesulfonate to give mannosides 32 (61%) as a mixture of stereosiomers. Deacetylation of 32 with basic IRA 401 (OH) in methanol gave (1S,2S) isomer 33 (41%) and (1R,2R)-isomer 34 (35%) of the manosylated cyclohexanediol after separation on silica gel. The configurational assignment are tentative and have been made by comparison of the chemical shifts of H-1 and H-2 in the $^1H$ NMR spectrum to those of the corresponding glucosides (Itano et al., 1980). Phosphorylation of the (1R,2R)-isomer 34 with the phosphoramidites 25 as described previously gave the esters 35 in 36% yield. Hydrogenolysis of the benzyl groups as described for the preparation of 28, purification on silica gel and lyophilization of the product gave the title compound 36 (34%) as a white solid. The product exists as a mixture where the acyl chains are 55% stearoyl ($C_{17}H_{35}CO$), 36% palmitoyl ($C_{15}H_{31}CO$), 2% lauroyl ($C_{11}H_{23}CO$) and 1% decadecanoyl ($C_{20}H_{14}CO$).

Figure 8:
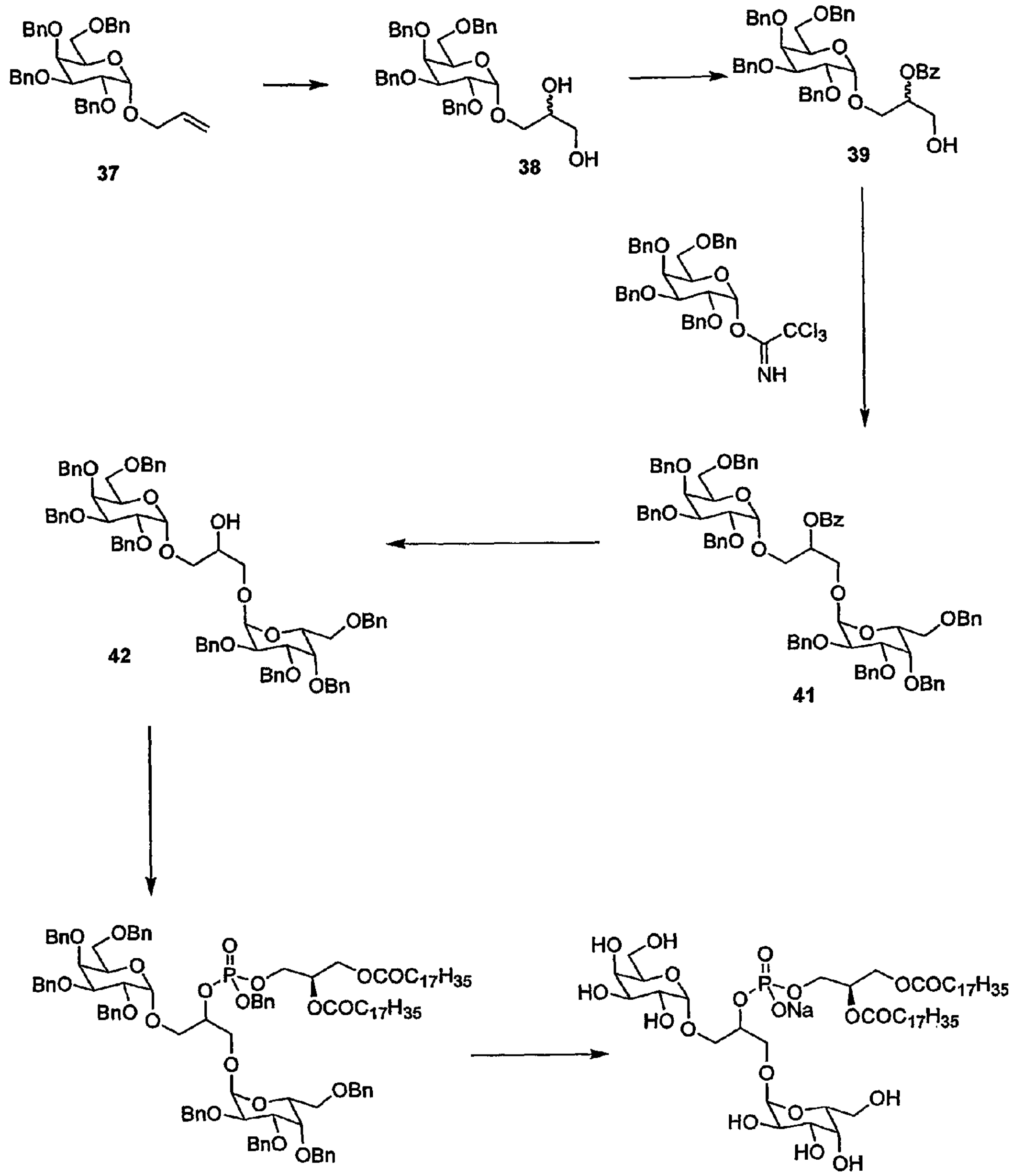
FIG. 8 shows a schematic representation of the synthesis of a compound of the invention named Compound 44.

The Synthesis of Compound 44 (Example 1h, FIG. 8)

Compound 44: A=diacylglyceryl unit where the acyl groups are 55% $C_{17}H_{35}CO$—, 36% $C_{15}H_{31}CO$—, 2% $C_{11}H_{23}CO$—, 1% $C_{20}H_{41}CO$—; B=phosphate (as the sodium salt); E=—(CH)($CH_2$—)$CH_2$—; D=2×α-D-galactopyranosyloxy (2×D-galactoside).

Allyl galactoside 37 (Gigg et al., 1985) was dihydroxylated using catalytic osmium trtaoxide and excess N-methylmorpholine oxide as the reoxidant to give the galactosyl glycerol derivative 38 in 75% yield. Selective benzoylation of the 2° hydroxyl group of 38 was achieved by tritylation of the 1° hydroxyl group eith trityl chloride in pyridine, the subsequent addition of benzoyl chloride and hydrolysis of the trityl group under acidic conditions. This provided the mono-benzoate 41 in 48% yield (as a mixture of C-2 epimers) and a 20% yield of the dibenzoate 40. Galactosylation of 39 with 2,3,4,6-tetra-O-benzyl-α-D-galactopyranosyl trichloroimidate promoted by trimethylsilyl trirluoromethanesulfonate gave, after purification by silica gel column chromatography, the benzoylated bis-galactoside 41 in 61% yield. De benzoylation of 41 was effected by treatment with sodium methoxide to give bis-galactoside 42 in 79% yield. Phosphorylation of 42 using the procedure described for the preparation of 28, gave the protected lipid 43 as a slightly impure syrup. Removal of the benzyl protecting groups was achieved using the method described for the preparation of 28 gave, after purification over silica gel, the target compound 44 (24%) as a white solid after lyophilization. The product exists as a mixture where the acyl chains are 55% stearoyl ($C_{17}H_{35}CO$), 36% palmitoyl ($C_{51}H_{31}CO$), 2% lauroyl ($C_{11}H_{23}CO$) and 1% decadecanoyl ($C_{20}H_{41}CO$).

Figure 9:
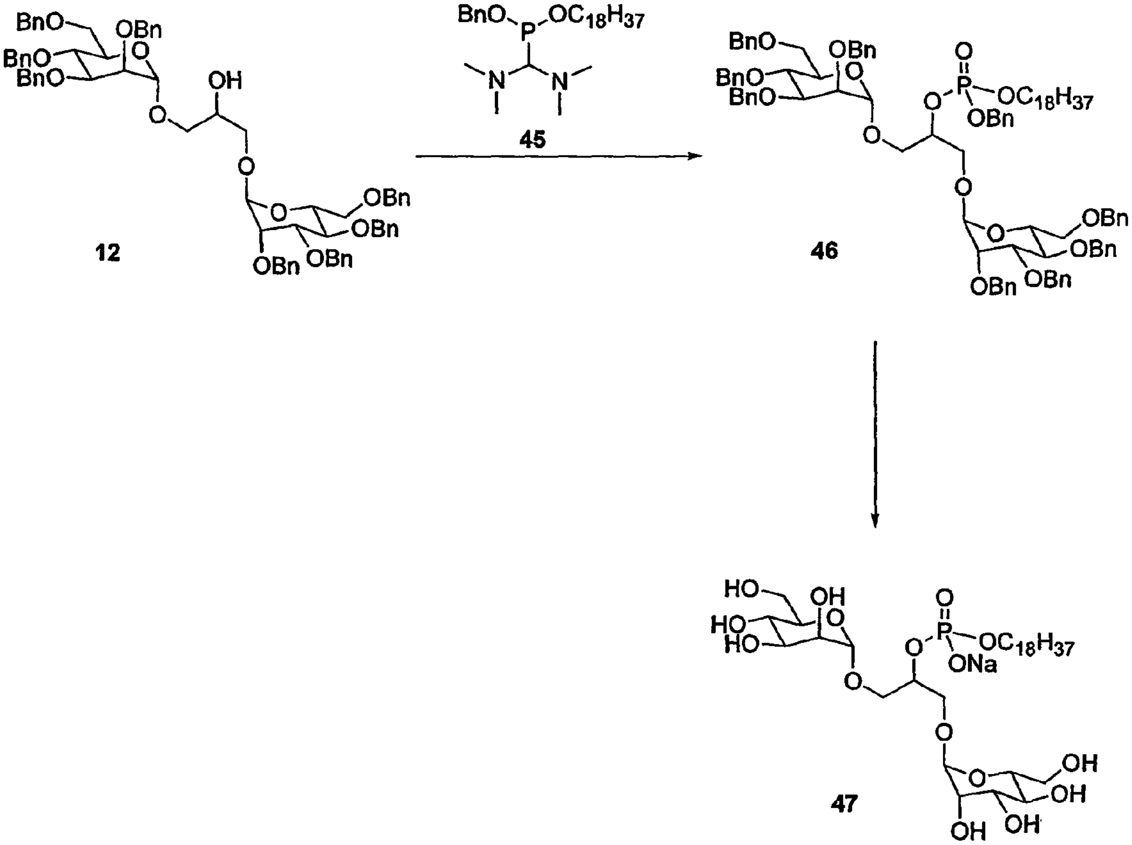
FIG. 9 shows a schematic representation of the synthesis of a compound of the invention named Compound 47.

The Synthesis of Compound 47 (Example 1i, FIG. 9)

Compound 47: A=alkyl unit ($C_{18}H_{37}$); B=phosphate (as the sodium salt); E=—(CH)($CH_2$—)$CH_2$—; D=2×α-D-mannopyranosyloxy (2×D-mannoside).

Bis mannoside 16 was phosphorylated with phosphoramidite 45 under standard conditions to give the protected phosphate ester 46 in 64% yield. Removal of the benzyl groups by catalytic hydrogenation as described for the preparation of 28 gave bis-mannoside 47 in 71% yield.

Figure 10:
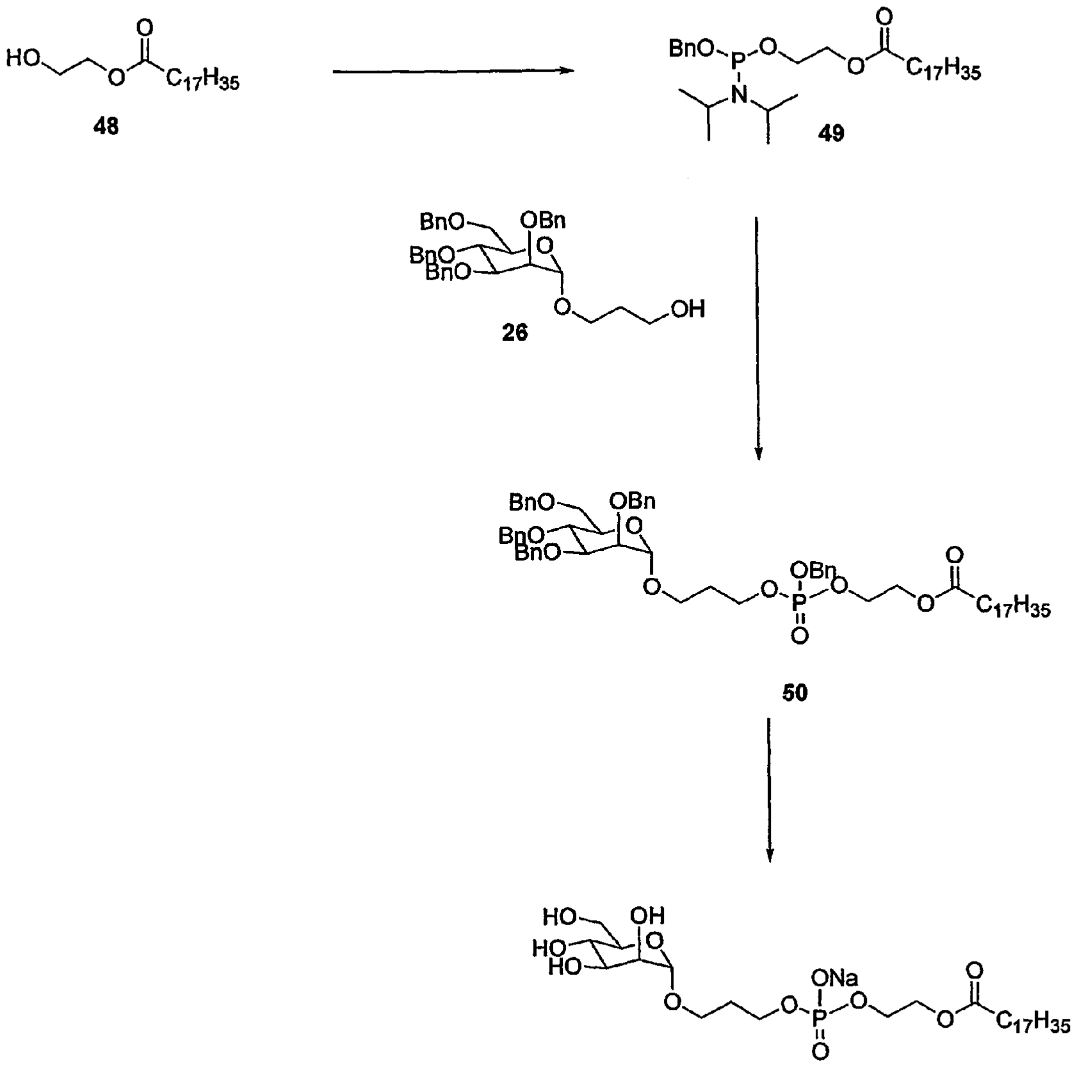
FIG. 10 shows a schematic representation of the synthesis of a compound of the invention named Compound 51.

The Synthesis of Compound 51 (Example 1j, FIG. 10)

Compound 51: A=acyloxyethyl group (acyl=$C_{17}H_{35}$CO—)—; B=phosphate (as the sodium salt); E=—($CH_2$)$_3$-(propyl); D=α-D-mannopyranosyloxy (D-mannoside).

Reaction of mannosyloxy-propanol 29 and phosphoramidite 49 gave, after an oxidative workup, per-benzylated lipid 50. Removal of the benzyl groups using the procedure described in the preparation of 28 gave the target phospholipid 51 in 66% yield.

Further examples satisfying the general structure, A-B-E-D could be synthesised by a skilled worker via modification of the above synthetic procedures.

For example, further compounds may be synthesised where A is either a glyceride of formula Ia where $R_1$ and $R_2$ are different acyl groups or a combination of acyl and alkyl groups. Modification of diacylglyceryl groups is well documented (Hirth & Barner, 1982; Hirth et al., 1983; Lindberg et al., 2002).

Allyl glycosides of carbohydrates other than mannose are documented in the literature. Examples include allyl glycosides of disaccharides containing D-glucose residues (Koizumi et al., 1991; Koto et al., 1992).

Examples of compounds where the spacer is varied may be made from readily available polyols such as cyclohexanediols, erythritol and threoitol.

Compounds where the phosphate is replaced by other moieties may also be synthesised. For example, isocyanates derived from glycerol (A) are available (Green et al., 1987). Reaction of these with a D-E unit where D has a reactive hydroxyl group will give an A-B-E-D unit where B is —NH-COO (ie carbamoyl).

Particularly preferred synthetic molecules of the invention are:

Compound 15

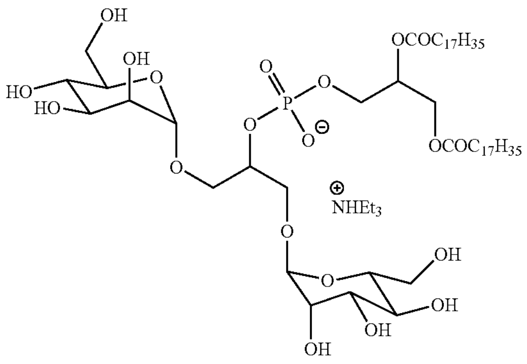

-continued

Compound 7

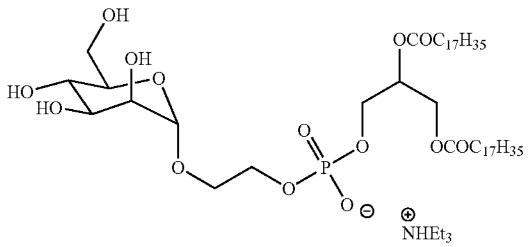

Compound 28

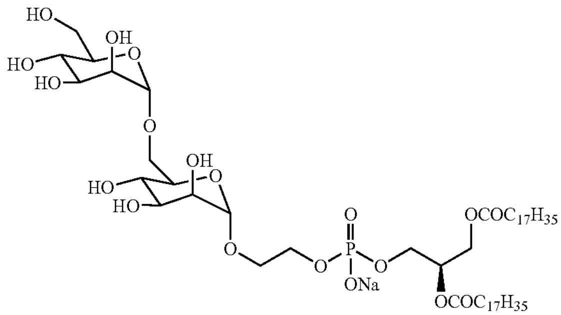

Compound 31

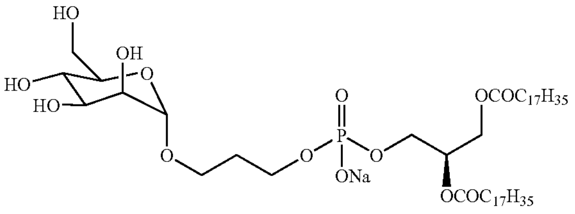

Compound 36

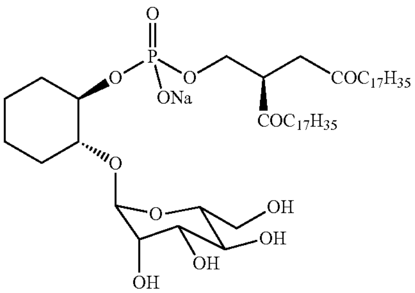

Compound 44

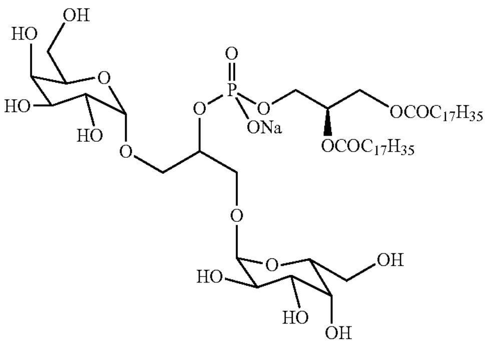

-continued

Compound 47

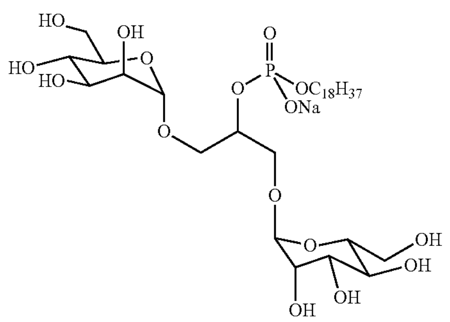

Compound 51

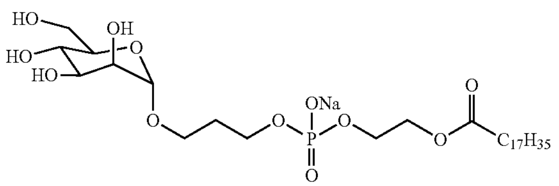

The synthesised molecules are each tested for biological activity in an animal model or in vitro model of disease as discussed below and suitably active compounds formulated into pharmaceutical compositions. The pharmaceutical compositions of the present invention may comprise, in addition to one or more synthetic molecules of the present invention, a pharmaceutically acceptable excipient, carrier, buffer, stabiliser or other material well known in the art. Such materials should be non-toxic and should not interfere with the efficacy of the active ingredient. The precise nature of the carrier or other material will be dependent upon the desired nature of the pharmaceutical composition, and the route of administration e.g. oral, intravenous, cutaneous, subcutaneous, intradermal, nasal, pulmonary, intramuscular or intraperitoneal.

Pharmaceutical compositions for oral administration may be in tablet, lozenge, capsule, powder, granule or liquid form. A tablet or other solid oral dosage form will usually include a solid carrier such as gelatine, starch, mannitol, crystalline cellulose, or other inert materials generally used in pharmaceutical manufacture. Similarly, liquid pharmaceutical compositions such as a syrup or emulsion, will generally include a liquid carrier such as water, petroleum, animal or vegetable oils, mineral oil or synthetic oil.

For intravenous, cutaneous, subcutaneous, intradermal or intraperitoneal injection, the active ingredient will be in the form of a parenterally acceptable aqueous solution which is pyrogen-free and has suitable pH, isotonicity and stability.

For nasal or pulmonary administration, the active ingredients will be in the form of a fine powder or a solution or suspension suitable for inhalation. Alternatively, the active ingredients may be in a form suitable for direct application to the nasal mucosa such as an ointment or cream, nasal spray, nasal drops or an aerosol.

A particularly preferred application of the biologically active compounds of the present invention is in the treatment of rhinitis. Rhinitis is an inflammatory disorder of the nasal passages. The symptoms of rhinitis typically consist of sneezing, rhinorrhea, nasal congestion and increased nasal secretion. Failure of treatment of rhinitis may lead to other disorders that include infection of the sinuses, ears and lower respiratory tract. To date, rhinitis is generally treated by oral medication comprising decongestants and antihistamines or mixtures thereof or by nasal administration of steroids, antihistamines or anti-cholinergics. However, such treatment is associated with various side effects including the sedating side effects of the antihistamines.

The present invention provides an oral pharmaceutical comprising at least one compound of the present invention together with a pharmaceutically acceptable carrier useful for the treatment of rhinitis.

Alternatively, the pharmaceutical composition may be formulated to deliver the active compound of the present invention directly to the mucosa of the nasal passages. The compounds of the present invention are particularly efficacious when delivered to the mucosal membranes due to their polar nature. Indeed, it is considered that the compounds of the present invention may form liposomes thereby providing an inherent delivery mechanism which may account, in part at least, for their potent biological activity (see results below). Preferred direct nasal mucosal delivery formulations include a nasal spray, nasal drops, cream or ointment.

Alternatively, rhinitis may be treated using a pharmaceutical composition of the present invention formulated for injection (either subcutaneous, cutaneous, intradermal, intramuscular or intraperitoneal injection).

For the treatment of asthma or other allergic respiratory disorders, the pharmaceutical compositions of the present invention may be formulated for respiratory administration to deliver the active ingredient to the airways of the patient to be treated. Generally, this will involve oral, intranasal or pulmonary delivery. Often, inhalation by the patient will provide the motive force to deliver the active ingredient. However, respiratory administration can also involve delivery by propellant, including in the form of an aerosol generated using a jet or ultrasonic nebuliser as will be appreciated by a skilled worker.

The ability of the compounds of this invention to treat arthritis can be demonstrated in a murine collagen-induced arthritis model according to the method of Kakimoto, et al., in a rat collagen-induced arthritis model according to the method of Knoerzer et al; in rat adjuvant arthritis model by the method of Halloran, et al., in a rat streptococcal cell wall-induced arthritis model according to the method of Schimmer, et al., or in a SCID-mouse human rheumatoid arthritis model according to the method of Oppenheimer-Marks et al.

The ability of the compounds of this invention to treat Lyme arthritis can be demonstrated according to the method of Gross et al.

The ability of compounds of this invention to treat inflammatory lung injury can be demonstrated in a murine immune complex-induced lung injury model according to the method of Mulligan et al.

The ability of compounds of this invention to treat inflammatory lung disease can be demonstrated in a rabbit chemical-induced colitis model according to the method of Bennet et al.

The ability of compounds of this invention to treat autoimmune diabetes can be demonstrated in an NOD mouse model according to the method of Hasagawa et al., or in a murine streptozotocin-induced diabetes model according to the method of Herrold et al.

In a further embodiment, the invention contemplates the use of one or more additional immuno-responsive compounds co-administered with the pharmaceutical composition of the present invention to give an additive or synergistic effect to the treatment regime. Such an immuno-responsive compound will generally be an immune response inducing substance. Examples of such substance include a natural lipoaribomanan (LAM), a natural or synthetic PIM, or mixtures thereof; glucocorticosteroids, such as prednisolone and methylprednisolone; nonsteroidal anti-inflammatory drugs (NSAIDs); as well as first and second generation anti-TNF$\alpha$ agents. Such substances may be administered either separately, sequentially or simultaneously with at least one compound of the present invention depending upon the condition to be treated as will be appreciated by a stilled worker.

Administration of the pharmaceutical composition of the invention is preferably in a "prophylactically effective amount" or a "therapeutically effective amount", this being sufficient to show benefit to the individual. The actual amount administered, and rate and time-course of administration, will depend on the nature and severity of what is being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, $16^{th}$ edition, Oslo, A. (ed), 1980.

In addition, it is contemplated that the compounds of the present invention may be used as an adjuvant and may be formulated into adjuvant compositions by methods well known in the att.

The present invention is also directed to a process for preparing synthetic molecules of formula (I) comprising the steps (I) modification of a benzylated allyl glycoside compound to form an intermediate by dihydroxylation of the double bond using a catalytic amount of osmium tetraoxide and excess N-methyl morpholine-1-oxide to give a glycosyl glycerol as an intermediate for father modification;

(II) selective benzoylation of the glycosyl glycerol intermediate to form a glycosyl glycerol unit with the 2° hydroxyl group protected as a benzoyl ester;

(III) glycosylation of the 1° hydroxyl group of the intermediate compound and selective removal of the benzoyl protecting group;

(IV) phosphorylation of the 1° or 2° hydroxyl groups of the intermediate compound;

(V) removal of the benzyl protecting groups to form a compound of formula (I).

Alternatively, compounds of formula (I) may be formed by (I) glycosylation of a benzylated mono-acetylated diol followed by deacetylation;

(II) phosphorylation of the 1° or 2° hydroxyl groups of the compound of step (I);

(III) removal of the benzyl protecting groups to form a compound of formula (I);

The invention will now be described in greater detail by reference to specific Examples, which should not be construed as in any way limiting the scope of the invention.

EXAMPLES

Reagents and Solvents

The following chemicals were purchased and used without further purification:

Laboratory grade solvents were used in this work. Dichloromethane was distilled from $P_2O_5$, THF from sodium wire (with benzophenone) and hexane was distilled using $CaCl_2$. All other reagents were purified according to the methods given in 'Purification of Laboratory Chemicals', $2^{nd}$ ed. Perrin, D. D., Amarego, W. F. L. and Perrin, D. R., Peragamon Press Ltd, Oxford England (1981).

Salisyl chlorophosphite, (S)-(+)-1,3-dioxolane-4-methanol used for the synthesis of 1,2-sn-di-O-stearoyl glycerol, and D-(+)-mannose and methyl $\alpha$-D-mannopyranoside used for the preparation of mannosyl donors, were purchased from the Aldrich Chemical company. 10% Palladium on carbon (Pd/C) was purchased from BDH.

Thin layer chromatography (TLC) was performed using aluminium-backed Merck Sorbent silica gel. Compounds were detected under an ultraviolet lamp and/or with a stain consisting of 5% w/v dodecamolybdophosphic acid in ethanol, followed by development with a heat gun. Column chromatography was performed using silica gel (Sorbasil, particle size 32-63 μm), which was packed by the slurry method.

Instrumentation:

Nuclear Magnetic Resonance (NMR) Spectroscopy $^1H$ NMR spectra were recorded at either 300 MHz on a Varian Unity Inova 300 MHz spectrometer or at 500 MHz on a Varian Unity Inova 500 MHz spectrometer. All spectra were recorded in the stated solvent at 25° C. in 5 mm NMR tubes. Chemical shifts are reported relative to $CHCl_3$ at 7.26 ppm using the 8 scale. Chemical shifts have an uncertainty of ±0.01 ppm. Coupling constants (J) have been rounded to the nearest 0.5 Hz. Resonances were assigned as follows: chemical shift (number of protons, multiplicity, coupling constant(s), assigned proton(s)). Multiplicity abbreviations are reported by the conventions: s (singlet), d (doublet), dd (doublet of doublets), t (triplet), m (multiplet).

$^{13}C$ NMR spectra were recorded at either 75 MHz on a Varian Unity Inova 300 MHz spectrometer or at 125 MHz on a Varian Unity Inova 500 MHz spectrometer. Chemical shifts of carbon nuclei are reported relative to $CDCl_3$ at 70.08 ppm.

$^{31}P$ NMR spectra were recorded at either 131 MHz on a Varian Unity Inova 300 MHz spectrometer or at 202 MHz on a Varian Unity Inova 500 MHz spectrometer. Chemical shifts of phosphorous nuclei are reported relative to 80% $H_3PO_4$ as an external standard at 0.0 ppm.

Infrared (IR) Spectroscopy

Infrared spectra were recorded on a Perkins Elmer 1600 series FTIR spectrophotometer. Samples were examined as thin films between two NaCl plates.

Microanalyses

Microanalyses were carried out by the Campbell Microanalytical Laboratory, University of Otago, Dunedin, New Zealand.

Mass Spectroscopy (MS)

Low resolution mass spectra were run on a Shimadzu QP8000 alpha with APCI or ESI probes. ESI spectra were run using 9:1 acetonitrile/water mobile phase, CDL temperature of 250° C. and a cone voltage of 50 eV. APCI spectra were run using 1:1 methanol/water mobile phase, CDL temperature of 250° C., APCI temperature of 400° C. and a cone voltage of 50 eV. High resolution mass spectra were run in the ESI/mode on MicroMass LCT coupled to a Waters 2790 LC with a 996 PDA, source 80° C. probe temperature as required for solvent scanning 2500-100AMU at 1/sec with a Cole Palmer syringe pump for direct infusion work at the Department of Chemistry, University of Canterbury, New Zealand.

Polarimetry

Optical rotations were recorded on a Jasco DIP-100 digital polarimeter using a 1 dm cell.

Chromatography

Thin layer chromatography (TLC) was performed using aluminium-backed Merck Sorbent silica gel. Compounds were detected under an ultraviolet lamp and/or with a stain consisting of 5% w/v dodecamolybdophosphic acid in ethanol, followed by development with a heat gun.

Column chromatography was performed using silica gel (Sorbasil, particle size 32-63 μm), which was packed by the slurry method.

Example 1

Synthesis of Compounds Corresponding to General Formula (I)

Example 1(a)

Synthesis of triethylammonium 1-O-(1,2-distearoyl-sn-glycero-3-phosphoryl)-2-O-(α-D-mannopyranosyl)-1,2-ethanediol 7 (Compound 7)

The total synthesis of Compound 7 is represented schematically in FIG. 1.

Synthesis of Allyl 2,3,4,6-tetra-O-benzyl-α-D-mannopyranoside 2 (Lindhurst et al; 2000)

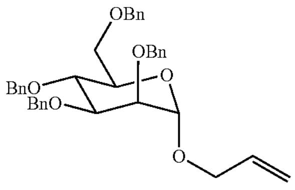

Allyl α-D-mannopyranoside 1 (Gigg et al., 1985; Rajan-Babu et al., 1989) (1.50 g, 2.78 mmol) was suspended in benzyl chloride (40 mL) and sodium hydride (60%, 2.1 g, 52.5 mmol) was carefully added. The suspension was stirred at 125° C. for 6 h under nitrogen. The mixture was filtered and excess benzyl chloride was distilled off under reduced pressure. The residue was dissolved in dichloromethane (100 mL), washed with water (300 mL) and dried ($MgSO_4$). After removal of the solvent the residue was purified over silica (hexane/ether 4:1 as eluent) to give the title compound 2 (3.2 g, 67%) as pale yellow syrup; $[\alpha]_D^{21.5}$ +25.0 (c 1.5, $CH_2Cl_2$); $^1$H NMR (500 MHz, $CDCl_3$) δ 7.40-7.25 and 7.18-7.13 (m, 20H, Ar—H), 5.88-5.79 (m, 1H, H-2), 5.21 (ddd, 1H, J 17, 3, 1.5 Hz, H-3a), 5.18 (ddd, 1H, J 10.5, 3, 1 Hz, H-3b), 4.92 (d, 1H, J 2 Hz, H-1'), 4.88 (d, 1H, J 10.5 Hz, $PhCH_2$), 4.75 (d, 1H, J 12.5 Hz, $PhCH_2$), 4.71 (d, 1H, J 12.0 Hz, $PhCH_2$), 4.67 (d, 1H, J 12.0 Hz, $PhCH_2$), 4.63 (s, 2H, $PhCH_2$), 4.55 (d, 1H, J 12 Hz, $PhCH_2$), 4.50 (d, 1H, J 10.5 Hz, $PhCH_2$), 4.16 (ddt, 1H, J 13.5, 4.5, 1.5 Hz, H-1'a), 4.02-3.92 (m, 3H), 3.83-3.71 (m, 4H); $^{13}$C NMR (125 MHz, $CDCl_3$) δ 138.6, 138.5, 138.5, 138.4 (ipso-C), 133.9 (C2'), 128.4, 128.4, 128.3, 128.1, 127.9, 127.8, 127.7, 127.64, 127.62, 127.59, 127.5 (CH—Ar), 117.3 (C3'), 97.2 (C1', $^1J_{C-H}$ 169 Hz), 80.3 (C1'), 75.2, 75.0, 74.7, 73.4, 72.6, 72.2, 72.0, 69.3, 67.9; LRMS-ESI (+ve ion) m/z (%) 604 $[MNa+1]^+$ (71), 603 $[MNa]^+$ (100).

Synthesis of 2-O-(2,3,4,6-tetra-O-benzyl-α-D-mannopyranosyl)-1,2-ethandiol 3

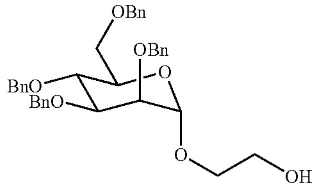
3

Ozone gas was bubbled through a solution of allyl 2,3,4,6-tetra-O-benzyl-α-D-mannopyranoside 2 (1.0 g, 1.72 mmol) in methanol (100 mL) at −78° C. until a slight blue colour persisted (2-3 minutes). The reaction was warmed to room temperature, sodium borohydride (460 mg, 12.1 mmol) was added and the mixture was stirred for one hour. The solvent was distilled off and the residue was treated with 2M HCl (30 mL). The compound was then extracted in dichloromethane, dried over magnesium sulfate and solvent removed in vacuo. The residue was purified over silica (hexane/ether, 2:3 as eluent) to give the title compound 3 (916 mg, 92%) as colourless syrup; Rf 0.4 (ether/hexane, 3:2); $[\alpha]_D^{21.5}$ +14.7 (c 2.85, $CH_2Cl_2$); (Found: C, 73.84; H, 6.97. $C_{36}H_{40}O_7$ requires C, 73.95; H, 6.97); $^1$H NMR (500 MHz, $CDCl_3$) δ 7.37-7.26 and 7.16-7.14 (m, 20 Hs, Ar—H), 4.92 (d, 1H, J 2 Hz, H-1'), 4.90 (d, 1H, J 11 Hz, $PhCH_2$), 4.78 (d, 1H, J 11 Hz, $PhCH_2$), 4.74 (d, 1H, J 11 Hz, $PhCH_2$), 4.66 (s, 2H, $PhCH_2$), 4.64 (d, 1H, J 11.5 Hz, $PhCH_2$), 4.57 (d, 1H, J 11.5 Hz, $PhCH_2$), 4.52 (d, 1H, J 11 Hz, $PhCH_2$), 3.96-3.84 (m, 5H), 3.75-3.63 (m, 5H); $^{13}$C NMR (125 MHz, $CDCl_3$) δ 138.6, 138.4, 138.4, 138.2 (ipso-C), 128.5, 128.46, 128.1, 127.9, 127.8, 127.75, 127.7 (CH—Ar), 98.9 (C-1'), 80.1 (CH), 75.2 (CH $CH_2$), 75.0 (CH), 73.5 ($CH_2$), 72.9 ($CH_2$), 72.4 ($CH_2$), 72.2 (CH), 70.9 ($CH_2$), 69.4 ($CH_2$), 62.1 ($CH_2$); LRMS-ESI (+ve ion) m/z (%) 607-$[MNa]^+$ (100).

Synthesis of 1,2-Di-O-stearoyl-sn-glycero-3-H-phosphonate triethylammonium salt 4 (Crossman et al., 1997)

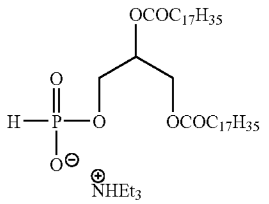
4

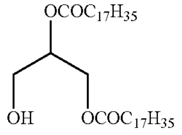
5

1,2-Di-O-stearoyl-sn-glycerol 5 (150 mg, 0.24 mmol) prepared by the method of Hirth (Hirth & Barner, 1982) was dried by evaporation from pyridine and was dissolved in pyridine/THF (2 mL, 1:4). The solution was then added dropwise to the stirred solution of salicyl chlorophosphite (80 mg, 0.396 mmol) in THF (2 mL). The reaction was stirred at room temperature for 15 minutes and 1M aqueous triethylammonium bromide (TEAB) solution (10 mL) was added followed by the addition of chloroform (10 mL). The organic layer was washed with water (25 mL), 1M TEAB (20 mL) and dried over magnesium sulfate. Removal of the solvent gave salt 4 which was used without further purification in the following reaction.

Synthesis of Triethylammonium 1-O-(1,2-di-O-stearoyl-sn-glycero-3-phoshoryl)-2-O-(2,3,4,6-tetra-O-benzyl-α-D-mannopyranosyl)-1,2-ethanediol 6

6

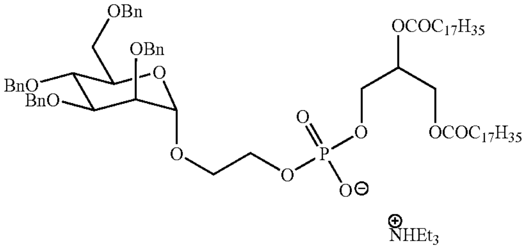

Salt 4 and mannopyranoside 3 (102 mg, 0.18 mmol) were dried by co-evaporation with pyridine (2×20 mL). The mixture was dissolved in pyridine (40 mL), pivaloyl chloride (196 μL, 1.59 mmol) was added and the reaction mixture was stirred for 1 h at room temperature. A solution of iodine (132 mg, 0.52 mmol) in a 9:1 mixture of pyridine/water (10 mL) was added and stirring was continued for 45 min. The reaction mixture was diluted with dichloromethane (50 mL), washed with 10% sodium thiosulfate solution (20 mL), with 1M TEAB (2×20 mL) and water (100 mL). The organic layer was dried over magnesium sulfate and the solvent was removed. The residue was purified over silica (dichloromethane/methanol/TEA 97:2:1 as eluent) to give the title compound 6 (176 mg, 57%) as clear glass; Rf 0.45 (methanol/ether/dichloromethane, 1:2:7); $[\alpha]_D^{21.5}$ +7.3 (c 0.3, $CH_2Cl_2$); $^1$H NMR (500 MHz, $CDCl_3$) δ 7.38-7.23 and 7.15-7.14 (m, 20H, Ar—H), 5.24-5.18 (m, 1H, H-2"), 4.96 (d, 1H, J 2.5 Hz, H-1'), 4.86 (d, 1H, J 11 Hz, $PhCH_2$), 4.73 (s, 2H, $PhCH_2$), 4.72 (d, 1H, J 12.5 Hz, $PhCH_2$), 4.67 (d, 1H, J 12 Hz, $PhCH_2$), 4.60 (d, 2H, J 3.0 Hz, $PhCH_2$), 4.51 (t, 2H, J 14.5 Hz), 4.40-4.36 (m, 1H), 4.18-4.14 (m, 1H), 4.03-3.95 (m, 5H), 3.92-3.87 (m, 1H), 3.87-3.86 (m, 1H), 3.82-3.70 (m, 3H), 3.64-3.62 (m, 1H), 2.84 (q, 6H, J 7.0 Hz, $3\times NCH_2$), 2.25 (t, 4H, J 8.0 Hz, $2\times COCH_2$), 1.58-1.54 br (m, 4H), 1.30-1.11 br (m, 65H), 0.88 (t, 6H, J 10.5 Hz, $2\times CH_3$); $^{13}$C NMR (125 MHz, $CDCl_3$) δ 173.7, 173.3, 138.92, 138.87, 138.74, 138.71 (ipso-C), 128.55, 128.52, 128.48, 128.27, 128.04, 127.99, 127.75, 127.72, 127.68 (CH—Ar), 98.3 (C-1'), 80.6, 75.3, 75.1, 74.9, 73.6, 72.8, 72.2, 72.1, 70.7, 69.5, 67.4, 64.5, 63.0, 45.9, 34.6, 34.4, 32.2, 30.0, 29.9, 29.8, 29.62, 29.60, 29.58, 29.41, 29.39, 25.2, 25.1, 22.9, 14.4, 9.7; $^{31}$P NMR (202 MHz, $CDCl_3$) δ 0.607 ppm; LRMS-ESI (−ve ion) m/z (%) 1270(100), 1269 (87); HRMS-ESI (−ve) (Found: m/z 1269.7978 $(M-NHEt_3)^-$. $C_{75}H_{114}O_{14}P^-$ requires m/z 1269.7946).

Synthesis of Triethylammonium 1-O-(1,2-di-O-stearoyl-sn-glycero-3-phosphoryl)-2-O-(α-D-mannopyranosyl)-1,2-ethanediol 7 (Compound 7)

7

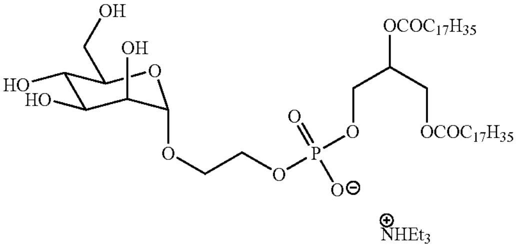

Phosphate 6 (60 mg, 0.047 mmol) was dissolved in a 2:1:1:1 mixture of EtOAc/THF/EtOH/$H_2O$ (20 mL). 10% Pd/C (120 mg, BDH) was added and the reaction was stirred under an atmosphere of hydrogen for 18 h. After filtration through Celite, the filter pad was washed with THF (5 mL) and dichloromethane (2×5 mL) and the solvent was removed. Water was removed by azetropic distillation with toluene (5×3 mL). The residue was purified over silica (dichloromethane/methanol/TEA 94:5:1 as eluent) to give, after lyophilization from methanol and water, the title compound 7 (36 mg, 84%) as a white solid; Rf 0.2 (dicholoromethane:methanol/TEA 9:1:1); $[\alpha]_D^{21.5}$ +10 (c 0.9, $CH_2Cl_2$); $^1$H NMR (500 MHz, $CDCl_3$) δ 5.22 br (m, 1H, H—C2"), 4.92 br (1H, H-1), 4.38 br (d, 1H, J 2.5 Hz, H-3"), 4.16 (dd, J 2.5, 1.15 Hz, H-1" and 3"), 4.08-3.58 (m, 12H), 3.73 br (s, 6H, $3\times NCH_2$), 2.34-2.26 (m, 4H, $2\times COCH_2$), 1.60-1.50 br (m, 4H), 1.19-1.29 br (m, 65H), 0.90 (t, 6H, J 10.5 Hz, $2\times CH_3$); $^{13}$C NMR (125 MHz, $CDCl_3$) δ 173.5, 173.2, 100.2 (C-1), 72.7, 71.7, 70.8, 70.5, 70.4, 67.9, 67.0, 65.0, 63.6, 62.7, 62.1, 45.8, 34.4, 34.2, 32.0, 29.8, 29.7, 29.6, 29.43, 29.41, 29.24, 29.23, 25.0, 24.95, 22.8, 14.2, 8.9; $^{31}$P NMR (202 MHz, $CDCl_3$) δ −0.229 ppm; LRMS-ESI ve) m/z (%) 910(100), 909 (60); HRMS-ESI (−ve) (Found: m/z 909.6078 $(M-NHEt_3)^-$. $C_{47}H_{90}O_{14}P^-$ requires m/z 909.6068).

Example 1(b)

Synthesis of triethylammonium (1,2-di-O-stearoyl-sn-glycero-3-phosphoryl)-2-[1,3-bis-O-(α-D-mannopyranosyl)]glycerol 15 (Compound 15)

The total synthesis of compound 15 is represented schematically in FIG. 2.

Synthesis of 1-O-(2,3,4,6-Tetra-O-benzyl-α-D-mannopyranosyl)glycerol 8

8

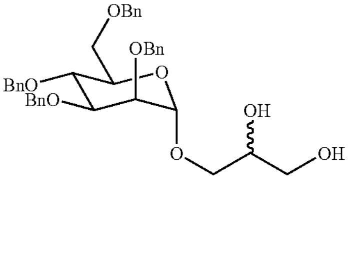

Allyl 2,3,4,6-tetra-O-benzyl-α-D-mannopyranoside 2 (1.00 g, 1.72 mmol) and N-methylmorpholine-1-oxide (302 mg, 2.58 mmol) were dissolved in a mixture of acetone/water 9:1 (40 mL) and a 1% aqueous osmium tetraoxide solution (1.5 mL) was added. The reaction mixture was stirred overnight at room temperature, then poured into 10% sodium thiosulfate solution (20 mL) and extracted with dichloromethane (40 mL). The organic layer was washed with water and dried over magnesium sulfate. The solvent was removed and the residue was purified over silica (hexane/ether 1:2 as eluent) to give the title compound 8 (927 mg, 88%, 1:1 mixture of epimers) as a colourless syrup; Rf 0.4 (hexanes/ethylacetate, 1:2); (Found: C, 71.69; H, 6.92. $C_{37}H_{42}O_8.0.5H_2O$ requires C, 71.25; H, 6.95; O, 21.80); $\nu_{max}$/cm$^{-1}$ 3439 (OH); $^1$H NMR (500 MHz, $CDCl_3$) δ 7.36-7.24 and 7.21-7.18 (m, 20H, Ar—H), 4.87-4.71 (d, 1H, J 12.5 Hz, $PhCH_2$), 4.64-4.59 (m, 1H), 4.55 and 4.53 (2×d, 1H, J 12.5 Hz, $PhCH_2$), 4.49 (dd, 1H, J 11 and 4.5 Hz, $PhCH_2$), 3.94-3.46 (m, 11H); $^{13}$C NMR (125 MHz, $CDCl_3$) δ 138.4, 138.3, 138.24, 138.23, 138.1, 138.0 (ipso-C), 128.45, 128.43, 128.40, 128.10, 128.06, 127.99, 127.95, 127.90, 127.76, 127.72, 127.70, 99.1 (C-1'), 79.9, 75.12, 75.10, 75.04, 75.02, 74.9, 73.6, 73.5, 72.9, 72.85, 72.42, 72.37, 72.3, 72.2, 70.9, 70.8, 70.6, 69.9, 69.5, 69.4, 63.6, 63.5; LRMS-ESI (+ve) m/z (%) 638 [MNa+1]$^+$ (24), 91 (100).

Synthesis of 2-O-Benzoyl-3-O-(2,3,4,6-tetra-O-benzyl-α-D-mannopyranosyl)glycerol 9

9

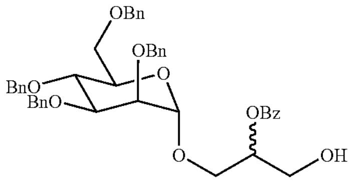

Glycerol 8 (900 mg, 1.47 mmol) and trityl chloride (490 mg, 1.76 mmol) were dissolved in dry pyridine (60 mL) and heated at 100° C. The disappearance of 8 was monitored by TLC and after 90 min the reaction was cooled to 0° C. and a solution of benzoyl chloride (1.0 g, 7.0 mmol) in dry dichloromethane (10 mL) was added. The reaction was warmed to room temperature and stirring was continued for 2 h. The solvent was removed and the residue was dissolved in chloroform (50 mL), washed with 2M HCl (2×20 mL), saturated sodium bicarbonate solution (2×20 mL), water (25 mL) and dried over magnesium sulfate. The solvent was removed, the residue was dissolved in mixture of dichloromethane and methanol (7:3, 50 mL) and p-TSA (75 mg) was added. The reaction was stirred at room temperature overnight and solvent was removed. The residue was purified over silica [hexane/ether, 8:2 to 7:3 as eluent] to afford the title compound 9 (816 mg, 77%) as a pale syrup; Rf 0.4 (ether/hexane, 2:1); $^1$H NMR (500 MHz, $CDCl_3$) δ 8.05 br (d, 3H, J 7.5 Hz), 7.51 (t, 2H, J.5 Hz), 7.41-7.12 and 7.18-7.10 (m, 20 Hs, Ar—H), 5.30-5.20 (m, 1H, H-2'), 4.94 and 4.89 (2×d, each 1H, J 2 Hz, H-1), 4.85 and 4.83 (2×d, each 1H, J 10.5 Hz, $PhCH_2$), 4.77-4.46 (m, 7H), 4.05-3.62 (m, 10H); $^{13}$C NMR (125 MHz, $CDCl_3$) δ 166.1, 166.0 (CO), 138.3, 138.2, 138.1, 138.05 (ipso-C), 133.0, 132.96, 129.8, 129.7, 129.6, 129.5, 128.3, 128.2, 128.2, 128.13, 128.10, 128.07, 127.83, 127.80, 127.74, 127.65, 127.62, 127.59, 127.56, 127.41, 127.38, 127.36, 127.32 (CH—Ar), 98.0 and 97.5 (C-1), 79.7, 79.6, 74.8, 74.7, 74.6, 73.8, 73.4, 73.2, 73.1, 72.4, 72.0, 71.9, 69.0, 68.9, 65.6, 65.3, 65.25, 61.2, 57.9; $\nu_{max}$/cm$^{-1}$ ($CHCl_3$) 1716; LRMS-ESI (+ve) m/z 742 [MNa]$^+$ (100); HRMS-ESI (+ve) (Found: m/z 719.3220 ($MH^+$). $C_{44}H_{47}O_9$ requires m/z 719.3220).

Synthesis of (2,3,4,6-Tetra-O-benzyl-D-mannopyranosyl)dimethylphosphite 10 (Watanabe et al. 1993; Watanabe et al., 1994)

10

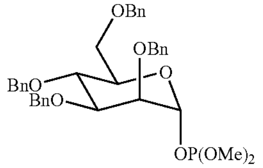

A mixture of 2,3,4,6-tetra-O-benzyl-D-mannose (Koto et al., 1976) (940 mg, 1.74 mmol), dimethoxy-N,N-diisopropylphosphoromidate (437 mg, 2.27 mmol) and 4,5-dichloroimidazole (355 mg, 2.61 mmol) in dry dichloromethane (25 mL), under nitrogen, was stirred at room temperature for 105 min. The mixture was poured into water (100 mL) and extracted with dichloromethane. The organic layer was washed with water, dried over magnesium sulfate and the solvent was removed. The residue consisting mainly of phosphite 10 was used without further purification.

Synthesis of 2-O-Benzoyl-1,3-bis-O-(2,3,4,6-tetra-O-benzyl-α-D-mannopyranosyl)glycerol 11

11

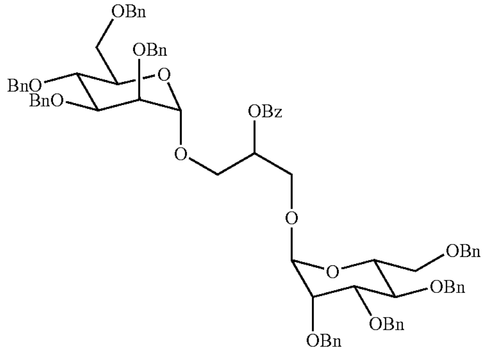

Powdered 4 Å molecular sieves (50 mg) were added to a solution of glycerol 9 (730 mg, 1.02 mmol), phosphite 10 (771 mg, 1.22 mmol) and N-iodosuccinimide (NIS) (275 mg, 1.22 mmol) in dry ether (20 mL) under an atmosphere of nitrogen. The reaction was stirred at room temperature for 15 minutes, trifluoromethanesulfonic acid (110 μL, 1.24 mmol) was added and the stirring was continued for 2 h. The reaction was diluted with more ether (50 mL) and the organic layer was washed with 10% sodium thiosulfate solution (30 mL), water (2×20 mL) and dried over magnesium sulfate. The solvent was removed and the residue was purified over silica [hexane/ether 9:1 as eluent] to give 11 (900 mg, 71%, α to β 4:1) as a colourless syrup; Rf 0.6 (hexane/ether, 2:3); $\nu_{max}$cm$^{-1}$/($CHCl_3$) 1716.7; $^1$H NMR (500 MHz, $CDCl_3$) δ inter alia 8.00 (d, J 7.7, 2H), 7.55 (t, J 7.7 Hz, 1H), 7.38-7.08

(m, 40H, Ar—H), 5.53-5.41 and 5.38-4.43 (m, together 1H, H-2'), 4.96 (d, 1H, J 2 Hz, H-1), 4.91 (d, 1H, J 2 Hz, H-1), 4.86 (d, 2H, J 11 Hz, $PhCH_2$), 4.82 (d, 2H, J 11 Hz, $PhCH_2$), 4.72 (d, 2H, J 12.5 Hz, $PhCH_2$), 4.69 (d, 2H, J 12.5 Hz, $PhCH_2$), 4.65-4.55 (m, 4H), 4.52-4.42 (m, 4H), 4.13-3.50 (m, 16H); $^{13}C$ NMR (125 MHz, $CDCl_3$) 8 inter alia 165.9 (CO), 138.6, 138.5, 138.5, 138.43, 138.42, 138.35 (ipso-C), 133.2 ($C_q$-benzoyl), 130.0, 129.8, 128.5, 128.41, 128.35, 128.33, 128.29, 128.03, 127.92, 127.87, 127.81, 127.78, 127.76, 127.73, 127.63, 127.60, 127.52, 98.4 and 97.7 (2×C-1), 80.0, 79.9, 75.1, 75.0, 74.9, 74.8, 74.7, 73.42, 73.38, 72.68, 72.65, 72.4, 72.3, 72.2, 71.4, 69.2, 69.1, 65.9, 65.5; LRMS-ESI (+ve) m/z (%) 1265 $[MNa+1]^+$ (18), 1264 ($MNa^+$,47), 91 (100); HRMS-ESI (+ve) (Found: m/z 1241.5595 ($MH^+$). $C_{78}H_{81}O_{14}$ requires m/z 1241.5626).

Synthesis of 1,3-Bis-O-(2,3,4,6-tetra-O-benzyl-α-D-mannopyranosyl)glycerol 12

12

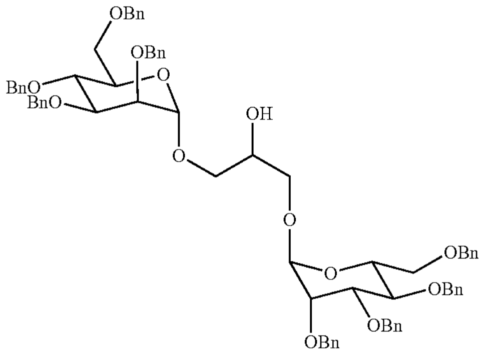

13

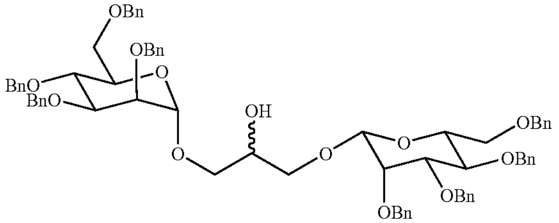

Dimannoside 11 (800 mg, 0.65 mmol) was dissolved in 1M sodium methoxide in methanol (80 mL) and the reaction was stirred overnight at room temperature. The solvent was removed and the residue was dissolved in dichloromethane, washed with 2M HCl (2×50 mL) and water (50 mL), and dried over magnesium sulfate. Removal of the solvent gave a residue (a to β 4:1, 615 mg) which was purified over silica [hexane/ether 75:25 to 65:35 gradient elution] to afford the title compound 12 (470 mg, 64%), a mixture of 12 and 13 (90 mg, 12%), and 13 (40 mg, 5%).

Data for 12: Rf 0.55 (hexane/ether, 2:3); $[\alpha]_D^{21.5}$ +24 (c 1.05, $CH_2Cl_2$); $\nu_{max}cm^{-1}/(CHCl_3)$ 3018 br (OH); $^1H$ NMR (500 MHz, $CDCl_3$) δ 7.35-7.20 and 7.15-7.12 (m, 40H, Ar—H), 4.85-4.82 (m, 4H), 4.71 (d, 2H, J 12.5 Hz, $PhCH_2$), 4.67 (d, 2H, J 12.5 Hz, $PhCH_2$), 4.62-4.55 (m, 6H), 4.49-4.45 (m, 4H), 3.96 (d, 1H, J 10 Hz), 3.91 (d, 1H, J 10 Hz), 3.77-3.65 (m, 8H), 3.60-3.48 (m, 6H), 3.44-3.39 (m, 1H); $^{13}C$ NMR (125 MHz, $CDCl_3$) δ 138.52, 138.45, 138.43, 138.34, 138.29 (ipso-C), 128.42, 128.41, 128.40, 128.38, 128.36, 128.05, 127.84, 127.83, 127.72, 127.69, 127.67, 127.64, 127.59, 127.56 (CH—Ar), 98.55 and 98.58 (both C-1, $^1JC$-H 170 Hz), 80.1, 80.0, 75.1, 75.08, 74.91, 74.77, 73.44, 73.42, 72.76, 72.37, 72.33, 72.26, 72.24, 70.0, 69.6, 69.4, 69.24, 69.21; LRMS-ESI (+ve) 1177 $[MK+1]^+$ (59), 1176 $[MK]^+$ (78), 1161 $[MNa+1]^+$ (97), 1160 $[MNa]^+$ (100); HRMS-ESI (+ve) (Found: m/z 1159.5200 ($MNa^+$). $C_{71}H_{76}O_{13}Na^+$ requires m/z 1159.5184).

Data for 13: Rf 0.5 (hexane/ether, 2:3); $\nu_{max}cm^{-1}/(CHCl_3)$ 3012 br (OH); $^1H$ NMR (500 MHz, $CDCl_3$) δ 7.34-7.16 m, 40H, Ar—H), 5.04 (d, 1H, J 2 Hz, H-1a), 4.92-4.83 (m, 2H), 4.76-4.44 (m, 15H), 4.00-3.64 (m, 16H), 3.58-3.42 (m, 1H); $^{13}C$ NMR (125 MHz, $CDCl_3$) δ 138.53, 138.50, 138.42, 138.36, 138.30, 138.26, 138.23 (ipso-C), 128.40, 128.37, 128.22, 128.18, 128.14, 128.08, 128.06, 127.97, 127.92, 127.84, 127.76, 127.69, 127.66, 127.59, 127.55, 98.6 and 97.7 (both C-1), 80.14, 79.95, 75.17, 75.11, 74.96, 74.92, 74.88, 73.46, 72.78, 72.71, 72.40, 72.38, 72.36, 72.23, 69.29, 67.03, 61.69; LRMS-ESI (+ve) mnlz 1177 $[MK+1]^+$ (35), 1176 $[MK]^+$ (100), 1160 $[MNa]^+$ (89); (Found: C, 74.87; H, 6.86; $C_{71}H_{76}O_{13}$ requires C, 74.98; H, 6.74).

Synthesis of Triethylammonium 2-O-(1,2-di-O-stearoyl-sn-glycero-3-phosphoryl-1,3-bis-O-(2,3,4,6-tetra-O-benzyl-α-D-mannopyranosyl)glycerol 14

14

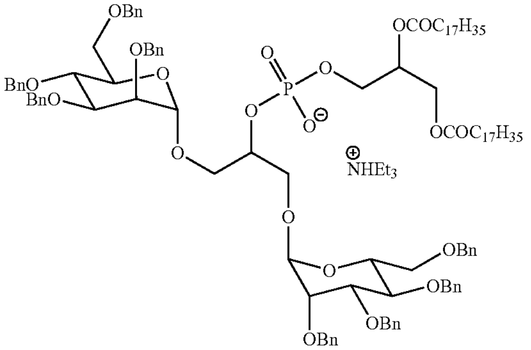

A mixture of salt 4, prepared from 5 (200 mg, 0.32 mmol), salicyl chlorophosphite (107 mg, 0.53 mmol) using the procedure previously described, and glycerol 12 (200 mg, 0.176 mmol) was dried by co-evaporation with pyridine (2×20 mL) and was then dissolved in pyridine (8 mL). Pivaloyl chloride (200 μL, 1.62 mmol) was added and the resulting solution was stirred for 1 h at room temperature. After this time a solution of iodine (120 mg, 0.47 mmol) in a 9:1 mixture of pyridine/water (30 mL) was added and stirring was continued for 45 min. The reaction mixture was diluted with dichloromethane (50 mL) and stirred for 15 min, washed with 10% sodium thiosulfate solution (20 mL), and with 1M TEAB (2×20 mL) and water (100 mL). The organic layer was dried over magnesium sulfate and the solvent was removed. The residue was purified over silica (dichloromethane/methanol/TEA 98:1:1 as eluent) to give the title compound 14 (252 mg, 76%) as clear glass; Rf 0.45 (dichloromethane/methanol/TEA, 5:1:0.1); $[\alpha]_D^{22.1}$ +11.7 (c 1.2, $CH_2Cl_2$). $^1H$ NMR (500 Mz, $CDCl_3$) δ 7.38-7.11 (m, 40H, Ar—H), 5.22-5.18 (m, 1H, H-1'), 5.03 (d, 1H, J 6 Hz, H-1), 4.96 br (s, 1H, H-1), 4.86-4.80 (m, 2H, $PhCH_2$), 4.74-4.25 (m, 15H, $PhCH_2$), 4.15-4.10 (m, 1H), 4.06-3.92 (m, 5H), 3.90-3.62 (m, 14H), 2.90-2.80 br (m, 6H, $3\times NCH_2$), 2.21 (t, 4H, J 7.5 Hz, $2\times COCH_2$), 1.58-1.44 br (m, 4H, $2\times COCH_2CH_2$), 1.32-1.20 (m, 48H), 1.15 (t, 9H, J 7.5 Hz, $3\times NCH_2CH_3$), 0.88 (t, 6H, J 7.5 Hz, $2\times CH_3$);

$^{13}C$ NMR (125 MHz, $CDCl_3$) δ 173.40, 172.99 (CO), 138.76, 138.74, 138.66, 138.58 (ipso-C), 128.35, 128.27, 128.24, 128.22, 128.04, 128.03, 127.80, 127.74, 127.71, 127.67, 127.65, 127.60, 127.58, 127.45, 127.38 (CH—Ar), 98.29 (C-1'), 80.47, 80.39, 75.08, 75.04, 74.80, 74.75, 73.37, 73.33, 72.83, 72.54, 72.08, 72.02, 70.52, 69.32, 69.21, 66.97, 63.58, 62.95, 45.43, 34.29, 34.11, 31.96, 29.75, 29.70, 29.57, 29.40, 29.37, 29.20, 24.96, 24.89, 22.73, 14.16, 8.71; $^{31}P$ NMR (121 MHz, $CDCl_3$) δ 0.15 ppm; LRMS-ESI (−ve) m/z (%) 1824 (38), 1823 (90), 1822 (100); HRMS-ESI (−ve) (Found: m/z 1823.0492 $(M\text{-}NHEt_3)^-$; $C_{116}H_{166}NO_{20}P$ requires m/z 1823.0526.

Synthesis of Triethylammonium 2-O-(1,2-O-distearoyl-sn-glycero-3-phoshoryl)-1,3-bis-O-(α-D-mannopyranosyl)glycerol 15 (Compound 15)

15

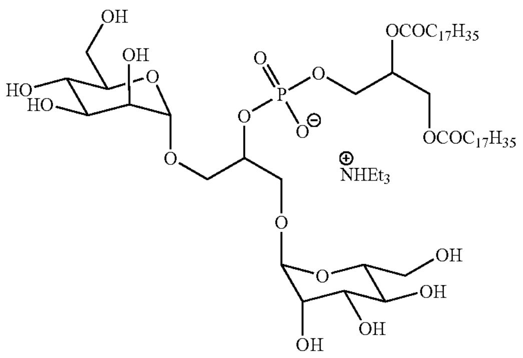

Phosphate 14 (100 mg, 0.055 mmol) was dissolved in a 2:1:1:1 mixture of EtOAc/THF/EtOH/$H_2O$ (30 mL). 10% Pd/C (200 mg) was added and the reaction was stirred under the atmosphere of hydrogen for 18 h. The mixture was filtered through Celite, the filter pad was washed with THF (5 mL), methanol (5 mL) and dichloromethane (2×5 mL), and the solvent from the combined filtrates was removed in vacuo. The water was removed by azeotropic distillation with toluene (5×4 mL). The residue was purified by silica gel preparative plate chromatography (dichloromethane/methanol/TEA 94:5:1 as eluent). The baseline region of the plate was cut and the silica washed with warm methanol (20 mL) and dichloromethane (20 mL). The solvent was removed to give a residue which was lypophilised from a methanol and water mixture to give the title compound 15 (42 mg, 69%) as a white solid; $[\alpha]_D^{22.1}$ +31 (c 0.3, $CH_2Cl_2$); $^1H$ NMR (500 MHz, $CDCl_3/CD_3OD/D_2O$ 35:20:3) δ 5.10-4.90 (m, 1H, H-2"), 4.59 (dd, 1H, J 4 and 2 Hz, H-1), 4.56 br (s, 1H, H-1), 4.82-3.76 (m, 9H), 3.74-3.69 (m, 2H), 3.63-3.57 (m, 4H), 3.57-3.32 (m, 6H), 2.87 (q, 6H, J 7.5 Hz, $3\times NCH_2$), 2.10-2.04 (m, 4H, $2\times COCH_2$), 1.42-1.25 br (m, 4H, $2\times COCH_2CH_2$), 1.15-0.95 br (m, 65H), 0.63 (t, 6H, J 7 Hz, $2\times CH_3$); $^{13}C$ NMR (125 MHz, $CDCl_3/CD_3OD/D_2O$ 35:20:3) δ 173.9, 173.5 (CO), 100.0, 99.9, 90.5, 72.7, 72.6, 70.8, 70.1, 67.03, 66.98, 66.4, 66.0, 63.1, 62.5, 61.1, 58.6, 48.6, 48.4, 48.3, 48.1, 47.9, 47.8, 47.6, 46.0, 33.9, 33.7, 31.5, 29.3, 29.24, 29.19, 29.15, 29.00, 28.95, 28.77, 28.74, 24.6, 24.5, 22.3, 13.5, 8.1; $^{31}P$ NMR (121 Mz, $CDCl_3/CD_3OD/D_2O$ 35:20:3) δ −0.05 ppm; LRMS-ESI (−ve) m/z 1102(80), 1101 (69); HRMS-ESI (−ve) (Found: m/z 1101.6702 $(M\text{-}NHEt_3)^-$; $C_{60}H_{118}NO_{20}P$ requires m/z 1101.6679).

Example 1(c)

Synthesis of Compound 17

The total synthesis of compound 17 is represented schematically in FIG. 3.

Preparation of Di-stearate 16

16

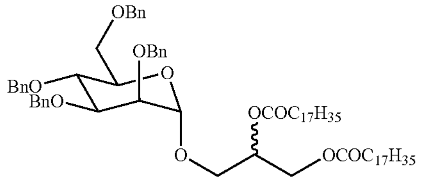

A mixture of the diol 8 (127 mg, 0.21 mmol), stearoyl chloride (152 mg, 0.50 mmol) and pyridine (80 μl, 1.00 mmol) in dry dichloromethane (10 ml) was stirred at ambient temperature for 17 h. The mixture was diluted with dichloromethane, washed with 10% hydrochloric acid solution, saturated sodium bicarbonate solution, brine then dried over magnesium sulfate. Removal of the solvent and purification of the residue by silica gel column chromatography gave a 1:1 mixture of the stereoisomeric diglycerides 16 (200 mg, 84%) as a waxy white solid. $^1H$ NMR (300 MHz, $CDCl_3$) δ inter alia 7.40-7,15 (m, 20H), 5.24-5.12 (m, 1H), 2.26-2.22 (m, 4H), 1.65-1.52 (m, 4H), 1.39-1.19 (m, 56H), 0.88 (t, 6H, J 7 Hz, $2\times CH_3$).

Preparation of 1,2-di-O-stearoyl-3-O-α-D-mannopyranosylglycerol 17 (Compound 17)

17

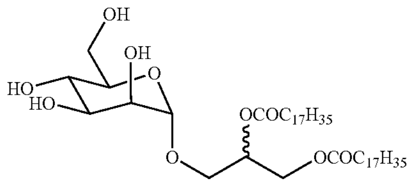

A mixture of the glyceride 16 (121 mg, 0.105 mmol) and 10% palladium on carbon (50 mg) in ethanol (25 ml) was stirred under an atmosphere of hydrogen 20 h. The mixture was filtered through a pad of Celite and the filter cake was washed with a mixture of methanol and dichloromethane. The solvent was removed from the filtrate to give a white solid (93 mg) which was subjected to silica gel column chromatography ($CH_2Cl_2$/MeOH 95:5 to 90:10 gradient elution) to give a 1:1 mixture of the steroisomeric diacyl glycerides 17 (48 mg, 58%) as a white amorphous solid. $^1H$ NMR (500 MHz, $CDCl_3$) δ inter alia 5.19 br (s, 1H, H-2), 4.82 br (s, 1H, H-1'), 4.37-4.25 (m, 1H), 4.17-4.08 (m, 1H), 4.00-3.40 (m, 8H), 2.35-2.25 (m, 4H), 1.62-1.55 (m, 4H), 1.40-1.18 (m, 56H), 0.87 (t, 1H, J=7 Hz, $2\times CH_3$); $^{13}C$ NMR (125 MHz, $CDCl_3$) δ 173.68, 173.35, 173.30, 100.43, 100.16, 72.76, 371.45, 70.74, 70.70, 69.76, 69.59, 66.06, 65.80, 65.80, 65.64, 63.63, 62.55, 69.94, 34.31, 34.15, 31.98, 29.77, 29.72, 29.59, 29.42, 29.38, 29.22, 29.18, 24.98, 24.93; (Found: C, 68.67; H, 11.15. $C_{45}H_{86}O_{10}$ requires C, 68.66; H, 11.01%).

Example 1(d)

Synthesis of Compound 24

The total synthesis of compound 14 is represented schematically in FIG. 4.

Allyl 6-O-(2,3,4,6-tetra-O-benzyl-α-D-mannopyranosyl)-2,3,4-tri-O-benzyl-α-D-mannopyranoside 20

18

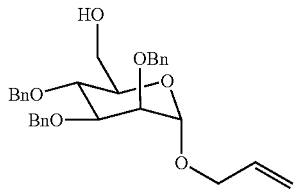

20

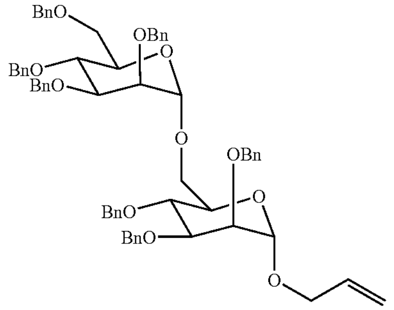

21

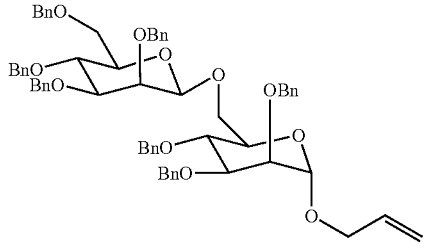

DBU (54 μL, 0.36 mmol) was added to a solution of tetra-O-benzyl-D-mannopyranose (Koto et al., 1976) (1.92 g, 3.6 mmol) and trichloroacetonitrile (722 μL, 7.2 mmol) in dry $CH_2Cl_2$ (30 mL) under a $N_2$ atmosphere. The reaction mixture was stirred for 1 hr at room temperature, the solvent removed in vacuo and the residue purified by silica-gel column chromatography [hexanes/diethyl ether/$NEt_3$ 30:10:0.04 as the eluent] to give trichloroimidate 19 (1.70 g, 70%) which was used immediately. TMSOTf (78 μL, 0.36 mmol) was added to a solution of mannoside 18 (1.09 g, 2.38 mmol) (Ogawa et al., 1985), 19 (1.70 g) and 4 Å molecular sieves (0.5 g) in dry ether (20 mL) at 0° C. under an $N_2$ atmosphere. The reaction mixture was warmed to room temperature and stirred for 3 hrs. After this time the mixture was filtered, diluted with $CH_2Cl_2$, washed with saturated $NaHCO_3$ and brine. The organic layer was dried over $MgSO_4$, the solvent removed in vacuo and purification of the residue by silica-gel column chromatography [hexanes/ether 1:1 as the eluant] gave the title compound 20 (0.74 g, 31%) as a colourless syrup. $R_f$ 0.7 (hexanes/ether 1:1); $[\alpha]_D^{28}$ +28 (c 1, $CH_2Cl_2$); $^1H$ NMR (500 MHz, $CDCl_3$) δ 7.39-7.14 (m, 355H), 5.84 (dddd, H, J 17, 11, 6 and 5 Hz), 5.23 (dq, 1H, J 17 and 2 Hz), 5.18-5.14 (m, 2H), 4.92 (2 overlapping d, 2H, J 11 Hz), 4.87 (d, 1H, J 2 Hz, H-1'), 4.77-4.49 (m, 11H), 4.11 (ddt, 1H, J 11, 5 and 2 Hz), 4.04 (t, 1H, J 9 Hz), 3.97-3.86 (m, 5H), 3.84-3.77 (m, 2H), 3.75-3.68 (m, 3H), 3.65 (dd, 1H, J 11 and 2 Hz); $^{13}C$ NMR (125 MHz, $CDCl_3$) δ 139.0, 139.0, 138.8, 138.7, 138.7, 138.7, 138.5 (7× ipso-C), 133.9 (C-2), 128.6-127.6 (Ph) 117.7 (C-3), 98.3 (C-1", $^1J_{C-H}$ 170 Hz), 97.2 (C-1', $^1J_{C-H}$ 170 Hz), 80.6, 79.7, 75.3, 75.3, 75.2, 75.1, 75.1, 74.9, 73.5, 73.1, 72.6, 72.4, 72.1, 72.0, 7.8, 68.0, 66.3, 65.5; HRMS-ESI (+ve) (Found: m/z 1013.4848 ($MH^+$). $C_{64}H_{69}O_{11}$ requires m/z 1013.4840)

A further fraction gave allyl 6-O-(2,3,4,6-tetra-O-benzyl-β-D-mannopyranosyl)-2,3,4-tri-O-benzyl-α-D-mannopyranoside 21 (0.23 g, 10%) as colourless syrups. $R_f$ 0.6 (hexanes/ether 1:1); $[\alpha]_D^{27}$ −4 (c 0.9, $CH_2Cl_2$) $^1H$ NMR (500 MHz, $CDCl_3$) δ 7.47-7.16 (m, 35H), 5.82 (dddd, 1H, J 17, 11, 6.5 and 5 Hz, H-2), 5.19 (dq, 1H, J 17 and 2 Hz, H-3), 5.14 (dq, 1H, J 11 and 2 Hz, H-3), 5.01 (d, 1H, J=12 Hz), 4.93-4.89 (m, 3H), 4.85 (d, 1H, J=12 Hz), 4.71 (d, 1H, J=2 Hz, H-1'), 4.68-4.53 (m, 6H), 4.49 (d, 1H, J 12 Hz), 4.43 (d, 1H, J 12 Hz), 4.28 (dd, 1H, J 10 and 2 Hz), 4.25 (s, 1H, H-1"), 4.15 (ddt, 1H, J 13, 5 and 2 Hz, H-1), 3.98 (dd, 1H, J 9 and 3 Hz), 3.95-3.75 (m, 8H), 3.60 (dd, 1H, J 10 and 6 Hz), 3.46-3.3.40 (m, 2H); $^{13}C$ NMR (125 MHz, $CDCl_3$) δ138.9, 138.6, 138.6, 138.5, 138.5, 138.3, 138.3 (7× ipso-C), 133.7 (C-2), 128.6-127.3 (Ph), 117.3 (C-3), 102.2 (C-1", $^1J_{C-H}$ 155 Hz), 96.9 (C-1', $^1J_{C-H}$ 169 Hz), 82.1, 80.4, 76.0, 75.2, 75.0, 75.0, 74.8, 74.6, 73.7, 73.6, 73.3, 72.1, 71.5, 71.4, 69.8, 69.0, 67.6 (C-1); HRMS-ESI (+ve) (Found: m/z 1035.4665 (a). $C_{64}H_{68}O_{11}Na$ requires m/z 1035.4659)

1-O-[6-O-(2,3,4,6-tetra-O-benzyl-α-D-mannopyranosyl)-2,3,4-tri-O-benzyl-α-D-mannopyranosyl]glycerol 22

22

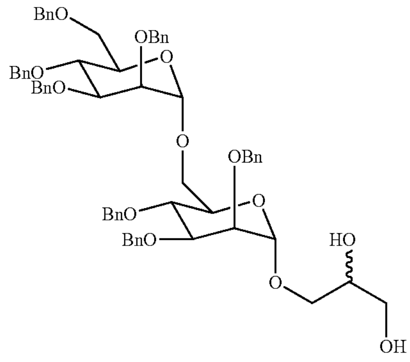

A solution of $OsO_4$ (1% in $H_2O$, 1 mL) was added to a mixture of dimannoside 20 (0.50 g, 0.49 mmol) and N-methylmorpholine-1-oxide (100 mg, 0.85 mmol) in acetone/water (9:1, 20 mL). The reaction mixture was stirred overnight at room temperature, poured into 10% sodium thiosulfate solution (100 mL) and extracted into ethyl acetate. The organic layer was washed with water, dried over $MgSO_4$ and the solvent removed in vacuo. Purification of the residue by silica-gel column chromatography [hexanes/ether 1:1→diethyl ether gradient elution] gave the title compound 22 (0.35 g, 67%, 1:1 mixture of C-2 epimers) as a colourless syrup. $v_{max}/cm^{-1}$ 3436 (OH); $^1H$ NMR (500 MHz, $CDCl_3$) 8 inter alia 7.40-7.15 (m, 35H), 5.04 (d, 0.5H, J 2 Hz H-1'), 5.03 (d, 0.5H, J 2 Hz H-1"), 4.88-4.83 (m, 2H), 4.80 (d, 0.5H, J 2 Hz, H-1'), 4.79 (d, 0.5H, J 2 Hz, H-1'), 4.74-4.44 (m, 10H), 4.07 (t, 1H, J 10 Hz), 4.00-3.44 (m, 18H); $^{13}C$ NMR ($CDCl_3$, 125 MHz) δ inter alia 138.6-138.1 (ipso-C), 128.4-127.5 (Ph), 98.8 and 98.5 (C-1"), 98.1 and 98.0 (C-1'), 80.0, 79.9, 79.6, 75.2, 75.2, 75.1, 75.0, 75.0, 74.9, 74.9, 74.8, 74.8, 74.7, 74.7, 73.3, 73.0, 72.5, 72.3, 72.2, 72.1, 71.8, 71.6, 70.7, 70.4, 70.3, 69.4, 69.2, 66.5, 66.4, 63.6, 63.5; HRMS-ESI (+ve) (Found: m/z 1069.4716 ($MNa^+$). $C_{64}H_{70}O_{13}Na$ requires m/z 1069.4714)

2,3-Di-O-stearoyl-1-O-[6-O-(2,3,4,6-tetra-O-benzyl-α-D-mannopyranosyl)-2,3,4-tri-O-benzol-α-D-mannopyranosyl]glycerol 23

23

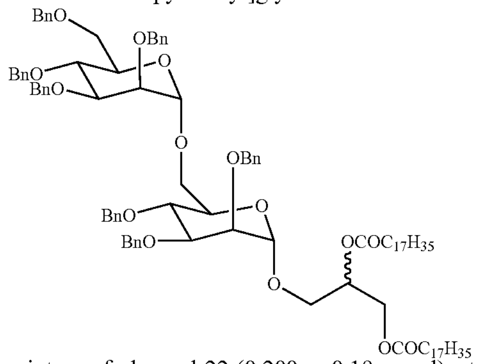

A mixture of glycerol 22 (0.200 g, 0.19 mmol), stearoyl chloride (0.14 g, 0.48 mmol) and pyridine (1 mL) in dry dichloromethane (20 mL) was stirred overnight at room temperature. The mixture was diluted with dichloromethane, washed with 1 M HCl solution, saturated sodium bicarbonate solution, brine then dried over $MgSO_4$. The solvent was removed in vacuo and the residue was purified by silica-gel column chromatography [hexanes/diethyl ether 4:1 as eluent] to provide 23 (0.260 g, 84%) as a 1:1 mixture of stereoisomeric diglycerides. $v_{max}/cm^{-1}$ 1739 (C═O); $^1H$ NMR (500 MHz, $CDCl_3$) δ inter alia 7.36-7.14 (m, 35H), 5.25-5.14 (m, 2H, H-1" and H-2), 4.92-4.88 (m, 2H), 4.84 and 4.79 (2×d, each 0.5H, H-1'), 4.76-4.46 (m, 12H), 4.31 and 4.23 (2×dd, each 0.5H), 4.14-3.62 (m, 12H), 3.51 (ddd, 1H, J 12, 7 and 5 Hz), 2.32-2.20 (m, 4H), 1.66-1.50 (m, 4H), 1.34-1.20 (m, 56H), 0.90-0.84 (m, 6H); $^{13}C$ NMR (125 MHz, $CDCl_3$) δ inter alia 173.4 (C═O), 173.0 and 172.9 (C═O), 138.8-138.2 (ispso-C), 128.4-127.4, 98.4 and 98.3 (C-1"), 98.2 and 97.8 (C-1'), 80.1, 79.5, 79.4, 75.1, 75.0, 74.8, 74.4, 74.3, 73.3, 73.0, 72.9, 72.4, 72.4, 72.3, 72.2, 72.1, 72.1, 71.9, 71.5, 69.7, 69.4, 69.2, 65.8, 65.6, 65.3, 62.5, 62.4, 34.3, 34.1, 32.0, 29.8-22.7, 14.2.

2,3-Di-O-stearoyl-1-O-[(6-O-α-D-mannopyranosyl)-α-D-mannopyranosyl]glycerol 24

24

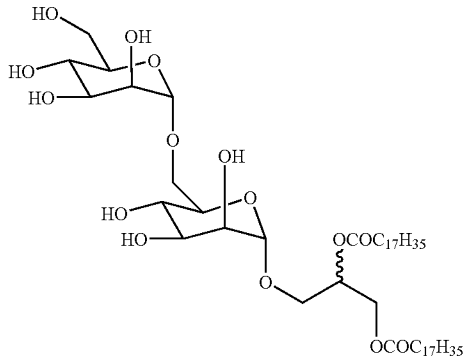

A mixture of 23 (0.200 g, 0.13 mmol) and 10% palladium on carbon catalyst (0.1 g) in ethanol (20 mL) was stirred under an atmosphere of $H_2$ for 4 days. The mixture was filtered through a pad of Celite and the filter cake was washed with methanol and dichloromethane. The solvents were removed in vacuo and the residue purified by silica-gel column chromatography [$CH_2Cl_2$/MeOH 10:0.1 as the eluent] to gave the title compound 24 (0.118 g, 92%, 1:1 mixture of C-2 epimers) as a white solid. $^1H$ NMR (500 MHz, $CDCl_3/CD_3OD/D_2O$ 70:40:6) δ inter alia 4.98-4.92 (m, 1H, H-2), 4.57-4.54 (m, 1H, H-1"), 4.49 (d, 0.5H, J 1.5 Hz, H-1'), 4.81 (d, 0.5H, J 1 Hz, H-1'), 4.09 (ddd, 0.5H, J 12.5, 6.5 and 3 Hz), 3.91-3.84 (m, 0.5H), 3.75-3.68 (m, 0.5H), 3.64-3.28 (m, 10H), 2.09-2.01 (m, 4H), 1.38-1.28 (m, 4H), 1.08-0.92 (m, 56H), 0.59 (t, 6H, J 7 Hz); $^{13}C$ NMR (125 MHz, $CDCl_3/CD_3OD/D_2O$ 70:40:6) 8 inter alia 173.6, 173.6, 173.3, 173.3 (each 0.5C, 4×C═O), 100.2 (0.5C, C-1"), 99.9 (0.5C, C-1"), 99.4 (C-1'), 72.2, 71.2, 71.2, 70.9, 70.7, 70.0, 69.9, 69.9, 69.6, 69.3, 66.5, 65.9, 65.2, 64.9, 64.9, 62.2, 60.8, 33.7, 33.6, 31.4, 29.1-28.5, 14.4, 24.4, 24.3, 22.1, 13.3: HRMS-ESI (+ve) (Found: m/z 971.6628 ($MNa^+$). $C_{51}H_{96}O_{15}Na$ requires m/z 971.6647).

Example 1(e)

Synthesis of Compound 28

The total synthesis of compound 28 is represented schematically in FIG. 5.

Technical Grade Sodium Stearate

The syntheses of target compounds 28, 31, 35 and 43 utilised intermediates derived from technical grade sodium stearate. The sodium stearate was analysed as its methyl esters; methyl octadecanoate, methyl hexadecanoate, methyl tetradecanoate, methyl dodecanoate and methyl decadecanoate; and found to be a mixture of stearic acid (55%), palmitic acid (36%), myristic acid (2%), lauric acid (2%) and decadecanoic acid (1%).

Analytical Procedure

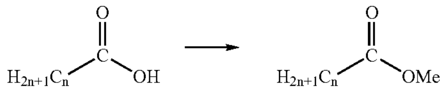

n = 11, 13, 15, 17, 19

Acetyl chloride (3.00 mL, 42.1 mmol) was added drop wise to a stirred solution of technical grade sodium stearate (227 mg, 0.741 mmol) in methanol (30 mL). The mixture was heated to 80° C. for 1 hr. After cooling the mixture was concentrated to ca half volume and toluene (30 mL) was added and the solvents concentrated at reduced pressure. The crude residue was partitioned between ether (50 mL) and sat. $NaHCO_3$ (40 mL). The aqueous phase was re-extracted with ether (50 mL) and the combined ethereal extract washed with brine (50 mL) after drying ($MgSO_4$) and filtration the solvent was removed at reduced pressure to give the methyl ester (200 mg, 0.670 mmol, 90%) as an oil; $^{1}H$ NMR (300 MHz, $CDCl_3$) δ 3.66 (s, 3H), 2.32 (t, 2H, J 7.4 Hz), 1.65-1.58 (m, 2H), 1.32-1.21 (m, 26H), 0.89-0.80 (m, 3H); $^{13}C$ NMR (75 MHz, $CDCl_3$) δ 174.6, 51.7, 34.5, 32.3, 30.1, 30.0, 29.8, 29.7, 29.6, 29.5, 25.3, 23.0, 14.4; GC analysis of this material and comparison with standards confirmed a composition of methyl octadecanoate (55%), methyl hexadecanoate (36%), methyl tetradecanoate (2%), methyl dodecanoate (2%) and methyl decadecanoate (1%).

Phosphoramidites 25

25

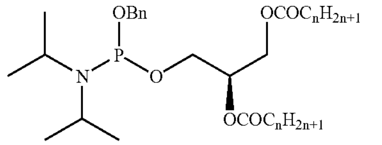

n = 11(1%), 13(2%), 15(36%), 17(55%), 19(2%)

The above mixture of fatty acids was converted to the acid chloride and by known methods (Dreef et al., 1991) was used to prepare the mixture of phosphoramidites 25 utilizing (S)-(+)-2,2-dimethyl-1,3-dioxolane-methanol as a starting material. The phosphoramidite mixture 25 was used for the preparation of target compounds 28, 31, 35 and 43.

2-O-[6-O-(2,3,4,6-tetra-O-benzyl-α-D-mannopyranosyl)-2,3,4-tri-O-benzyl-α-D-mannopyranosyl]-1,2-ethanediol 26

26

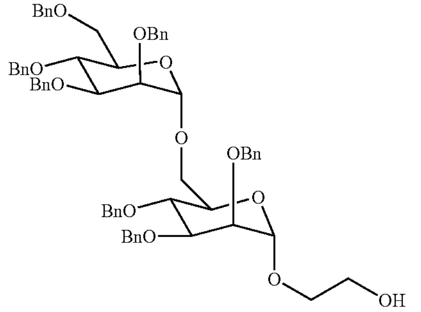

A solution of $OsO_4$ (1% in $H_2O$, 180 μL) was added to a mixture of dimannoside 20 (740 mg, 0.73 mmol) and $NaIO_4$ (940 mg, 0.94 mmol) in THF/$H_2O$ (7:3, 10 mL). The reaction mixture was stirred overnight at room temperature, quenched by the addition of 10% sodium sulfite and extracted with dichloromethane. The organic layer was washed with water, dried over $MgSO_4$ and the solvent removed in vacuo. The residue was purified by silica-gel column chromatography [hexanes/ether 1:1→ether, gradient elution] to give the title compound 26 (0.43 g, 58%) as a colourless syrup. $[\alpha]_D^{22}$ +25 (c 0.95, $CH_2Cl_2$); $\nu_{max}/cm^{-1}$ 3480 br (O—H); $^{1}H$ NMR (300 MHz, $CDCl_3$) 7.40-7.15 (m, 35H), 5.06 (d, 1H, J 2 Hz, H-1"), 4.91-4.84 (m, 2H), 4.82 (d, 1H, J 2 Hz, H-1'), 4.76-4.44 (m, 13H), 4.01 (t, 1H, J 9 Hz), 3.96-3.56 (m, 14H); $^{13}C$ NMR: (125 MHz, $CDCl_3$) δ inter alia 138.9, 138.9, 138.8, 138.7, 138.6, 138.5, 138.4 (7×ipso-C), 128.6-127.6 (Ph), 98.9 (C-1"), 98.4 (C-1'), 80.3, 79.9, 75.3, 75.3, 75.2, 75.1, 75.1, 75.0, 73.5, 73.2, 72.7, 72.5, 72.1, 71.9, 70.8, 69.4, 66.6, 62.2; HRMS-ESI (+ve) (Found: m/z 1017.4789 ($MH^+$). $C_{63}H_{69}O_{12}$ requires m/z 1017.4789).

1-O-(Benzyl-1,2-di-O-stearoyl-sn-glycero-3-phosphoryl)-2-O-[6-O-(2,3,4,6-tetra-O-benzyl-α-D-mannopyranosyl)-2,3,4-tri-O-benzyl-α-D-mannopyranosyl]-1,2-ethanediol 27

27

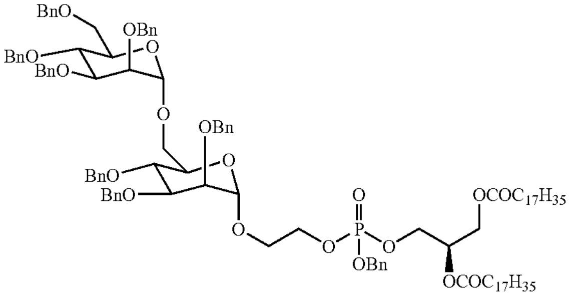

(structure of the bis-stearate, n = 17, depicted)

A solution of the phosphoramidite 25 (258 mg, 0.299 mmol) in dichloromethane (15 mL) was cannulated onto a mixture of the alcohol (199 mg, 0.196 mmol) and 1H-tetrazole (35.0 mg, 0.500 mmol) under argon. The reaction mixture was stirred at RT for 2 hrs then cooled in ice when a solution of MCPBA (75%, 137 mg, 0.556 mmol), pre-dried for 20 min over $MgSO_4$, was added to the reaction mixture. After a further 30 min. the reaction mixture was diluted with dichloromethane (30 mL) and quenched with the addition of 10% aqueous sodium thiosulfate (30 mL). The aqueous phase was further extracted with dichloromethane (30 mL) and the combined organic extract washed with sat. $NaHCO_3$ (2×40 mL) and dried ($MgSO_4$). After filtration the solvent was removed at reduced pressure to give the crude product that was purified by column chromatography on silica gel. Gradient elution with ethyl acetate/petroleum ether (30:70→45:55) afforded the title compound 27 (215 mg, 0.120 mmol, 61%) as a thin film, $[\alpha]_D^{22}$ +19 (c 2.2, EtOAc); $^{1}H$ NMR (300 Mz, $CDCl_3$) δ 7.40-7.05 (m, 40H), 5.20-3.50 (m, 39H), 2.28-2.19 (m, 4H), 1.60-1.45 (4H, m), 1.28-1.19 (m, 56H), 0.90-0.80 (m, 6H); $^{13}C$ NMR (75 MHz, $CDCl_3$) δ 173.5, 173.1, 139.1, 138.9, 138.7, 129.1, 128.7, 128.6, 128.3, 128.3, 128.1, 127.9, 127.7, 98.6, 80.6, 79.7, 75.4, 74.8, 73.7, 73.4, 72.8, 72.4, 71.8, 69.6, 66.8, 66.2, 65.8, 62.0, 34.5, 34.4, 32.3, 30.1, 29.9, 29.7, 29.5, 25.2, 23.1, 14.5; LRMS-ESI (+ve) m/z 1812 (10%), 1784 (100), 1756 (75) 1728 (30), 1700 (10). HRMS-ESI (+ve) (Found: m/z 1811.0485 (MNH4+). $C_{109}H_{153}NO_{19}P$ requires m/z 1811.0774)

Sodium 1-O-(1,2-di-O-stearoyl-sn-glycero-3-phosphoryl)-2-O-[6-O-(α-D-mannopyranosyl)-α-D-mannopyranosyl]-1,2-ethanediol 28

28

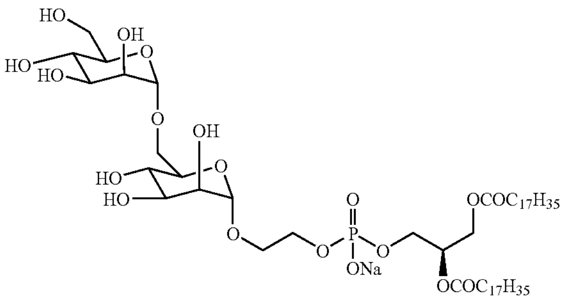

(structure of the bis-stearate, n = 17, depicted)

A mixture of the lipid 27 (98 mg, 0.055 mmol), $NaHCO_3$ (6.5 mg, 0.077 mmol) and Pd-black in $^{t}$BuOH (5 mL) and $H_2O$ (0.8 mL) was hydrogenated at 300 psi/50° C. for 15 hrs. After removal of the hydrogen the reaction mixture was filtered through Celite and the pad washed with $CHCl_3$/MeOH/$H_2O$ (70:40:08) (2×15 mL). Silica was added to the filtrate and the solvent was removed at reduced pressure to give a free flowing solid. Gradient elution with $CHCl_3$→$CHCl_3$/MeOH (80:20)→$CHCl_3$/MeOH (70:40)→$CHCl_3$/MeOH/$H_2O$ (70:40:05) afforded the title compound 28 (42 mg, 0.038 mmol, 69%) that was lyophilized to give a white solid $[\alpha]_D^{22}$ +38 (c 0.10, $CHCl_3$/MeOH/$H_2O$, 70:40:6); $^1$H NMR (300 MHz, $CDCl_3$/$CD_3OD$/$D_2O$, 70:40:6) δ 5.07-4.98 (m, 1H), 4.67 (bs, 1H), 4.60 (bs, 1H), 4.20-3.40 (m, 20H), 2.16-2.02 (m, 4H), 1.40-1.32 (m, 4H), 1.15-1.00 (m, 56H), 0.85-0.80 (m, 6H); $^{13}$C NMR (75 MHz, $CDCl_3$/$CD_3OD$/$D_2O$, 70:40:6) δ 176.0, 175.6, 101.7, 100.8, 74.4, 73.0, 72.7, 72.4, 72.2, 68.9, 68.6, 67.5, 66.5, 65.3, 64.6, 62.8, 36.0, 35.8, 33.6, 31.4, 31.0, 30.9, 26.7, 26.6, 24.4, 15.6; $^{31}$P NMR (121.5 MHz, $CDCl_3$/$CD_3OD$/$D_2O$, 70:40:6) δ 0.62; LRMS-ESI (−ve) m/z 1072 (15%), 1044 (100), 1016 (75), 988 (30), 960 (10). HRMS-ESI (−ve) (Found: m/z 1071.6521 $(M-Na)^-$. $C_{109}H_{153}NO_{19}P$ requires m/z 1071.6602).

Example 1(f)

Synthesis of Compound 31

The total synthesis of compound 31 is represented schematically in FIG. 6.

3-Hydroxypropyl 2,3,4,6-tetra-O-benzyl-α-D-mannopyranoside 29 (Lindhorst et al.; 2000)

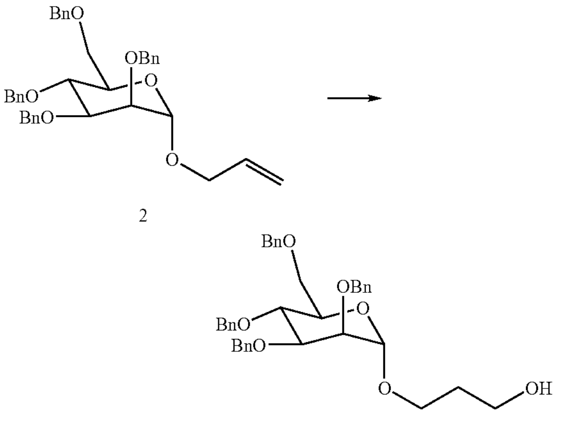

2

29

9-BBN (3.75 ml, 1.88 mmol) was added drop-wise to a solution of 2 (0.500 g, 0.86 mmol) in dry THF (10 ml) under an $N_2$ atmosphere at 0° C. The reaction mixture was stirred at room temperature for 24 hrs, cooled to 0° C. and a mixture of 3M NaOH (10 mL) and 30% aqueous $H_2O_2$ (1 mL) was added. The mixture was stirred at room temperature for 48 hours, the phases separated and the aqueous phase extracted 3 times with EtOAc. The organic layers were combined and washed with brine, dried over $MgSO_4$ and the solvent removed in vacuo. The residue was purified by silica-gel column chromatography [hexanes/ether 1:1 as the eluant ($R_f$=0.14)] to provide the title compound 29 (0.270 g, 55%) as a colourless syrup. $[\alpha]_D^{23}$ +20 (c 1.1, $CH_2Cl_2$); $\nu_{max}$ cm$^{-1}$ 3437 br (O—H); $^1$H NMR: (500 MHz, $CDCl_3$) δ 7.40-7.10 (m, 20H, Ph-H), 4.86 (d, 1H), 4.85 (d, 1H, J 2.0 Hz, H-1), 4.77-4.47 (m, 7H), 3.93 (t, 1H, J 9.4 Hz, H-4), 3.85 (m, 2H), 3.79-3.63 (m, 6H), 3.50 (dt, 1H, J=9.8 and 5.6 Hz), 1.79 (quin, 2H, J=6 Hz) ppm.

1-O-(Benzyl-1,2-di-O-stearoyl-sn-glycero-3-phosphoryl)-3-O-(2,3,4,6-tetra-O-benzyl-α-D-mannopyranosyl)-1,3-propanediol 30

30

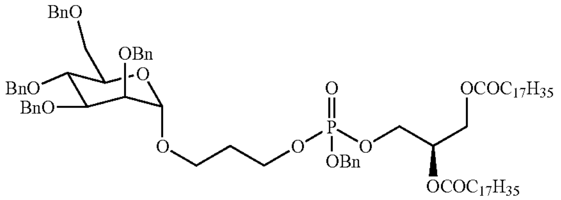

(structure of the bis-stearate, n = 17, depicted)

A solution of the phosphoramidites 25 (330 mg, 0.383 mmol) in dichloromethane (15 mL) was cannulated onto a mixture of the alcohol 29 (185 mg, 0.309 mmol) and 1H-tetrazole (50.0 mg, 0.714 mmol) under argon. The reaction mixture was stirred at RT for 2 hrs then cooled in ice when a solution of MCPBA (75%, 164 mg, 0.665 mmol), pre-dried for 20 min over $MgSO_4$, was added to the reaction mixture. After a further 1 hr the reaction mixture was diluted with dichloromethane (30 mL) and quenched with the addition of 10% aqueous sodium thiosulfate (45 mL). The aqueous phase was further extracted with dichloromethane (35 mL) and the combined organic extract washed with sat. $NaHCO_3$ (2×40 mL) and dried ($MgSO_4$). After filtration the solvent was removed at reduced pressure to give the crude product that was purified by column chromatography on silica gel. Gradient elution with ethyl acetate/petroleum ether (20:80→40:60) afforded the title compound 30 (301 mg, 0.219 mmol, 71%) as a thin film; $[\alpha]_D^{20}$ +11 (c 0.54, EtOAc); $^1$H NMR (300 MHz, $CDCl_3$) δ 7.40-7.10 (m, 25H), 5.20-5.12 (m, 1H), 5.07-5.00 (m, 2H), 4.85-4.62 (m, 9H), 4.30-4.20 (m, 1H), 4.10-3.62 (m, 12H), 3.45-3.37 (m, 1H), 2.30-2.20 (m, 4H), 1.90-1.80 (m, 2H), 1.60-1.48 (m, 4H), 1.30-1.18 (m, 56H), 0.88-0.80 (m, 6H); $^{13}$C NMR (75 MHz, $CDCl_3$); δ 173.5, 173.1, 138.8, 129.0, 128.7, 128.4, 128.3, 128.1, 128.0, 127.9, 127.8, 98.5, 80.6, 75.5, 75.3, 73.8, 73.1, 72.6, 72.5, 69.8, 69.7, 65.7, 65.5, 63.7, 62.1, 34.5, 34.4, 32.3, 30.7, 30.1, 29.9, 29.7, 29.5, 25.2, 23.1, 14.5; $^{31}$P NMR (121.2 MHz, $CDCl_3$) δ 0.36; LRMS-ESI (+ve) m/z 1394 (20%), 1366 (100), 1338 (40) 1310 (10). HRMS-ESI (+ve) (Found: m/z 1392.9149 M $C_{83}H_{127}NO_{14}P$ requires m/z 1392.8994).

Sodium 1-O-(1,2-di-O-stearoyl-sn-glycero-3-phosphoryl-3-O-(α-D-mannopyranosyl)-1,3-propanediol 31

31

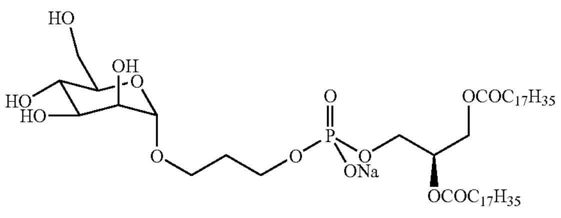

(structure of the bis-stearate, n = 17, depicted)

A mixture of lipid 30 (110 mg, 0.0800 mmol), $NaHCO_3$ (8.8 mg, 0.105 mmol) and Pd-black in ${}^tBuOH$ (6 mL) and $H_2O$ (0.8 mL) was hydrogenated at 300 psi/50° C. for 16 hrs. After removal of the hydrogen the reaction mixture was filtered through celite and the pad washed with $CHCl_3/MeOH/H_2O$ (70:40:08) (2×20 mL). Silica-gel was added to the filtrate and the solvent removed at reduced pressure to give a free flowing solid. Gradient elution with $CHCl_3$→$CHCl_3$/MeOH (80:20)→$CHCl_3$/MeOH (70:40)→$CHCl_3/MeOH/H_2O$ (70:40:05) afforded the title compound 31 (54 mg, 0.057 mmol, 71%) that was lyophilized to give a white solid $[\alpha]_D^{20}$ +31 (c 0.15, $CHCl_3/MeOH/H_2O$, 70:40:6); $^1H$ NMNR (300 Mlz, $CDCl_3CD_3OD/D_2O$, 70:40:6) δ 5.01-4.96 (m, 1H), 4.59-4.57 (bs, 1H), 4.20-4.17 (m, 1H), 4.00-3.95 (m, 1H), 3.78-3.20 (m, 12H), 2.15-2.05 (m, 4H), 1.70-1.60 (m, 2H), 1.42-1.30 (m, 4H), 1.15-0.98 (m, 56H), 0.85-0.79 (m, 6H); $^{31}P$ NMR (121.5 MHz, $CDCl_3/CD_3OD/D_2O$, 70:40:6) δ 0.36; LRMS-ESI (−ve) m/z 924 (20%), 896 (100), 868 (75) 840 (20); HRMS-ESI (−ve) (Found: m/z 923.6283 $(M\text{-}Na)^-$. $C_{48}H_{92}O_{14}P$ requires m/z 923.6230).

Example 1(g)

Synthesis of Compound 36

The total synthesis of compound 36 is represented schematically in FIG. 7.

(1R*,2R*)-1-O-Acetoxy-2-[2,3,4,6-tetra-O-benzyl-α-D-mannopyranosyloxy]cyclohexane 32

32

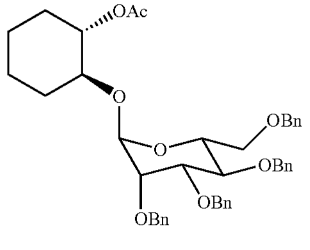

-continued

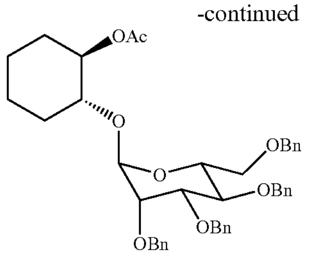

DBU (60 μL, 0.4 mmol) was added to a solution of 2,3,4,6-tetra-O-benzyl-D-mannopyranose (1.90 g, 3.5 mmol) and trichloroacetonitrile (700 μL, 7.0 mmol) in dry $CH_2Cl_2$ (20 ml) under an $N_2$ atmosphere. The reaction mixture was stirred for 1 hr at room temperature, the solvent removed in vacuo and the residue purified by silica-gel column chromatography [hexanes/diethyl ether/$NEt_3$ 30:10:0.04 as the eluant] to give trichloroimidate 19 (1.80 g, 75%) which was used immediately. TMSOTf (115 μL, 0.59 mmol) was added to a solution of 2-acetoxycyclohexan-1-ol (2.00 g, 2.94 mmol) (Iranpoor et al., 1996), 19 (1.80 g, 2.63 mmol) and 4 Å molecular sieves (0.5 g) in dry $CH_2Cl_2$ (20 ml) at 0° C. under an $N_2$ atmosphere. The reaction mixture was warmed to room temperature and stirred for 3 hrs, filtered, diluted with $CH_2Cl_2$, washed with saturated $NaHCO_3$ and brine. The organic layer was dried over $MgSO_4$ and the solvent removed in vacuo. Purification of the residue by silica-gel column chromatography [hexanes/ether 1:1 as the eluant] provided the title compound 32 (1.11 g, 61%, 1:1 mixture of (1R,2R) and (1S,2S)-diastereoisomers) as a colourless syrup. $\nu_{max}/cm^{-1}$ 1737 (C═O); $^1H$ NMR: (500 MHz, $CDCl_3$) 8 inter alia 7.38-7.12 (m, 20H), 5.05 (d, 0.5H, J=2 Hz, H-1'), 5.00 (d, 0.5H, J 2 Hz, H-1'), 4.88 (t, 1H, J 11 Hz), 4.89-4.48 (m, 8H), 3.98-3.86 (m, 5H), 3.82-3.67 (m, 6H), 3.64 (dt, 0.5H, J 4.5 and 10 Hz), 3.56 (ddd, 0.5H, J 10.5, 9 and 4.5 Hz), 2.10-1.92 (m, 2H), 1.97 and 1.87 (2×s, each 1.5H, OAc), 1.72-1.58 (m, 2H), 1.42-1.11 (m, 4H); $^{13}C$ NMR: (125 MHz, $CDCl_3$) 8 inter alia 170.6 and 170.3 (C═O), 139.0, 138.6, 138.5, 138.5 (ipso-C), 128.4127.3, 99.7 and 93.6 (C-1'), 80.3, 80.3, 79.1, 75.9, 75.2, 75.2, 74.9, 74.8, 74.3, 73.9, 73.4, 73.2, 72.8, 72.5, 72.4, 72.2, 72.2, 71.7, 69.5, 69.5, 31.9, 30.3, 30.2, 28.5, 23.7, 23.6, 23.5, 23.2, 21.3, 21.2; HRMS-ESI (+ve) (Found: m/z 703.3251 $(MNa^+)$. $C_{42}H_{48}O_8Na$ requires m/z 703.3247).

(1S,2S)- and (1R,2R)-2-(2,3,4,6-tetra-O-benzyl-α-D-mannopyranosyloxy)cyclohexanol 33 and 34

33*

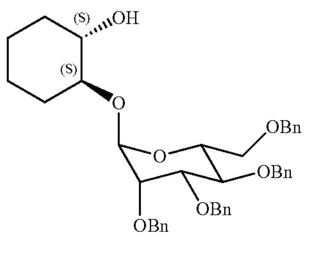

-continued

34*

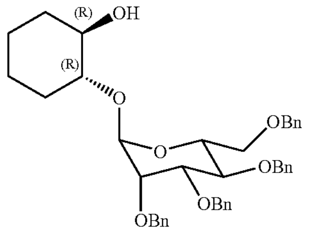

*structures may be interchanged

A mixture of 32 (1.11 g, 1.61 mmol) and IRA 401 (OH) (1 g) in methanol (50 ml) was stirred at room temperature overnight. The mixture was filtered and the solvent removed in vacuo. Purification of the residue by silica-gel column chromatography [hexanes→hexanes/ether 1:1 gradient elution] gave (1S,2S)-2-(2,3,4,6-tetra-O-benzyl-α-D-mannopyranosyloxy)cyclohexanol 33*(0.42 g, 41%), ($R_f$=0.51, hexane/ether 1:2) as a clear syrup; $[\alpha]_D^{28}$ +35 (c 0.8, $CH_2Cl_2$); $\nu_{max}$/$cm^{-1}$ 3469 br (O—H); $^1H$ NMR: (500 MHz, $CDCl_3$) δ 7.40-7.22 (m, 16H, Ph-H), 7.20-7.18 (m, 4H, Ph-H), 5.01 (d, 1H, J=2 Hz, H-1), 4.82-4.44 (m, 8H, 4×$PhCH_2$), 4.00-3.88 (m, 3H), 3.78-3.68 (m, 3H), 3.40-3.33 (m, 1H, H-1), 3.31-3.24 (m, 1H, H-2), 2.01-1.94 (m, 1H), 1.90-1.84 (m, 1H), 1.66-1.64 (m, 2H), 1.28-1.14 (m, 4H); $^{13}$CNMR: (125 MHz, $CDCl_3$) δ 138.5, 138.4, 138.4, 138.3, 128.4, 128.4, 128.4, 128.3, 128.0, 127.9, 127.8, 127.8, 127.7, 127.7, 127.5, 97.3 (C-1'), 84.1, 79.8, 75.8, 75.1, 75.0, 73.6, 73.4, 72.8, 72.4, 72.4, 69.2, 32.5, 30.4, 24.2, 24.0; HRMS-ESI (+ve) (Found: m/z 661.3143 ($MNa^+$). $C_{40}H_{46}O_7Na$ requires m/z 661.3141).

A second fraction gave (1R,2R)-2-(2,3,4,6-tetra-O-benzyl-α-D-mannopyranosyloxy)cyclohexanol 34*(0.36 g, 35%), ($R_f$=0.43, hexane/ether 1:2) as a white solid. $[\alpha]_D^{28}$ 18 (c 1.0, $CH_2Cl_2$); $\nu_{max}$/$cm^{-1}$ 3468 br (O—H); $^1H$ NMR: (500 MHz, $CDCl_3$) δ 7.40-7,21 (m, 16H), 7.21-7.19 (m, 4H), 5.15 (d, 1H, J=2 Hz, H-1'), 4.85-4.42 (m, 8H, 4×$PhCH_2$), 4.00-3.80 (m, 3H), 3.76 (dd, 1H, J11 and 5 Hz), 3.73 (dd, 1H, J11 and 2 Hz), 3.69 (t, 1H, J=2 Hz), 3.39-3.33 (m, 1H), 3.32-3.24 (m, 1H), 2.21 (brs, 1H, OH), 2.15-2.10 (m, 1H), 1.98-1,93 (m, 2H), 1.28-1.15 (m, 4H,); $^{13}$CNMR: (125 MHz, $CDCl_3$) δ 138.5, 138.5, 138.4, 138.3, 128.4, 128.4, 128.4, 128.3, 128.1, 128.0, 127.9, 127.7, 127.7, 127.7, 127.5, 99.3 (C-1'), 85.0, 79.8, 75.2, 75.2, 75.1, 73.8 73.4, 72.5, 72.4, 72.1, 69.5, 32.5, 31.4, 24.3, 24.0; HRMS-ESI(+ve) (Found: m/z 661.3123 ($MNa^+$). $C_{40}H_{46}O_7Na$ requires m/z 661.3141).

*-stereochemical assignment may be reversed. The C-1 and C-2 configurational assignments of 33 and 34 were made by comparison of the chemical shifts of H-1 and H-2 to those of the corresponding glucosides (Itano et al., 1980).

(1R,2R_-1-O-(Benzyl 1,2-di-O-stearoyl-sn-glycero-3-phosporyl)-2-O-(2,3,4,6-tetra-O-benzyl-α-D-mannopyranosyl)cylcohexane-1,2-diol 35

35

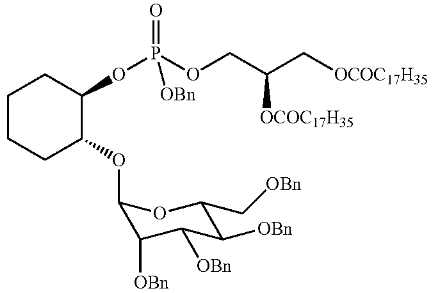

(structure of the bis-stearate, n = 17, depicted)

A solution of the phosphoramidites 25 (185 mg, 0.215 mmol) in dichloromethane (15 mL) was cumulated onto a mixture of the alcohol 34 (115 mg, 0.180 mmol) and 1H-tetrazole (36.0 mg, 0.514 mmol) under argon. The reaction mixture was stirred at RT for 90 min. then cooled in ice when a solution of MCPBA (75%, 125 mg, 0.507 mmol), pre-dried for 20 min over $MgSO_4$, was added to the reaction mixture. After a further 20 hrs the reaction mixture was diluted with dichloromethane (30 mL) and quenched with the addition of 10% aqueous sodium thiosulfate (45 mL). The aqueous phase was further extracted with dichloromethane (35 mL) and the combined organic extract washed with sat. $NaHCO_3$ (2×40 mL) and dried ($MgSO_4$). After filtration the solvent was removed at reduced pressure to give the crude product that was purified by column chromatography on silica gel. Gradient elution with ethyl acetate/petroleum ether (10:90→20:80) afforded the title compound 35 (90 mg, 0.064 mmol, 36%) as an inseparable mixture; $^{31}P$ NMR (121.2 MHz, $CDCl_3$) δ 9.2, 9.1, −0.05, −0.08; LRMS-ESI (+ve) 1434 (15%), 1406 (100), 1388 (40) 1350 (10); HRMS-ESI (+ve) (Found: m/z 1432.9521 ($MNH_4^+$). $C_{86}H_{131}NO_{14}P$ requires m/z 1432.9302).

1-O-(Sodium 1,2-di-O-stearoyl-sn-glycero-3-phosphoryl)-2-O-(-α-D-mannopyranosyl)-cyclohexane-1,2-diol 36

36

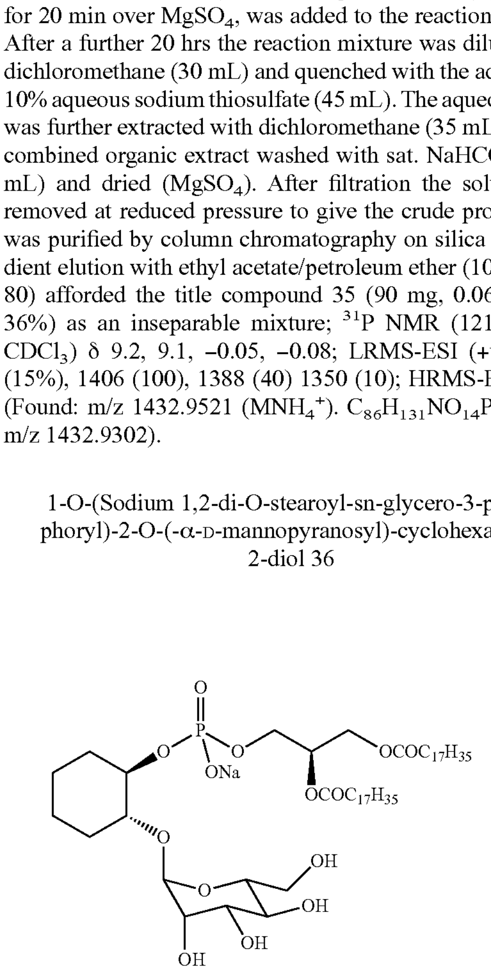

(structure of the bis-stearate, n = 17, depicted)

A mixture of the perbenzyl glycolipid 35 (45 mg, 0.032 mmol), $NaHCO_3$ (8.0 mg, 0.095 mmol) and Pd-black (77 mg) in $^t$BuOH (3 mL) and $H_2O$ (1.5 mL) was hydrogenated at 300 psi/50° C. for 15 hrs. After removal of the hydrogen the reaction mixture was filtered through celite and the pad washed with $CHCl_3$/MeOH/$H_2O$ (70:40:08) (2×20 mL). Silica was added to the filtrate and the solvent removed at reduced pressure to give a free flowing solid. Gradient elution with $CHCl_3$→$CHCl_3$/MeOH (80:20)→$CHCl_3$/MeOH (70:40)→$CHCl_3$/MeOH/$H_2O$ (70:40:02) afforded the title compound 36 (11 mg, 0.011 mmol, 34%) that was lyophilized to give a white solid $[\alpha]_D^{20}$ +32 (c 0.55, $CHCl_3$/MeOH/$H_2O$, 70:40:8); $^1H$ NMR (300 MHz, $CDCl_3$/$CD_3OD$/$D_2O$, 70:40:6) δ 5.27-5.19 (m, 1H), 5.12 (bs, 1H), 4.42-4.37 (m, 1H), 4.20-4.14 (m, 1H), 4.50-3.48 (m, 10H), 2.38-2.30 (m, 4H), 2.12-2.03 (m, 1H), 1.99-1.90 (m, 1H), 1.70-1.55 (m, 6H), 1.40-1.20 (m 60H), 0.96-0.90 (m, 3H); $^{31}P$ NMR (121.5

MHz, $CDCl_3/CD_3OD/D_2O$, 70:40:6) δ −0.32; HRMS-ESI(−ve) (Found: m/z 747.3939 $(M-Na)^-$. $C_{33}H_{64}O_{16}P$ requires m/z 747.3939).

Example 1(h)

Synthesis of Compound 44

The total synthesis of compound 44 is represented schematically in FIG. 8.

Allyl 2,3,4,6-tetra-O-benzyl-α-D-galactopyranoside 37 (Gigg et al.; 1985)

37

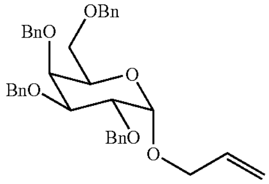

Sodium hydride (3.50 g, 60% dispersion in oil) was carefully added to a stirred suspension of allyl α-D-galactopyranoside (3.50 g, 15.9 mmol) in benzyl chloride (75 mL). The mixture was heated at 125-130° C. for 3 h, cooled to room temperature and filtered through Celite. Removal of the excess benzyl chloride on a high vacuum rotary evaporator and purification of the residue by silica-gel column chromatography (diethyl ether/hexanes 1:4 as eluent) gave the title compound 37 (4.97 g, 54%) as a pale syrup. $[\alpha]_D^{20}$ +60 (c 0.9, $CH_2Cl_2$) $^1H$ NMR (300 MHz, $CDCl_3$) δ 7.50-7.22 (m, 20H), 5.95 (dddd, 1H, J 17, 10, 7 and 5 Hz, H-2), 5.31 (dq, 1H, J 17 Hz, H-3), 5.20 (dq, 1H, J 10 Hz, H-3), 5.00-4.39 (m, 9H), 4.17 (ddt, 1H, J 13, 5 and 1.5 Hz), 4.10-3.94 (m, 2H), 3.59-3.49 9 m, 2H).

1-O-(2,3,4,6-Tetra-O-benzyl-α-D-galactopyranosyl) glycerol 38

38

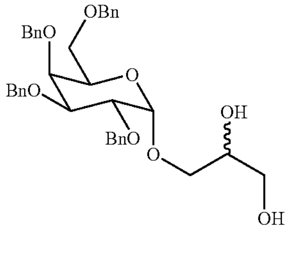

1% Osmium tetraoxide in water (2 mL) was added to a solution allyl galactoside 37 (1.55 g, 2.67 mmol) and 1-methylmorpholine-1-oxide (0.470 g, 4.00 mmol) in a 9:1 mixture of acetone and water (50 mL). The mixture was stirred for 23 h after which time it was poured into 5% sodium thiosulfate solution (100 mL). The mixture was extracted into dichloromethane and the organic extract washed with 10% hydrochloric acid, water and dried over magnesium sulfate. Removal of the solvent and purification of the residue by silica-gel column chromatography (dichloromethane/diethyl ether 4:1 as eluent) gave the title compound 38 (1.227 g, 75%) as a clear syrup. $^1H$ NMR (300 MHz, $CDCl_3$) δ 7.41-7.25 (m, 20H), 4.96-4.32 (m, 9H), 4.09-3.38 (m, 11H), 2.40-2.15 (m, 1H, OH), 1.63 (brs, 1H, OH); HRMS-ESI (+ve) (Found: m/z 637.2763 $(MNa^+)$. $C_{37}H_{42}O_{10}Na$ requires m/z 637.2777).

2-O-Benzoyl-1-O-(2,3,4,6-tetra-O-benzyl-α-D-galactopyranosyl)glycerol 39

39

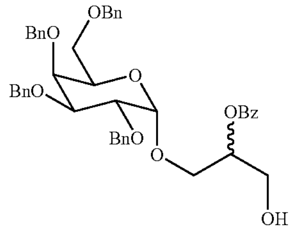

40

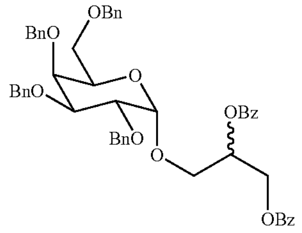

A stirred mixture of glycerol 38 (3.00 g, 4.88 mmol) and trityl chloride (1.63 g, 5.85 mmol) in pyridine (50 mL) was heated at 100° C. for 3 h. After cooling to 0° C. benzoyl chloride (1.70 g, 12.2 mmol) was added and the mixture warmed to room temperature and stirred for 17 h. Excess pyridine was removed on a high vacuum rotary evaporator and the residue was dissolved in dichloromethane. The mixture was washed with saturated sodium hydrogen carbonate solution, 10% hydrochloric acid, water and dried over magnesium sulfate. After removal of the solvent the residual syrup was dissolved in a 7:3 mixture of dichloromethane and methanol (100 mL). p-Toluenesulfonic acid (200 mg) was added and the mixture was stirred at room temperature for 20 h. The mixture was poured into water and extracted with dichloromethane. The organic layer was washed with saturated sodium hydrogen carbonate solution, water and dried over magnesium sulfate. Removal of the solvent and purification of the residue by silica-gel column chromatography (hexanes/diethyl ether 2:1→1:2 gradient elution) gave 2-di-O-benzoyl-1-O-(2,3,4,6-tetra-O-benzyl-α-D-galactopyranosyl)glycerol 40 (0.802 g, 20%, 1:1 mixture of diastereoisomers) as a pale syrup. $^1H$ NMR (300 MHz, $CDCl_3$) δ 8.09-8.01 (m, 4H), 7.62-7.50 (m, 2H), 7.48-7.20 (m, 24H), 5.72-5.64 (1H, m, H-2), 4.97-4.29 (m, 11H), 4.12-3.80 (m, 6H), 3.55-3.42 (m, 2H); HRMS-ESI (+ve) (Found: m/z 845.3292 $(MNa^+)$. $C_{51}H_{50}O_{10}Na$ requires m/z 845.3302)

A second fraction, the title compound 39 (1.69 g, 48%, 1:1 mixture of diastereoisomers) as a pale syrup. $^1H$ NMR (300 MHz, $CDCl_3$) δ 8.07-8.01 (m, 2H), 7.59-7.52 (m, 1H), 7.45-7.20 (m, 22H), 5.32-5.24 (m, 1H), 4.96-4.32 (m, 9H), 4.41-

3.74 (m, 8H), 3.54-3.42 (m, 2H); HRMS-ESI (+ve) (Found: m/z 736.3459 ($MNH_4^+$). $C_{44}H_{50}NO_9$ requires m/z 736.3480).

2-O-Benzoyl-1,3-bis-O-(2,3,4,6-tetra-O-benzyl-α-D-galactopyranosyl)glycerol 41

41

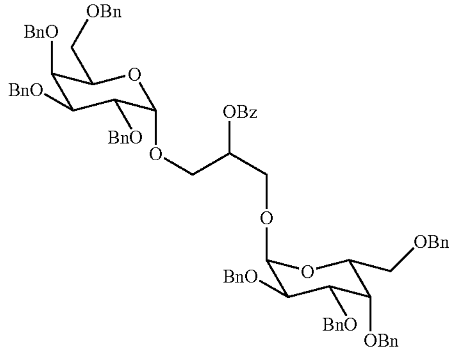

Trimethylsilyl trifluomethanesulfonate (35 μL, 0.19 mmol) was added dropwise to a stirred solution of the glycerol 39 (376 mg, 0.523 mmol) and O-(2,3,4,6-tetra-O-benzyl-α-D-galactopyranosyl)trichloroacetimidate (385 mg, 0.562 mmol) in dry ether (20 mL) under argon. After 90 min. solid $NaHCO_3$ (100 mg) was added and the mixture stirred for a further 10 min. The reaction mixture was partitioned between ether (50 mL) and sat. $NaHCO_3$ (40 mL). The aqueous phase was re-extracted with ether (50 mL) and the combined ethereal extract washed with 2M HCl (50 mL), sat. $NaHCO_3$ (40 mL) and $H_2O$ (60 mL). After drying ($MgSO_4$) and filtration the solvent was removed at reduced pressure to give the crude product that was purified by column chromatography on silica gel. Gradient elution with ethyl acetate/petroleum ether (10:90→20:80) afforded the title compound 41 (278 mg, 0.224 mmol, 61%) as a thin film; $[\alpha]_D^{20}$ +64.2 (c 1.30, ethyl acetate); $^1H$ NMR (300 MHz, $CDCl_3$) δ 8.05-7.99 (m, 2H), 7.50-7.42 (m, 1H), 7.35-7.10 (m, 42H), 5.57-5.45 (m, 1H), 4.95-4.82 (m, 4H), 4.79-4.30 (m, 15H), 4.00-3.72 (m, 11H), 3.55-3.38 (m, 4H); $^{13}C$ NMR (75 MHz, $CDCl_3$) δ 166.3, 139.2, 139.1, 139.0, 138.5, 133.4, 130.6, 130.2, 128.7, 128.65, 128.6, 128.1, 127.8, 98.7 ($^1J_{CH}$ 168 Hz), 98.3 ($^1J_{CH}$ 168 Hz), 79.3, 79.2, 76.9, 75.6, 75.2, 73.8, 73.8, 73.5, 73.4, 72.9, 70.0, 69.3, 69.2, 67.3, 66.7; HRMS-ESI (+ve) (Found: m/z 1258.5888 ($MNH_4^+$). $C_{70}H_{84}NO_{14}$ requires m/z 1258.886).

1,3-Bis-O-(2,3,4,6-tetra-O-benzyl-α-D-galactopyranosyl)glycerol 42

42

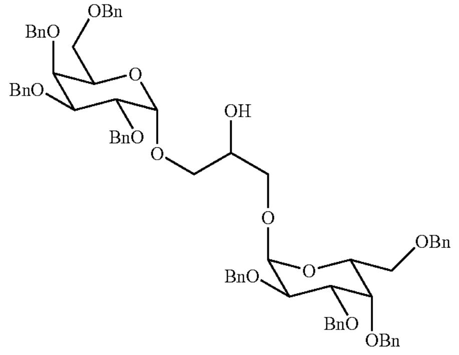

Sodium methoxide (30%, ca 0.1 mL) was added dropwise to a stirred solution of benzoate 41 (209 mg, 0.168 mmol) in dry methanol (6 mL) and dichloromethane (2 mL) under argon. After 12 hrs the reaction mixture was partitioned between ether (50 mL) and 2M HCl (50 mL). The aqueous phase was re-extracted with ether (50 mL) and the combined ethereal extract washed with $H_2O$ (60 mL). After drying ($MgSO_4$) and filtration the solvent was removed at reduced pressure to give the crude product that was purified by column chromatography on silica gel. Gradient elution with ethyl acetate/petroleum ether (30:70→50:50) afforded the title compound 42 (150 mg, 0.132 mmol, 79%) as a thin film; $[\alpha]_D^{22}$ +61.3 (c 3.00, $CH_2Cl_2$); $^1H$ NMR (300 MHz, $CDCl_3$) δ 7.35-7.15 (m, 40H), 4.90-4.35 (m, 18H), 4.10-3.82 (m, 9H), 3.70-3.42 (m, 9H); $^{13}C$ NMR (75 MHz, $CDCl_3$) δ 139.2, 139.1, 139.0, 138.9, 138.4, 128.8, 128.7, 128.6, 128.5, 128.4, 128.2, 128.1, 128.0, 127.9, 99.4, 99.2, 79.5, 77.1, 77.0, 75.5, 75.2, 73.9, 73.8, 73.6, 73.5, 71.1, 71.0, 70.2, 69.7, 69.6, 69.5; HRMS-ESI (+ve) (Found: m/z 1154.5579 ($MNH_4^+$). $C_{71}H_{80}NO_{14}$ requires m/z 1154.5624).

2-O-(Benzyloxy-1,2-di-O-stearoyl-sn-glycero-3-phosphoryl)-1,3-bis-O-(2,3,4,6-tetra-O-benzyl-α-D-galactopyranosyl)glycerol 43

43

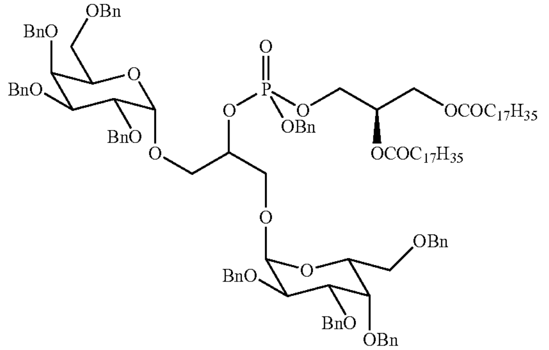

A solution of phosphoramidite 25 (163 mg, 0.189 mmol) in dichloromethane (17 mL) was cannulated onto a mixture of the alcohol 42 (145 mg, 0.127 mmol) and 1H-tetrazole (23.0 mg, 0.378 mmol) under argon. The reaction mixture was stirred at RT for 12 h then cooled in ice when a solution of MCPBA (75%, 105 mg, 0.426 mmol), pre-dried for 20 min over $MgSO_4$, was added to the reaction mixture. After a further 1 hr the reaction mixture was diluted with dichloromethane (30 mL) and quenched with the addition of 10% aqueous sodium thiosulfate (45 mL). The aqueous phase was further extracted with dichloromethane (35 mL) and the combined organic extract washed with sat. $NaHCO_3$ (2×40 mL) and dried ($MgSO_4$). After filtration the solvent was removed at reduced pressure to give the crude product that was purified by column chromatography on silica gel. Gradient elution with ethyl acetate/petroleum ether (20:80-30:70) afforded the title compound 43 (216 mg) as an inseparable mixture which was used without further purification. $^{31}P$ NMR (121.2 MHz, $CDCl_3$) δ 9.2, 9.1, −0.5.

Sodium(1,2-di-O-stearoyl-sn-glycero-3-phoshoryl)-2-[1,3-bis-O-(α-D-galactopyranoside)]glycerol 44

44

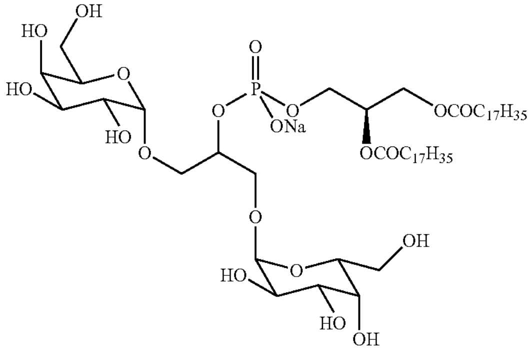

A mixture of the perbenzyl glycolipid 43 (70 mg, 0.037 mmol), $NaHCO_3$ (9.0 mg, 0.107 mmol) and Pd-black (95 mg) in $^{t}BuOH$ (4 mL) and $H_2O$ (1 mL) was hydrogenated at 300 psi/50° C. for 14 hrs. After removal of the hydrogen the reaction mixture was filtered through celite and the pad washed with $CHCl_3/MeOH/H_2O$ (70:40:08) (2×20 mL). Silica was added to the filtrate and the solvent removed at reduced pressure to give a free flowing solid. Gradient elution with $CHCl_3$→$CHCl_3/MeOH$ (80:20)→$CHCl_3/MeOH$ (70:40)→$CHCl_3/MeOH/H_2O$ (70:40:05) afforded the title compound 44 (10 mg, 0.0089 mmol, 24%) that was lyophilized to give a white solid; $^{1}H$ NMR (300 MHz, $CDCl_3/CD_3OD/D_2O$, 70:40:6) δ 5.30-5.20 (m, 1H), 4.93-4.88 (m, 2H), 4.48-4.40 (m, 1H), 4.20-4.16 (m, 1H), 4.00-3.60 (m, 19H), 2.39-2.28 (m, 4H), 1.62-1.50 (m, 4H), 1.38-1.20 (m, 56H), 0.90-0.81 (m, 6H); $^{31}P$ NMR (121.5 MHz, $CDCl_3/CD_3OD/D_2O$, 70:40:6) δ 0.52; LRMS-ESI (−ve) m/z 1102 (30%), 1074 (100), 1046 (50) 1018 (10); HRMS-ESI (−ve) (Found: m/z 1101.6657 $(M-Na)^-$. $C_{54}H_{102}O_{20}P$ requires m/z 1101.6708).

Example 1(i)

Synthesis of Compound 47

The total synthesis of compound 47 is represented schematically in FIG. 9.

Benzyl-octadecanyl-N,N-diisopropylphosphoramidite 45

45

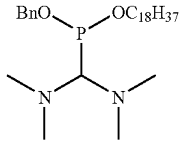

A solution of bis(benzyloxy)(diisopropylamino)phosphine (570 mg, 1.69 mmol) in dichloromethane (15 mL) was cannulated onto a mixture of 1-octadecanol (209 mg, 0.773 mmol) and 1H-tetrazole (54.0 mg, 0.771 mmol) under argon. The reaction mixture was stirred at RT for 2 hrs when the solvent was removed at reduced pressure to give the crude product that was purified by column chromatography on silica gel. Elution with $Et_3N$/EtOAc/petroleum ether (3:10:90) afforded the title compound 45 (322 mg, 0.634 mmol, 82%) as an oil; $^{1}H$ NMR (300 MHz, $CDCl_3$) δ 7.39-7.20 (m, 5H), 4.80-4.60 (m, 2H), 3.69-3.52 (m, 4H), 1.65-1.58 (m, 2H), 1.29-1.20 (m, 42H), 0.89-0.81 (m, 3H); $^{13}C$ NMR (75 MHz, $CDCl_3$) δ 140.2, 128.6, 127.5, 127.4, 65.7, 65.5, 64.2, 64.0, 43.4, 43.2, 32.3, 31.8, 31.7, 30.1, 29.7, 26.4, 25.1, 25.0, 23.1, 14.5; $^{31}P$ NMR (121.5 MHz, $CDCl_3$) δ 147.7; HRMS-ESI (+ve) (Found: m/z 526.4372 $(M+H_3O)^+$, $C_{31}H_{61}NO_3P$ requires m/z 526.4384).

2-O-(Benzyl-octadecyl-phosphoryl)-1,3-bis-O-(2,3,4,6-tetra-O-benzyl-α-D-mannopyranosyl)glycerol 46

46

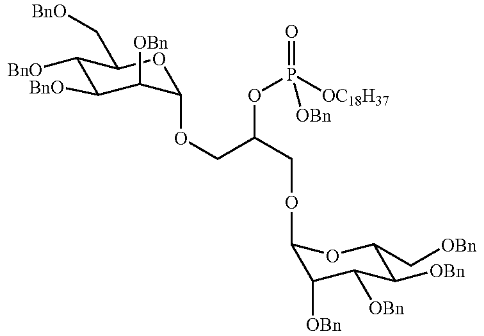

A solution of the phosphoramidite 45 (54 mg, 0.105 mmol) in dichloromethane (12 mL) was cannulated onto a mixture of the alcohol 12 (80 mg, 0.070 mmol) and 1H-tetrazole (11 mg, 0.161 mmol) under argon. The reaction mixture was stirred at RT for 2 hrs then cooled in ice when a solution of MCPBA (75%, 25 mg, 0.141 mmol), pre-dried for 20 min over $MgSO_4$, was added to the reaction mixture. After a further 1 hr the reaction mixture was diluted with dichloromethane (30 mL) and quenched with the addition of 10% aqueous $Na_2S_2O_3$ (45 mL). The aqueous phase was further extracted with dichloromethane (35 mL) and the combined organic extract washed with sat. $NaHCO_3$ (2×40 mL) and dried ($MgSO_4$). After filtration the solvent was removed at reduced pressure to give the crude product that was purified by column chromatography on silica gel. Gradient elution with ethyl acetate/petroleum ether (10:90→30:70) afforded the title compound 46 (70 mg, 0.045 mmol, 64%) as a thin film; $[\alpha]_D^{18}$ +31 (c 0.54, $CHCl_3$); $^1H$ NMR (300 MHz, $CDCl_3$) δ 7.40-7.10 (m, 45H), 4.97-4.40 (m, 21H), 4.00-3.55 (m, 18H), 1.51-1.42 (m, 2H), 1.30-1.15 (m, 30H), 0.88-0.81 (m, 3H); $^{13}C$ NMR (75 MHz, $CDCl_3$) δ 138.8, 128.9, 128.7, 128.3, 128.1, 127.9, 127.9, 99.0, 98.4, 80.6, 75.9, 75.4, 75.2, 75.1, 73.7, 73.0, 72.6, 72.4, 69.5, 68.5, 67.2, 66.9, 32.3, 30.6, 30.5, 30.1, 29.9, 29.7, 29.6, 25.8, 23.1, 14.5; $^{31}P$ NMR (121.2 MHz, $CDCl_3$) δ −0.12; HRMS-ESI (+ve) (Found: m/z 1576.8426 ($MNH_4^+$), $C_{96}H_{123}NO_{16}P$ requires m/z 1576.8579).

Sodium 2-O-(Octadecylphosphoryl)-1,3-bis-O-(α-D-mannopyranosyl)glycerol 47

47

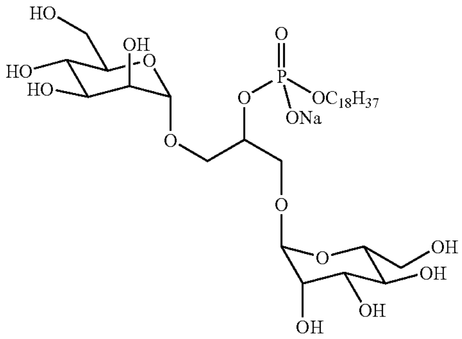

A mixture of the perbenzyl glycolipid 46 (36 mg, 0.023 mmol), $NaHCO_3$ (2.5 mg, 0.0.30 mmol) and Pd-black (69 mg) in $^t$BuOH (3 mL) and $H_2O$ (0.2 mL) was hydrogenated at 300 psi/50° C. for 14 hrs. After removal of the hydrogen the reaction mixture was filtered through celite and the pad washed with $CHCl_3/MeOH/H_2O$ (70:40:08) (2×20 mL). Silica was added to the filtrate and the solvent removed at reduced pressure to give a free flowing solid. Gradient elution with $CHCl_3$→$CHCl_3/MeOH$ (80:20)→$CHCl_3/MeOH$ (70:40)→$CHCl_3/MeOH/H_2O$ (70:40:02)→$CHCl_3/MeOH/H_2O$ (70:40:04)→$CHCl_3/MeOH/H_2O$ (70:40:08) afforded the title compound 47 (12 mg, 0.016 mmol, 71%) that was lyophilized to give a white solid $[\alpha]_D^{20}$ +47 (c 0.60, $CDCl_3/CD_3OD/D_2O$, 70:40:6); $^1H$ NMR (300 MHz, $CDCl_3/CD_3OD/D_2O$, 70:40:6) δ 4.87 (bs, 1H), 4.84 (bs, 1H), 3.91-3.60 (m, 19H), 1.61-1.55 (m, 2H), 1.30-1.19 (m, 30H), 0.92-0.82 (m, 3H); $^{13}C$ NMR (75 MHz, $CDCl_3/CD_3OD/D_2O$, 70:40:6) δ 102.0, 101.9, 74.6, 72.8, 72.2, 69.0, 68.5, 68.2, 67.7, 63.0, 33.6, 32.5, 31.4, 31.0, 27.5, 24.3, 15.6; $^{31}P$ NMR (121.5 MHz, $CDCl_3/CD_3OD/D_2O$, 70:40:6) δ 0.81; HRMS-ESI (−ve) (Found: m/z 747.3939 $(M-Na)^-$, $C_{33}H_{64}O_{16}P$ requires m/z 747.3938).

Example 1(j)

Synthesis of Compound 51

The total synthesis of compound 51 is represented schematically in FIG. 10.

2-Hydroxyethyl octadecanoate 48

48

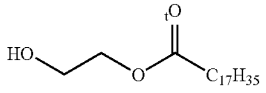

A solution of stearic anhydride (1.14 g, 2.06 mmol) in dichloromethane (30 mL) was cannulated into a stirred solution of ethylene glycol (1.10 mL, 19.7 mmol), DMAP (22 mg, 0.18 mmol) and triethylamine (0.300 mL, 2.16 mmol) in dichloromethane (20 mL). After stirring for 90 min. the reaction was quenched with the addition of $H_2O$ (100 mL). After separation of the phases the aqueous fraction was re-extracted with dichloromethane (2×50 mL) and the combined organic extract was washed with brine (70 mL). After drying ($MgSO_4$) and filtration the solvent was removed at reduced pressure to give the crude product that was purified by chromatography on silica gel. Gradient elution with ethyl acetate/petroleum ether (10:90→30:70) afforded the title compound 48 (265 mg, 0.807 mmol, 39%) as an oil; $^1H$ NMR (300 MHz, $CDCl_3$) δ 4.25-4.20 (m, 2H), 3.83-3.78 (m, 2H), 2.38 (t, 2H, J 7.5 Hz), 2.00-1.97 (m, 1H), 1.62-1.55 (m, 2H), 1.35-1.20 (m, 28H), 0.87-0.81 (m, 3H); $^{13}C$ NMR (75 MHz, $CDCl_3$) δ 174.6, 66.3, 61.7, 34.6, 32.3, 30.1, 29.8, 29.7, 29.6, 29.5, 25.3, 23.1, 14.5; HRMS-ESI (+ve) (Found: m/z 346.3323 ($MNH_4^+$). $C_{20}H_{44}NO_3$ requires m/z 346.3316).

Benzyl-(2-octadecanoyloxyethyl)-N,N-diisopropylphosphoramidite 49

49

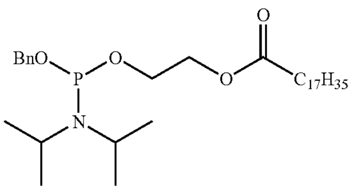

A solution of bis(benzyloxy)(diisopropylamino)phosphine (510 mg, 1.51 mmol) in dichloromethane (15 mL) was cannulated onto a mixture of 2-hydroxyethyl octadecanoate 48 (238 mg, 0.309 mmol) and 1H-tetrazole (50.0 mg, 0.714 mmol) under argon. The reaction mixture was stirred at RT for 1.5 hrs when the solvent was removed at reduced pressure to give the crude product that was purified by column chromatography on silica gel. Elution with $Et_3N/EtOAc$/petroleum ether (3:10:90) afforded 2-(benzyloxy-diisopropylamino-phosphoramidite)-ethyl octadecanoate 49 (366 mg, 0.600 mmol, 83%) as an oil; $^1H$ NMR (300 MHz, $CDCl_3$) δ

7.35-7.20 (m, 5H), 4.80-4.60 (m, 2H), 4.25-4.20 (m, 2H), 3.89-5.58 (m, 4H), 2.30 (t, 2H, J 7=8.0 Hz), 1.62-1.55 (m, 2H), 1.29-1.17 (m, 40H), 0.89-0.81 (m, 3H); $^{31}P$ NMR ($CDCl_3$) δ 149.5; HRMS-ESI (+ve) (Found: m/z 584.4399 $(M+H_3O)^+$. $C_{33}H_{63}NO_4P$ requires m/z 584.4438).

Benzyl-(2-octadecanoyloxyethyl-3-O-(2,3,4,6-tetra-O-benzyl-α-D-mannopyranosyloxy)propyl phosphate 50

50

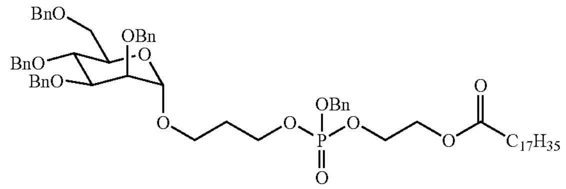

A solution of the phosphoramidite 49 (242 mg, 0.428 mmol) in dichloromethane (12 mL) was cannulated onto a mixture of the alcohol 29 (189 mg, 0.316 mmol) and 1H-tetrazole (50.0 mg, 0.714 mmol) under argon. The reaction mixture was stirred at RT for 3 hrs then cooled in ice when a solution of MCPBA (75%, 156 mg, 0.633 mmol), pre-dried for 20 min over $MgSO_4$, was added to the reaction mixture. After a further 1 hr the reaction mixture was diluted with dichloromethane (30 mL) and quenched with the addition of 10% aqueous sodium thiosulfate (45 mL). The aqueous phase was further extracted with dichloromethane (35 mL) and the combined organic extract washed with sat $NaHCO_3$ (2×40 mL) and dried ($MgSO_4$). After filtration the solvent was removed at reduced pressure to give the crude product that was purified by column chromatography on silica gel. Gradient elution with ethyl acetate/petroleum ether (20:80→45:55) afforded the title compound 50 (226 mg, 0.209 mmol, 66%) as a thin film; $[\alpha]_D^{18}$ +13.6 (c 1.55, EtOAc); $^1H$ NMR (300 MHz, $CDCl_3$) δ 7.40-7.10 (m, 25H), 5.10-5.03 (m, 2H), 4.90-4.42 (m, 9H), 4.15-3.65 (m, 13H), 3.43-3.98 (m, 1H), 2.30-2.21 (m, 2H), 1.90-1.80 (m, 2H), 1.60-1.50 (m, 2H), 1.30-1.20 (m, 28H), 0.88-0.81 (m, 3H); $^{13}C$ NMR (75 MHz, $CDCl_3$) δ 173.9, 138.9, 138.8, 129.0, 128.7, 128.5, 128.3, 128.2, 128.0, 127.9 (7), 127.9, 98.4, 80.6, 75.6, 75.2, 75.0, 73.8, 73.0, 72.5, 72.3, 69.8, 69.7, 69.6, 65.8, 65.7, 65.3, 63.7, 63.2, 63.1, 34.4, 32.3, 30.6, 30.1, 29.9, 29.8, 29.7, 29.5, 25.2, 23.1, 14.6; $^{31}P$ NMR (121.2 MHz, $CDCl_3$) δ 0.38; HRMS-ESI (+ve) (Found: m/z 1096.6257 $(MNH_4^+)$. $C_{64}H_{91}NO_{12}P$ requires m/z 1096.6273).

Benzyl-(2-octadecanoyloxyethyl)-3-O-(α-D-mannopyranosyloxy)propyl phosphate 51

51

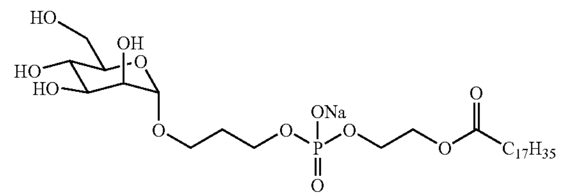

A mixture of the perbenzyl glycolipid 50 (111 mg, 0.103 mmol), $NaHCO_3$ (11.0 mg, 0.131 mmol) and Pd-black (75 mg) in $^t$BuOH (6 mL) and $H_2O$ (0.95 mL) was hydrogenated at 300 psi/50° C. for 14 hrs. After removal of the hydrogen the reaction mixture was filtered through Celite and the pad washed with $CHCl_3/MeOH/H_2O$ (70:40:08) (2×20 mL). Silica was added to the filtrate and the solvent removed at reduced pressure to give a free flowing solid. Gradient elution with $CHCl_3$→$CHCl_3$/MeOH (80:20)→$CHCl_3$/MeOH (70:40)→$CHCl_3/MeOH/H_2O$ (70:40:05) afforded the title compound 51 (63 mg, 0.096 mmol, 93%) that was lyophilized to give a white solid $[\alpha]_D^{20}$ +22.9 (c 0.105, $CHCl_3/MeOH/H_2O$, 70:40:8); $^1H$ NMR (300 MHz, $CDCl_3/CD_3OD/D_2O$, 70:40:6) δ 4.59 (bs, 1H), 4.01-3.95 (m, 2H), 3.82-3.21 (m, 12H), 2.34 (t, 2H, J 7.4 Hz), 1.70-1.59 (m, 2H), 1.41-1.32 (m, 2H), 1.10-1.00 (m, 28H), 0.70-0.62 (m, 3H); $^{13}C$ NMR (75 MHz, $CDCl_3/CD_3OD/D_2O$, 70:40:6) δ 176.3, 101.6, 74.3, 72.9, 72.4, 69.0, 65.6, 65.1, 65.0 (5), 64.0, 63.0, 35.8, 33.6, 32.0, 31.4, 312, 31.0, 30.9, 26.6, 24.3, 15.6; $^{31}P$ NMR (121.5 MHz, $CDCl_3/CD_3OD/D_2O$, 70:40:6) δ 0.87; m/s (E/S). found 627.3473 $(M-Na)^-$, calcd for $C_{29}H_{56}O_{12}P$ requires 627.3504. HRMS-ESI (−ve) (Found: m/z 627.3473 $(M-Na)^-$, $C_{29}H_{56}O_{12}P$ requires m/z 627.3504).

Example 2

In Vivo Efficacy

Mouse Eosinophilia Model

Model

An ovalbumin (OVA) induced airway eosinophilia mouse model of atopic airway inflammation was used to determine the effectiveness of the synthetic molecules in suppressing the development of airway eosinophilia. This model is widely used to establish "asthma-like effects" in mice—see for example, Erb et al., (1998); Herz et al., (1998); and Randaolf et al., (1999).

Mice

C57B1/6J mice were bred and housed at the Wellington School of Medicine Animal Facility (Wellington, New Zealand). The experimental procedures were approved by the animal ethics committee and were in accordance with University of Otago (Dunedin, New Zealand) guidelines for care of animals.

OVA-Induced Airway Inflammation

OVA Sensitisation—6 to 8 week-old mice (4 to 5 mice per group) were injected intraperitoneally (i.p.) with 2 μg ovalbumin in 200 μl alum adjuvant at day 0. A booster intraperitoneal injection of 2 μg ovalbumin in 200 μl alum adjuvant was administered at day 14.

Experimental Treatments

The mice were randomly allocated to treatment groups with control mice receiving only PBS (Phosphate Buffered Saline), while treated mice received either PIM extracted from *Mycobacterim bovis*, or one of the synthetic molecules.

Treatment Protocols with PIM Extract or Synthetic Molecules 7 to 14 days following the second i.p. injection, mice were anaesthetised. Each mouse was treated intranasally as outlined in Table 1 with the indicated concentrations of NM extract or a synthetic molecule of the invention in 50 μl of PBS. Control mice were given PBS intranasally.

TABLE 1

| Summary of Experiments | | |
|---|---|---|
| 'PIM' Type | Dose Rates (µ/g 'PIM' per ml solution) | Number Of Mice |
| *M. Bovis* PIM | 0, 0.02, 0.2, 2.0 | 17 including 5 controls* |
| Compound 15 | 0, 0.02, 0.2, 2.0 | 22 including 5 controls* |

*The same controls (n = 5) were used for each treatment group.

OVA challenge—7 days following treatment with the test molecules, mice were anaesthetised and challenged intranasally with 50 µl of 2 mg/ml ovalbumin in PBS.

Measurements of Airway Eosinophilia 4 days after intranasal airway challenge with OVA the mice were sacrificed. The trachea was cannulated and bronchoalveolar lavage (SAL) was performed (3×1 ml PBS). Total BAL cell numbers were counted and spun onto glass slides using a cytospin. Percentages of eosinophils, macrophages, lymphocytes and neutrophils were determined microscopically using standing histological criteria.

Results

TABLE 2

| Least square means of eosinophil counts (×10$^6$) by dose rate of the test molecule | | |
|---|---|---|
| Dose Rate (µg/ml) | Mean Eosinophil Count (×10$^6$)* | s.e.m. |
| 0 | 0.272$^a$ | 0.040 |
| 0.02 | 0.084$^b$ | 0.044 |
| 0.2 | 0.123$^b$ | 0.044 |
| 2 | 0.114$^b$ | 0.042 |

*Means with different letters are significantly different (P < 0.05).

TABLE 3

| Least square means of Eosinophilia counts (*10$^6$) by test molecule type | | |
|---|---|---|
| Test Molecule Type | Mean Eosinophil Count (×10$^6$) | s.e.m |
| *M. bovis* PIM | 0.153 | 0.031 |
| Compound 15 | 0.144 | 0.030 |

Figure 11:
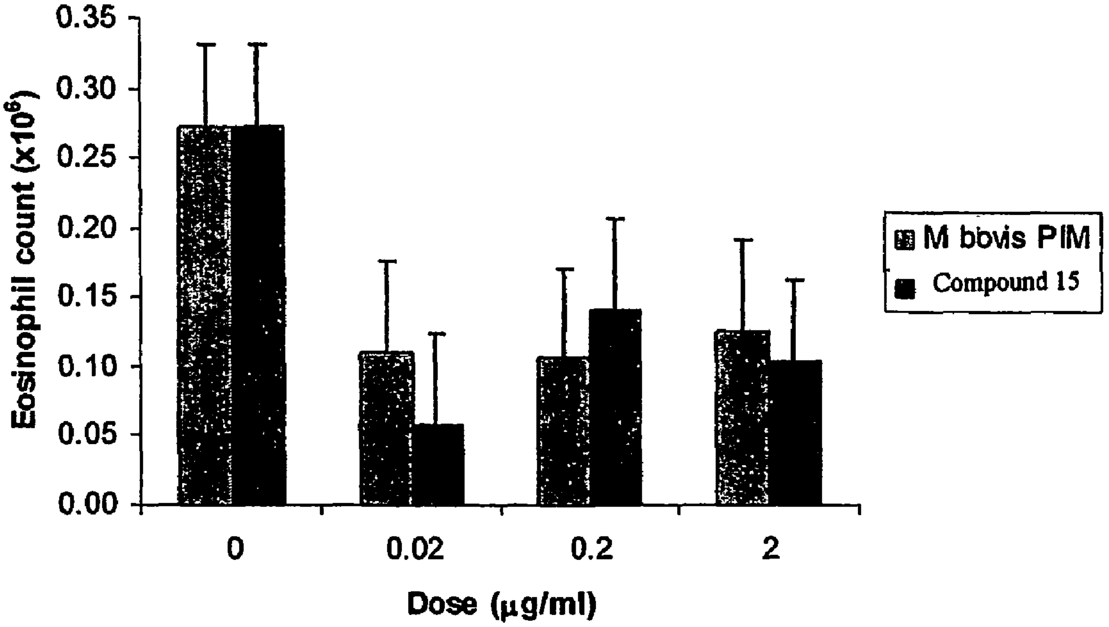
FIG. 11 shows the mean (±s.e.m.) eosinophil count ($\times10^6$) after administration of a compound of the present invention and a comparative PIM extract using the mouse in vivo induced airway eosinophilia model.

The results of one comparative experiment are presented in Tables 2 and 3 and FIG. 11. The data were analysed as a single group as the experiment tested two molecules at the same time. The statistical model included terms for dose and molecule type as fixed effects and the dose by molecule type interaction. The mean eosinophil counts for the two molecule types are presented in FIG. 11.

Overall, the dose of PIM extract or synthetic molecule was highly significant (P<0.01). All animals treated with either PIM extract or a synthetic molecule had a reduced eosinophil count compared to the control animals. No significant differences were found between dose rates in the pair-wise comparisons (Table 2). The overall effect of the type of molecule was not significant (P>0.05; Table 3). Both molecule types appear to be equally effective in reducing the eosinophilia in this experiment meaning that it is likely the active structural element or elements required to produce this effect on the degree of eosinophilia are present in both molecules.

Compound 17 was not biologically active. As this molecule did not include an E or B group, this result indicated that at least one or both such groups are essential for biological activity (results not shown).

Example 3

In Vitro Efficacy

A whole spleen from a C57BL-6 mouse was homogenised, strained through gauze and resuspended in complete Iscove's Modified Dulbecco's Medium (IMDM). The cell suspension was centrifuged and the cells resuspended in RBC lysis buffer. The cell suspension was centrifuged, the supernatant removed and the cell resuspended in complete IBM (10% of oetal bovine serum) (cIMDM). The cells were plated out at 10$^6$ cells per well.

Compounds were dissolved in PBS and added to the wells at a concentration of 5 µg/ml and the cells incubated for 24 hours. Supernatants were removed for cytokine analysis. Cytokine levels (IL-10, IL-12, IFNγ, IL-4) were measured by ELISA analysis. The cells were then stained with Fluorescent antibodies (Pharmigen) for the activation markers CD80, CD86 (Dendritic cells) for DC and MHCII (macrophages). Levels of expression of the activation markers for each cell type were determined by FACS.

Results

TABLE 4

| Cytokine production in vitro | | | | |
|---|---|---|---|---|
| | In vitro activity | | | |
| | IL-10 | IL-12 | IFNγ | IL-4 |
| Compound | Compared with PIM-2 control | | | |
| PIM-2$_{2,6}$ (Positive control) | 1.0 | 1.0 | 1.0 | 1.0 |
| L-α-Phosphatidylinositol* (Negative control) | X | X | 0.39 | X |
| 7** | X | 1.03 | 1.26 | X |
| 28 | 0.36 | 1.15 | 0.62 | X |
| 31 | X | 1.80 | 0.75 | X |
| 36 | 0.60 | 1.59 | 0.05 | 4.29 |
| 51 | 0.49 | X | X | X |
| 15 | X | X | 0.98 | X |
| 44 | X | 0.14 | X | X |
| 47 | 0.53 | 0.56 | 0.03 | 1.94 |

wherein X denotes a level that is less than the background of the assay.

The levels of IL-10, IL-12, IFNγ and IL-4 are compared with the levels recorded in response to PIM-2 (positive control).

*Sigma P-5954.

**denotes that the compound was dissolved in Tween/PBS. In this case, the PIM-2 control was also in 0.02% Tween/PBS.

All of the synthetic molecules of the present invention showed biological activity in vitro.

Compounds 7, 28 and 31 each induced production of notable levels of both IL-12 and INFγ. Compound 36 induced production of IL-12 and IL-4 at levels greater than PIM-2$_{2,6}$. Compound 51 appears to specifically induce low levels of IL-10 and compound 15 specifically induced IFNγ at levels comparable to PIM-2$_{2,6}$. Compound 44 induced a small amount of IL-12. Compound 47 induced production of IL-10 and IL-12 and greater levels of IL-4 compared to PIM-2$_{2,6}$.

The similarity in the cytokine profiles for compound 7, 28 and 31 follows a similarity in their structures. All of these compounds possess the sn-1,2-di-O-stearoylglyceryl-3-phosphate group and are linked to a either an α-D-mannopyranosyl (a single D-mannose residue) or (16)-α-D-mannopyranosyl)-α-D-mannopyranosyl (a disaccharide made up of D-mannose residues) by a simple ethyl or propyl spacer.

Compound 36 has similar structural features to 7, 8 and 31 but differs in that the spacer (a cyclohexyl) group is rigid and would restrict the positions of the mannose and the sn-1,2-di-O-stearoylglyceryl-3-phosphate units with respect to each other.

Compound 51 is structurally similar to 7, 28 and 31 except that it possesses a 1-O-stearoylethyl-2-phosphate group. This change appears to have reduced the cyctokine production compared to $PIM2_{2,6}$.

Compounds 15, 44 and 47 are structurally related to each other in that the spacer group A) is derived from glycerol and that each end of the glycerol unit is bonded to a carbohydrate residue. It is notable that when the carbohydrate residues are two α-D-galactosyl units (ie compound 44) that only a low level of IL-12 production occurred. Compounds 15 and 47 each contain two mannose residues. Compound 47 differs from compound 15 in that it does not possess a diacyl glyceryl unit (A) but instead possesses a C18-alkyl group. This appears to have changed the cytokine profile.

Example 4

Pharmaceutical Formulations

The compounds suitable for use in the present invention may be administered alone, although it is preferable that they be administered as a pharmaceutical formulation. The compounds of the invention are highly biologically active and it is anticipated that, for airways or nasal mucosal administration, from 1 to 500 μg/ml of the active ingredient would be present in the formulation.

REFERENCES

Remington's Pharmaceutical Sciences, $16^{th}$ edition, Oslo, A. (ed), 1980.

Dreef, C. E., W. Schiebler, G. A. Van der Marel, and J. H. Van Boom. (1991). Synthesis of 5-phosphonate analogs of myo-inositol 1,4,5-trisphosphate: possible intracellular calcium antagonists. *Tetrahedron Letters* 32:6021-4.

Erb, K. J., Holloway, J. W., Sobeck, A., Moll, H., Le Gros, G. (1998). Infection of mice with *Mycobacterium bovis* Calmette-Guerin (BCG) suppresses allergen-induced airway eosinophilia. *J. Exp. Med.* 187: 561-569.

Herz, U., Gerhold, K., Gruber, C., Braun, A., Wahn, U., Renz, H., Paul, K. (1998). BCG infection suppresses allergic sensitisation and development of increased airway reactivity in an animal model. *J. Allergy Clin. Immunol.* 102: 867-874.

Hirooka, M., A. Yoshimura, I. Saito, F. Ikawa, Y. Uemoto, S. Koto, A. Takabatake, A. Taniguchi, Y. Shinoda, and A. Morinaga. (2003). Glycosylation using hemiacetal sugar derivatives: Synthesis of O-a-D-rhamnosyl-(1->3)-O-a-D-rhamnosyl-(1->2)-D-rhamnose and O-a-D-tyvelosyl-(1->3)-O-a-D-mannosyl-(1->4)-L-rhamnose. *Bulletin of the Chemical Society of Japan* 76:1409-1421.

Iranpoor, N., T. Tarrian, and Z. Movahedi. (1996). FeCl3.6H2O supported on SiO2 catalyzed ring-opening of epoxides with alcohols, acetic acid, water, chloride, bromide, and nitrate ions. *Synthesis:* 1473-1476.

Itano, K., K. Yamasaki, C. Kihara, and O. Tanaka. (1980). Stereospecific preparation of monoglucosides of optically active trans-1,2-cyclohexanediols by enzymic trans-D-glucosylation and carbon-13 NMR spectroscopy of the resulting mono-D-glucopyranosides. *Carbohydrate Research* 87:27-34.

Randolf, D. A., Stephens, R., Carruthers, C. J., Chaplin, D. D. (1999). Cooperation between Th1 and Th2 cells in a murine model of eosinophilic airway inflammation *J. Clinical Investigation,* 104:1021-1029.

Crossman, A., Jr., Brimacombe, J. S. & Ferguson, M. A. J. (1997). Parasite glycoconjugates. Part 7. Synthesis of further substrate analogs of early intermediates in the biosynthetic pathway of glycosylphosphatidylinositol membrane anchors. *Journal of the Chemical Society, Perkin Transactions* 1: *Organic and Bio-Organic Chemistry,* 2769-2774.

Gigg, J., Gigg, R., Payne, S. & Conant, R. (1985). The allyl group for protection in carbohydrate chemistry. Part 15. Synthesis of propyl 4-O-(3,6-di-O-methyl-b-D-glucopyranosyl)-2,3-di-O-methyl-a-D-rhamnopyranoside. *Carbohydrate Research* 141, 91-97.

Gilleron, M., Quesniaux, V. F. J. & Puzo, G. (2003). Acylation state of the phosphatidylinositol hexamannosides from *Mycobacterium bovis* Bacillus Calmette Guerin and *Mycobacterium tuberculosis* H37Rv and its implication in Toll-like receptor response. *Journal of Biological Chemistry* 278, 29880-29889.

Gilleron, M., Ronet, C., Mempel, M., Monsarrat, B., Gachelin, G. & Puzo, G. (2001). Acylation state of the phosphatidylinositol mannosides from *Mycobacterium bovis* bacillus Calmette Guerin and ability to induce granuloma and recruit natural killer T cells. *Journal of Biological Chemistry* 276, 34896-34904.

Green, M. M., Gross, R. A., Cook, R. & Schiring, F. C. (1987). Broken worm and worm-like models for polyisocyanates. *Macromolecules* 20, 2636-2638.

Hirth, G. & Barner, R. (1982). Synthesis of glyceryl ether phosphatides. Part 1. Preparation of 1-O-octadecyl-2-O-acetyl-sn-glyceryl-3-phosphorylcholine ('platelet activating factor'), its enantiomers and some analogous compounds. *Helvetica Chimica Acta* 65, 1059-1084.

Hirth, G., Saroka, H., Bannwarth, W. & Barner, R. (1983). Synthesis of glyceryletherphosphatides. Part 2. Preparation of 2-O-acetyl-1-O—[(Z)-9-octadecenyl]-sn-glyceryl-3-phosphorylcholine ('Oleyl-PAF'), of its enantiomer and some analogous, unsaturated compounds. *Helvetica Chimica Acta* 66, 1210-1240.

Koizumi, K., Tanimoto, T., Okada, Y., Nakanishi, N., Kato, N., Takagi, Y. & Hashimoto, H. (1991). Characterization of five isomers of branched cyclomaltoheptaose (b CD) having degree of polymerization (d.p.)=9: reinvestigation of three positional isomers of diglucosyl-b CD. *Carbohydrate Research* 215, 127-136.

Koto, S., Morishima, N., Miyata, Y. & Zen, S. (1976). Preparation of 2,3,4,6-tetra-O-benzyl-D-mannose. *Bulletin of the Chemical Society of Japan* 49, 2639-2640.

Koto, S., Morishima, N., Shichi, S., Haigoh, H., Hirooka, M., Okamoto, M., Higuchi, T., Shimizu, K., Hashimoto, Y. & et al. (1992). Dehydrative glycosylation using heptabenzyl derivatives of glucobioses and lactose. *Bulletin of the Chemical Society of Japan* 65, 3257-3274.

Lindberg, J., Ekeroth, J. & Konradsson, P. (2002). Efficient Synthesis of Phospholipids from Glycidyl Phosphates. *Journal of Organic Chemistry* 67, 194-199.

Lindhorst, T. K., Dubber, M., Krallmann-Wenzel, U. & Ehlers, S. (2000). Cluster mannosides as inhibitors of type 1 fimbriae-mediated adhesion of *Escherichia coli*: pentaerythritol derivatives as scaffolds. *European Journal of Organic Chemistry,* 2027-2034.

RajanBabu, T. V., Fukunaga, T. & Reddy, G. S. (1989). Stereochemical control in hex-5-enyl radical cyclizations: from carbohydrates to carbocycles. 3. *Journal of the American Chemical Society* 111, 1759-1769.

Severn, W. B., Jones, A. M., Kittelberger, R., de Lisle, G. W., and Atkinson, P. H., (1997). Improved procedure for the isolation and purification of lipo-aribomanan *Mycobacterium bovis* strain AN5. *J. Microbol. Methods* 28, 123-130.

Watanabe, Y., Nakamoto, C. & Ozaki, S. (1993). Glycosidation based on phosphite chemistry. *Synlett,* 115-116.

Watanabe, Y., Nakamoto, C., Yamamoto, T. & Ozaki, S. (1994). Glycosylation using glycosyl phosphite as a glycosyl donor. *Tetrahedron* 50, 6523-6536.

Kakimoto, K., T. Nakamura, K. Ishii, T. Takashi, H. Iigou, H. Yagita, K. Okumura, and K. Onoue. (1992). The effect of anti-adhesion molecule antibody on the development of collagen-induced arthritis. *Cellular immunology* 142:326-37.

Knoerzer, D. B., M. G. Donovan, B. D. Schwartz, and L. J. Mengle-Gaw. (1997). Clinical and histological assessment of collagen-induced arthritis progression in the diabetes-resistant BB/Wor rat. *Toxicologic pathology* 25:13-9.

Halloran, M. M., Z. Szekanecz, N. Barquin, G. K. Haines, and A. E. Koch. (1996). Cellular adhesion molecules in rat adjuvant arthritis. *Arthritis and rheumatism* 39:810-9.

Schimmer, R. C., D. J. Schrier, C. M. Flory, K. D. Laemont, D. Tung, A. L. Metz, H. P. Friedl, M. C. Conroy, J. S. Warren, B. Beck, and P. A. Wards. (1998). Streptococcal cell wall-induced arthritis: requirements for IL-4, IL-10, IFN-g, and monocyte chemoattractant protein-1. *Journal of Immunology* 160:1466-1471.

Oppenheimer-Marks, N., R. I. Brezinschek, M. Mohamadzadeh, R. Vita, and P. E. Lipsky. (1998). Interleukin 15 is produced by endothelial cells and increases the transendothelial migration of T cells in vitro and in the SCID mouse-human rheumatoid arthritis model in vivo. *Journal of Clinical Investigation* 101:1261-1272.

Gross, D. M., T. Forsthuber, M. Tary-Lehmann, C. Etling, K. Ito, Z. A. Nagy, J. A. Field, A. C. Steere, and B. T. Huber. (1998). Identification of LFA-1 as a candidate autoantigen in treatment-resistant Lyme arthritis. *Science* (Washington, D.C.) 281:703-706.

Mulligan, M. S., A. A. Vaporciyan, R. L. Warner, M. L. Jones, K. E. Foreman, M. Miyasaka, R. F. Todd, III, and P. A. Ward. (1995). Compartmentalized roles for leukocytic adhesion molecules in lung inflammatory injury. *Journal of Immunology* 154:1350-63.

Bennet, C. F., D. Kornbrust, S. Henry, K. Stecker, R. Howard, S. Cooper, S. Dutson, W. Hall, and H. I. Jacoby. (1997). An ICAM-1 antisense oligonucleotide prevents and reverses dextran sulfate sodium-induced colitis in mice. *Journal of Pharmacology and Experimental Therapeutics* 280:988-1000.

Y Hasagawa, K Yokono, T Taki, K Amano, Y Tominaga, R Yoneda, N Yagi, S Maeda, H Yagita, and K Okumura (1994). Prevention of autoimmune insulin-dependent diabetes in non-obese diabetic mice by anti-LFA-1 and anti-ICAM-1 mAb. *Int Immunol* 6:831-838.

Herrold, K. C., V. Vezys, A. Gage, and A. G. Montag. (1994). Prevention of autoimmune diabetes by treatment with anti-LFA-1 and anti-ICAM-1 monoclonal antibodies. *Cellular Immunology* 157:489-500.

INDUSTRIAL APPLICATION

As will be appreciated from the above, the primary application of the invention is in the treatment of inflammatory or immune cell-mediated disorders. That treatment may be prophylactic, to prevent risk of developing such diseases or disorders, or therapeutic, to suppress established disease or symptoms.

The pharmaceutical compositions of the invention may be formulated for administration by any route depending on the nature of the disease or disorder to be treated. For example, for asthma, the composition will preferably be formulated for respiratory administration by the intranasal or inhaled route. For arthritis or diabetes, the composition will preferably be formulated for oral or subcutaneous administration. For rhinitis, the compositions will preferably be formulated for oral, or nasal mucosal delivery.

The invention also provides a process for efficient and economical large scale production of the synthetic molecules of the invention for use as an active ingredient in the pharmaceutical compositions.

It will be appreciated that the present invention is not limited to the above examples only, many variations, which may readily occur to a skilled worker, being possible without departing from the scope of the invention as set out in the accompanying claims.

What we claim is:

1. A synthetic molecule of formula I:

A-B-E-D (I)

Wherein A represents R, or a glyceride group having the formula Ia or Ib:

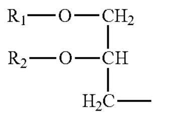

(Ia)

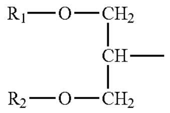

(Ib)

wherein R is a linear or branched alkyl of up to 40 carbon atoms;

$R_1$ and $R_2$ are independently H, alkyl or acyl and wherein the alkyl or acyl groups are linear or branched having up to 40 carbon atoms;

B is phosphate;

E comprises a spacer or linker group providing a linkage between groups B and D and is selected from the group consisting of:

$—C_aHR_3—C_bH(CH_2G)$-;

$—C_aH(CH_2G)$-$C_bHR_4$—;

$—C_aH(CH_2G)$-$C_bH(CH_2G)$-;

wherein carbon atom $C_a$ is linked to B and carbon atom $C_b$ is linked to D, and wherein $R_3$ and $R_4$ are independently selected from the group consisting of H, $CH_2OH$, and $(CH(OH))_m—CH_2OH$, wherein m=1 to 6; and D and G independently consist of an optionally acylated glycosyloxy sugar or an optionally acylated oligoglycosyloxy sugar moiety of 2 to 12 α-1,2 and/or α-1,6 linked sugars, wherein the sugar(s) are selected from the group consisting of D-mannose, D-galactose, D-glucose, D-glucosamine, N-acetylglucosamine, and 6-deoxy-L-mannose, wherein an oligoglycosyloxy sugar moiety may comprise the same or different sugars.

2. A synthetic molecule as claimed in claim 1, wherein R is a linear or branched alkyl of between 6 and 22 carbon atoms.

3. A synthetic molecule as claimed in claim 1, wherein R is a linear or branched alkyl of between 16 and 20 carbon atoms.

4. A synthetic molecule as claimed in claim 1 wherein the alkyl or acyl groups of $R_1$ and $R_2$ are linear or branched having between 6 and 22 carbon atoms.

5. A synthetic molecule as claimed in claim 3, wherein the alkyl or acyl groups of $R_1$ and $R_2$ are linear or branched having between 16 and 20 carbon atoms.

6. A synthetic molecule as claimed in claim 1, wherein D consists of an optionally acylated glycosyloxy sugar moiety or an optionally acylated oligoglycosyloxy sugar moiety of 2 to 6 α-1,2 and/or α-1,6 linked sugars.

7. A synthetic molecule as claimed in claim 1, wherein $R_1$ and $R_2$ are fatty acids independently selected from the group consisting of myristate, palmitate, heptadecanoate, stearate, tuberculostearate; E is $—C_aHR_3C_bH(CH_2G)-$ or $—C_aH(CH_2G)-C_bHR_4—$, wherein $R_3$ or $R_4$ are H and D and G independently consist of a glycosyloxy mannose moiety or an oligoglycosyloxy mannose moiety of 2 to 12 α-1,2 and/or α-1,6-linked mannose sugars.

8. A pharmaceutical composition comprising at least one compound of formula (I) as defined in claim 1, or a pharmaceutically acceptable salt thereof together with a pharmaceutically acceptable carrier.

9. A compound of formula (I), as defined in claim 1, selected from the group consisting of:

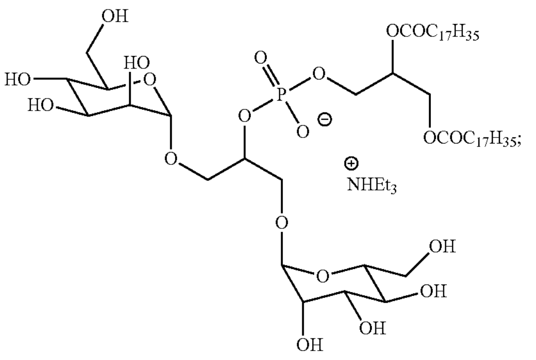

-continued

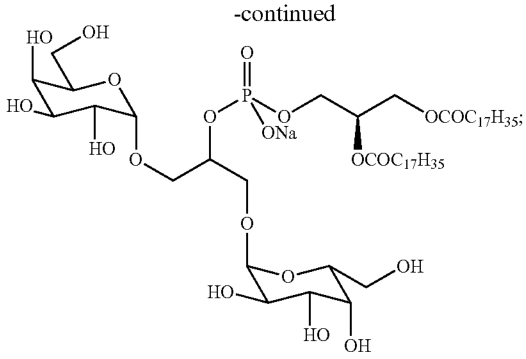

and

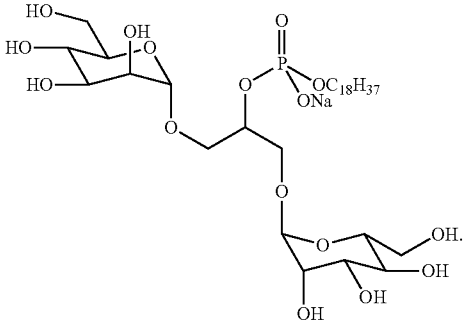

* * * * *